(12) United States Patent
Petroff et al.

(10) Patent No.: US 11,684,242 B2
(45) Date of Patent: Jun. 27, 2023

(54) IMAGING SYSTEM

(71) Applicant: Gentuity, LLC, Sudbury, MA (US)

(72) Inventors: Christopher Petroff, Groton, MA (US); Michael Atlas, Arlington, MA (US); Christopher Petersen, Carlisle, MA (US); Christopher Battles, Seymour, CT (US); Jiyuan Yin, Acton, MA (US); Nareak Douk, Lowell, MA (US); David W. Kolstad, Carlisle, MA (US); Giovanni Ughi, Arlington, MA (US); Lindsy Peterson, Woburn, MA (US); J. Christopher Flaherty, Auburndale, FL (US); R. Maxwell Flaherty, Topsfield, MA (US)

(73) Assignee: Gentuity, LLC, Sudbury, MA (US)

(*) Notice: Subject to any disclaimer, the term of this patent is extended or adjusted under 35 U.S.C. 154(b) by 276 days.

(21) Appl. No.: 16/764,087

(22) PCT Filed: Nov. 28, 2018

(86) PCT No.: PCT/US2018/062766
§ 371 (c)(1),
(2) Date: May 14, 2020

(87) PCT Pub. No.: WO2019/108598
PCT Pub. Date: Jun. 6, 2019

(65) Prior Publication Data
US 2020/0288950 A1    Sep. 17, 2020

Related U.S. Application Data

(60) Provisional application No. 62/671,142, filed on May 14, 2018, provisional application No. 62/591,403, filed on Nov. 28, 2017.

(51) Int. Cl.
*A61B 1/00* (2006.01)
*A61B 1/07* (2006.01)
(Continued)

(52) U.S. Cl.
CPC ...... *A61B 1/00133* (2013.01); *A61B 1/00126* (2013.01); *A61B 1/00128* (2013.01);
(Continued)

(58) Field of Classification Search
CPC . A61B 1/00133; A61B 5/0066; A61B 5/0084; A61B 5/6852; A61B 2562/0233
See application file for complete search history.

(56) References Cited

U.S. PATENT DOCUMENTS 4,554,929 A    11/1985    Samson et al.
4,566,330 A    1/1986    Fujii et al.
(Continued)

FOREIGN PATENT DOCUMENTS

AU    2014200116    1/2014
CN    1684624    10/2005
(Continued)

OTHER PUBLICATIONS

Extended European Search Report dated Jun. 8, 2022 issued in related European Application No. 21217738.0.
(Continued)

*Primary Examiner* — Michael A Lyons
(74) *Attorney, Agent, or Firm* — Onello & Mello, LLP

(57) ABSTRACT

An imaging system for use in a patient is provided. The system includes an imaging probe, a rotation assembly, and a retraction assembly. The imaging probe collects image data from a patient site and includes an elongate shaft with a proximal end and a distal portion, with a lumen extending therebetween. A rotatable optical core is positioned within the elongate shaft lumen and an optical assembly is posi-
(Continued)

tioned in the elongate shaft distal portion. The optical assembly directs light to tissue at the patient site and collects reflected light from the tissue. The rotation assembly connects to the imaging probe and rotates the optical assembly. The retraction assembly connects to the imaging probe and retracts the optical assembly and the elongate shaft in unison.

18 Claims, 26 Drawing Sheets

(51) Int. Cl.
*A61B 17/12* (2006.01)
*A61M 5/00* (2006.01)
*A61B 5/00* (2006.01)

(52) U.S. Cl.
CPC .............. *A61B 1/07* (2013.01); *A61B 5/0066* (2013.01); *A61B 5/0084* (2013.01); *A61B 5/6852* (2013.01); *A61B 17/1214* (2013.01); *A61M 5/007* (2013.01); *A61B 2017/1205* (2013.01); *A61B 2562/0233* (2013.01)

(56) References Cited

U.S. PATENT DOCUMENTS

| | | |
|---|---|---|
| 4,583,184 A | 4/1986 | Murase |
| 4,594,895 A | 6/1986 | Fujii |
| 4,597,292 A | 7/1986 | Fujii et al. |
| 4,646,748 A | 3/1987 | Fujii et al. |
| 4,753,248 A | 6/1988 | Engler et al. |
| 4,951,677 A | 8/1990 | Crowley et al. |
| 4,957,482 A | 9/1990 | Shiber |
| 4,961,427 A | 10/1990 | Namekawa et al. |
| 5,002,059 A | 3/1991 | Crowley et al. |
| 5,039,193 A | 8/1991 | Snow et al. |
| 5,058,587 A | 10/1991 | Kohno et al. |
| 5,118,405 A | 6/1992 | Kaneko et al. |
| 5,127,405 A | 7/1992 | Alcala et al. |
| 5,143,075 A | 9/1992 | Ishizuka |
| 5,151,603 A | 9/1992 | Nakamura |
| 5,152,277 A | 10/1992 | Honda et al. |
| 5,158,086 A | 10/1992 | Brown et al. |
| 5,212,671 A | 5/1993 | Fujii et al. |
| 5,219,335 A | 6/1993 | Willard et al. |
| 5,321,501 A | 6/1994 | Swanson et al. |
| 5,331,309 A | 7/1994 | Sakai |
| 5,383,467 A | 1/1995 | Auer et al. |
| 5,443,781 A | 8/1995 | Saab |
| 5,456,245 A | 10/1995 | Bornhop et al. |
| 5,459,570 A | 10/1995 | Swanson et al. |
| 5,554,139 A | 9/1996 | Okajima |
| 5,568,314 A | 10/1996 | Omori et al. |
| 5,568,503 A | 10/1996 | Omori |
| 5,644,427 A | 7/1997 | Omori et al. |
| 5,647,359 A | 7/1997 | Kohno et al. |
| 5,649,897 A | 7/1997 | Nakamura et al. |
| 5,689,316 A | 11/1997 | Hattori et al. |
| 5,738,100 A | 4/1998 | Yagami et al. |
| 5,745,163 A | 4/1998 | Nakamura et al. |
| 5,774,175 A | 6/1998 | Hattori |
| 5,774,261 A | 6/1998 | Omori et al. |
| 5,793,341 A | 8/1998 | Omori et al. |
| 5,818,399 A | 10/1998 | Omori et al. |
| 5,860,923 A | 1/1999 | Lenker et al. |
| 5,976,017 A | 11/1999 | Omori et al. |
| 5,999,591 A | 12/1999 | Kobayashi et al. |
| 6,011,580 A | 1/2000 | Hattori et al. |
| 6,011,809 A | 1/2000 | Tosaka |
| 6,019,507 A | 2/2000 | Takaki |
| 6,019,737 A | 2/2000 | Murata |
| 6,033,383 A | 3/2000 | Ginsburg |
| 6,036,682 A | 3/2000 | Lange et al. |
| 6,052,613 A | 4/2000 | Takaki |
| 6,064,684 A | 5/2000 | Yoon et al. |
| 6,069,698 A | 5/2000 | Ozawa et al. |
| 6,115,058 A | 9/2000 | Omori et al. |
| 6,134,003 A | 10/2000 | Tearney et al. |
| 6,160,826 A | 12/2000 | Swanson et al. |
| 6,165,127 A | 12/2000 | Crowley |
| 6,191,862 B1 | 2/2001 | Swanson et al. |
| 6,208,887 B1 | 3/2001 | Clarke |
| 6,217,828 B1 | 4/2001 | Bretscher et al. |
| 6,283,632 B1 | 9/2001 | Takaki |
| 6,296,608 B1 | 10/2001 | Daniels et al. |
| 6,309,358 B1 | 10/2001 | Okubo |
| 6,341,036 B1 | 1/2002 | Tearney et al. |
| 6,364,841 B1 | 4/2002 | White et al. |
| 6,383,209 B1 | 5/2002 | Crowley |
| 6,445,939 B1 | 9/2002 | Swanson et al. |
| 6,449,500 B1 | 9/2002 | Asai et al. |
| 6,471,656 B1 | 10/2002 | Shalman et al. |
| 6,485,413 B1 | 11/2002 | Boppart et al. |
| 6,485,482 B1 | 11/2002 | Belef |
| 6,520,959 B1 | 2/2003 | Iwahashi et al. |
| 6,530,921 B1 | 3/2003 | Maki |
| 6,547,757 B1 | 4/2003 | Kranz et al. |
| 6,549,687 B1 | 4/2003 | Kochergin et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,570,893 B1 | 5/2003 | Libatique et al. |
| 6,572,553 B2 | 6/2003 | Crowley |
| 6,577,391 B1 | 6/2003 | Faupel et al. |
| 6,579,286 B1 | 6/2003 | Maki et al. |
| 6,589,233 B1 | 7/2003 | Maki |
| 6,601,459 B1 | 8/2003 | Jenni |
| 6,607,526 B1 | 8/2003 | Maki |
| 6,615,072 B1 | 9/2003 | Izatt et al. |
| 6,654,630 B2 | 11/2003 | Zuluaga et al. |
| 6,658,278 B2 | 12/2003 | Gruhl |
| 6,879,851 B2 | 4/2005 | McNamara et al. |
| 6,881,194 B2 | 4/2005 | Miyata et al. |
| 6,891,984 B2 | 5/2005 | Petersen et al. |
| 6,904,197 B2 | 6/2005 | Bhagavatula et al. |
| 6,904,199 B2 | 6/2005 | Zuluaga |
| 6,925,320 B2 | 8/2005 | Gruhl |
| 6,940,885 B1 | 9/2005 | Cheng et al. |
| 7,003,184 B2 | 2/2006 | Ronnekleiv et al. |
| 7,016,024 B2 | 3/2006 | Bridge et al. |
| 7,022,118 B2 | 4/2006 | Ariura et al. |
| 7,029,436 B2 | 4/2006 | Iizuka et al. |
| 7,099,358 B1 | 8/2006 | Chong |
| 7,134,994 B2 | 11/2006 | Alpert et al. |
| 7,155,272 B2 | 12/2006 | Yamaguchi et al. |
| 7,180,600 B2 | 2/2007 | Horii et al. |
| 7,231,243 B2 | 6/2007 | Tearney et al. |
| 7,241,286 B2 | 7/2007 | Atlas |
| 7,365,859 B2 | 4/2008 | Yun et al. |
| 7,366,376 B2 | 4/2008 | Shishkov et al. |
| 7,382,949 B2 | 6/2008 | Bouma et al. |
| 7,450,980 B2 | 11/2008 | Kawanishi |
| 7,551,293 B2 | 6/2009 | Yelin et al. |
| 7,567,349 B2 | 7/2009 | Tearney et al. |
| 7,625,366 B2 | 12/2009 | Atlas |
| 7,682,089 B2 | 3/2010 | Rohlen |
| 7,691,061 B2 | 4/2010 | Hirota |
| 7,711,413 B2 | 5/2010 | Feldman et al. |
| 7,724,786 B2 | 5/2010 | Bouma et al. |
| 7,733,497 B2 | 6/2010 | Yun et al. |
| 7,738,941 B2 | 6/2010 | Hirota |
| 7,740,408 B2 | 6/2010 | Irisawa |
| 7,742,173 B2 | 6/2010 | Yun et al. |
| 7,761,139 B2 | 7/2010 | Tearney et al. |
| 7,783,337 B2 | 8/2010 | Feldman et al. |
| 7,794,230 B2 | 9/2010 | Lakin et al. |
| 7,803,141 B2 | 9/2010 | Epstein et al. |
| 7,812,961 B2 | 10/2010 | Yamaguchi |
| 7,813,609 B2 | 10/2010 | Petersen et al. |
| 7,815,632 B2 | 10/2010 | Hayakawa et al. |
| 7,843,572 B2 | 11/2010 | Tearney et al. |

(56) References Cited

U.S. PATENT DOCUMENTS

| | | |
|---|---|---|
| 7,847,949 B2 | 12/2010 | Tearney et al. |
| 7,848,791 B2 | 12/2010 | Schmitt et al. |
| 7,872,759 B2 | 1/2011 | Tearney et al. |
| 7,905,838 B2 | 3/2011 | Hirota |
| 7,911,621 B2 | 3/2011 | Motaghiannezam et al. |
| 7,916,387 B2 | 3/2011 | Schmitt |
| 7,920,271 B2 | 4/2011 | Vakoc et al. |
| 7,922,650 B2 | 4/2011 | McWeeney et al. |
| 7,926,562 B2 | 4/2011 | Poitzsch et al. |
| 7,935,060 B2 | 5/2011 | Schmitt et al. |
| 7,940,397 B2 | 5/2011 | Masuda |
| 7,952,718 B2 | 5/2011 | Li et al. |
| 7,969,578 B2 | 6/2011 | Yun et al. |
| 7,982,879 B2 | 7/2011 | Desjardins et al. |
| 8,018,598 B2 | 9/2011 | Cense et al. |
| 8,029,446 B2 | 10/2011 | Horiike et al. |
| 8,029,447 B2 | 10/2011 | Kanz et al. |
| 8,032,200 B2 | 10/2011 | Tearney et al. |
| 8,040,524 B2 | 10/2011 | Ozawa |
| 8,047,996 B2 | 11/2011 | Goodnow et al. |
| 8,049,900 B2 | 11/2011 | Kemp et al. |
| 8,052,605 B2 | 11/2011 | Muller et al. |
| 8,055,107 B2 | 11/2011 | Masuda |
| 8,081,316 B2 | 12/2011 | De Boer et al. |
| 8,094,319 B2 | 1/2012 | Onimura |
| 8,100,833 B2 | 1/2012 | Hirota |
| 8,108,032 B2 | 1/2012 | Onimura et al. |
| 8,116,605 B2 | 2/2012 | Petersen et al. |
| 8,125,648 B2 | 2/2012 | Milner et al. |
| 8,149,418 B2 | 4/2012 | Tearney et al. |
| 8,157,741 B2 | 4/2012 | Hirota |
| 8,157,742 B2 | 4/2012 | Taylor |
| 8,174,702 B2 | 5/2012 | Tearney et al. |
| 8,206,372 B2 | 6/2012 | Larson et al. |
| 8,206,377 B2 | 6/2012 | Petroff |
| 8,208,995 B2 | 6/2012 | Tearney et al. |
| 8,231,516 B2 | 7/2012 | Maschke |
| 8,241,196 B2 | 8/2012 | Scibona |
| 8,289,522 B2 | 10/2012 | Tearney et al. |
| RE43,875 E | 12/2012 | Shishkov et al. |
| 8,322,932 B2 | 12/2012 | Irisawa |
| 8,325,419 B2 | 12/2012 | Schmitt |
| 8,337,379 B2 | 12/2012 | Fletcher et al. |
| 8,339,592 B2 | 12/2012 | Hlavinka et al. |
| 8,346,348 B2 | 1/2013 | Onimura |
| 8,351,665 B2 | 1/2013 | Tearney et al. |
| 8,355,138 B2 | 1/2013 | Yun et al. |
| 8,384,907 B2 | 2/2013 | Tearney et al. |
| 8,384,909 B2 | 2/2013 | Yun et al. |
| 8,412,312 B2 | 4/2013 | Judell et al. |
| 8,414,496 B2 | 4/2013 | Goodnow et al. |
| 8,449,439 B2 | 5/2013 | Fletcher et al. |
| 8,449,468 B2 | 5/2013 | Petersen et al. |
| 8,452,371 B2 | 5/2013 | Feldman et al. |
| 8,473,037 B2 | 6/2013 | Irisawa |
| 8,473,073 B2 | 6/2013 | Vardiman |
| 8,478,384 B2 | 7/2013 | Schmitt et al. |
| 8,478,387 B2 | 7/2013 | Xu |
| 8,493,567 B2 | 7/2013 | Inoue |
| 8,501,015 B2 | 8/2013 | Fletcher et al. |
| 8,503,844 B2 | 8/2013 | Petersen et al. |
| 8,531,676 B2 | 9/2013 | Condit et al. |
| 8,535,210 B2 | 9/2013 | Kolenbrander et al. |
| 8,556,820 B2 | 10/2013 | Alpert et al. |
| 8,559,012 B2 | 10/2013 | Tearney et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,585,592 B2 | 11/2013 | Luevano et al. |
| 8,593,619 B2 | 11/2013 | Colice et al. |
| 8,593,641 B2 | 11/2013 | Kemp et al. |
| 8,618,032 B2 | 12/2013 | Kurita |
| 8,626,453 B2 | 1/2014 | Myoujou et al. |
| 8,636,659 B2 | 1/2014 | Alpert et al. |
| 8,676,013 B2 | 3/2014 | Bouma et al. |
| 8,676,299 B2 | 3/2014 | Schmitt et al. |
| 8,687,201 B2 | 4/2014 | Adler |
| 8,705,046 B2 | 4/2014 | Yun et al. |
| 8,712,506 B2 | 4/2014 | Courtney et al. |
| 8,753,281 B2 | 6/2014 | Schmitt et al. |
| 8,760,663 B2 | 6/2014 | Tearney et al. |
| 8,761,469 B2 | 6/2014 | Kemp et al. |
| 8,786,336 B1 | 7/2014 | Schmitt |
| 8,804,126 B2 | 8/2014 | Tearney et al. |
| 8,808,186 B2 | 8/2014 | Fruland et al. |
| 8,810,901 B2 | 8/2014 | Huber et al. |
| 8,825,142 B2 | 9/2014 | Suehara |
| 8,827,926 B2 | 9/2014 | Kinoshita et al. |
| 8,831,321 B1 | 9/2014 | Elbasiony |
| 8,868,159 B2 | 10/2014 | Onimura |
| 8,885,171 B2 | 11/2014 | Watanabe et al. |
| 8,896,838 B2 | 11/2014 | Tearney et al. |
| 8,902,941 B2 | 12/2014 | Schmitt |
| 8,909,324 B2 | 12/2014 | Furuichi |
| 8,911,357 B2 | 12/2014 | Omori |
| 8,926,590 B2 | 1/2015 | Petroff |
| 8,928,889 B2 | 1/2015 | Tearney et al. |
| 8,945,526 B2 | 2/2015 | Akitsu et al. |
| 8,948,228 B2 | 2/2015 | Adler |
| 8,948,613 B2 | 2/2015 | Schmitt et al. |
| 8,953,911 B1 | 2/2015 | Xu et al. |
| 8,983,582 B2 | 3/2015 | Webler |
| 8,989,849 B2 | 3/2015 | Milner et al. |
| 8,994,803 B2 | 3/2015 | Kaneko |
| 8,996,099 B2 | 3/2015 | Feldman et al. |
| 8,998,797 B2 | 4/2015 | Omori |
| 9,007,696 B2 | 4/2015 | Petersen et al. |
| 9,033,890 B2 | 5/2015 | Furuichi |
| 9,036,966 B2 | 5/2015 | Bhagavatula et al. |
| 9,039,626 B2 | 5/2015 | Courtney |
| 9,060,689 B2 | 6/2015 | Tearney et al. |
| 9,069,396 B2 | 6/2015 | Adler et al. |
| 9,081,148 B2 | 7/2015 | Tearney et al. |
| 9,084,532 B2 | 7/2015 | Horiike |
| 9,087,368 B2 | 7/2015 | Tearney et al. |
| 9,091,524 B2 | 7/2015 | Adler et al. |
| 9,101,298 B2 | 8/2015 | Hossack et al. |
| 9,107,682 B2 | 8/2015 | Scheller et al. |
| 9,107,687 B2 | 8/2015 | Kinoshita et al. |
| 9,121,926 B2 | 9/2015 | Nair et al. |
| 9,131,850 B2 | 9/2015 | Liu et al. |
| 9,138,147 B2 | 9/2015 | Schmitt et al. |
| 9,164,240 B2 | 10/2015 | Schmitt et al. |
| 9,168,003 B2 | 10/2015 | Suzuki et al. |
| 9,173,572 B2 | 11/2015 | Colice et al. |
| 9,173,591 B2 | 11/2015 | Elbasiony et al. |
| 9,194,690 B2 | 11/2015 | Bhagavatula et al. |
| 9,207,064 B2 | 12/2015 | Inoue |
| 9,226,660 B2 | 1/2016 | De Boer et al. |
| 9,226,665 B2 | 1/2016 | Tearney et al. |
| 9,254,102 B2 | 2/2016 | Tearney et al. |
| 9,289,127 B2 | 3/2016 | Mitsuhashi et al. |
| 9,289,582 B2 | 3/2016 | Suehara |
| 9,295,450 B2 | 3/2016 | Furuichi et al. |
| 9,295,455 B2 | 3/2016 | Karino et al. |
| 9,301,687 B2 | 4/2016 | Kemp |
| 9,304,121 B2 | 4/2016 | Tearney et al. |
| 9,322,639 B2 | 4/2016 | Watanabe et al. |
| 9,326,789 B2 | 5/2016 | Fruland et al. |
| 9,330,092 B2 | 5/2016 | Vakoc et al. |
| 9,339,173 B2 | 5/2016 | McWeeney et al. |
| 9,339,348 B2 | 5/2016 | Davies et al. |
| 9,345,864 B2 | 5/2016 | Suehara |
| 9,347,765 B2 | 5/2016 | Kemp et al. |
| 9,351,698 B2 | 5/2016 | Dascal et al. |
| 9,357,923 B2 | 6/2016 | Courtney et al. |
| 9,375,148 B2 | 6/2016 | Senoo |
| 9,375,158 B2 | 6/2016 | Vakoc et al. |
| 9,375,164 B2 | 6/2016 | Tolkowsky et al. |
| 9,377,290 B2 | 6/2016 | Yun et al. |
| 9,404,731 B2 | 8/2016 | Adler et al. |
| 9,408,539 B2 | 8/2016 | Tearney et al. |
| 9,417,052 B2 | 8/2016 | Adler |

(56) References Cited

U.S. PATENT DOCUMENTS

| | | |
|---|---|---|
| 9,435,736 B2 | 9/2016 | Kolenbrander et al. |
| 9,435,956 B1 | 9/2016 | Ku et al. |
| 9,439,570 B2 | 9/2016 | Vertikov |
| 9,441,948 B2 | 9/2016 | Vakoc et al. |
| 9,462,950 B2 | 10/2016 | Xu |
| 9,464,883 B2 | 10/2016 | Swanson et al. |
| 9,488,464 B1 | 11/2016 | Schmitt |
| 9,507,074 B2 | 11/2016 | Zhu et al. |
| 9,513,276 B2 | 12/2016 | Tearney et al. |
| 9,526,424 B2 | 12/2016 | Judell et al. |
| 9,566,752 B2 | 2/2017 | Hartkorn |
| 9,572,495 B2 | 2/2017 | Schmitt et al. |
| 9,572,496 B2 | 2/2017 | Furuichi et al. |
| 9,605,942 B2 | 3/2017 | Staloff |
| 9,610,064 B2 | 4/2017 | Adler et al. |
| 9,615,771 B2 | 4/2017 | Furuichi et al. |
| 9,622,706 B2 | 4/2017 | Dick et al. |
| 9,638,862 B2 | 5/2017 | Bhagavatula et al. |
| 9,642,531 B2 | 5/2017 | Tearney et al. |
| 9,645,322 B2 | 5/2017 | Murashima et al. |
| 9,646,377 B2 | 5/2017 | Tearney et al. |
| 9,659,375 B2 | 5/2017 | Zagrodsky et al. |
| 9,702,687 B2 | 7/2017 | Schmitt |
| 9,702,762 B2 | 7/2017 | Friedman et al. |
| 9,704,240 B2 | 7/2017 | Lam et al. |
| 9,710,891 B2 | 7/2017 | Sakamoto |
| 9,730,613 B2 | 8/2017 | Stigall et al. |
| 9,763,623 B2 | 9/2017 | Tearney et al. |
| 9,778,020 B2 | 10/2017 | Tumlinson et al. |
| 9,788,790 B2 | 10/2017 | Black et al. |
| 9,808,303 B2 | 11/2017 | Ryba et al. |
| 9,812,846 B2 | 11/2017 | Yun et al. |
| 9,833,221 B2 | 12/2017 | Hutchins et al. |
| 9,836,835 B2 | 12/2017 | Furuichi et al. |
| 9,843,159 B2 | 12/2017 | Cable et al. |
| 9,855,020 B2 | 1/2018 | Nair et al. |
| 9,858,387 B2 | 1/2018 | Lavi et al. |
| 9,864,140 B2 | 1/2018 | Adler et al. |
| 9,872,665 B2 | 1/2018 | Okubo et al. |
| 9,891,044 B2 | 2/2018 | Tu et al. |
| 9,897,538 B2 | 2/2018 | Tearney et al. |
| 9,907,527 B2 | 3/2018 | Dascal et al. |
| 9,933,244 B2 | 4/2018 | Krol et al. |
| 9,940,723 B2 | 4/2018 | Gopinath et al. |
| 9,943,233 B2 | 4/2018 | Lavi et al. |
| 9,962,127 B2 | 5/2018 | Wang et al. |
| 9,980,648 B2 | 5/2018 | Itoh et al. |
| 9,983,356 B2 | 5/2018 | Schmitt et al. |
| 9,986,938 B2 | 6/2018 | Tu et al. |
| 9,989,945 B2 | 6/2018 | Adler et al. |
| 9,996,921 B2 | 6/2018 | Ambwani et al. |
| 10,004,400 B2 | 6/2018 | Nakamoto et al. |
| 10,004,863 B2 | 6/2018 | Vazales et al. |
| 10,006,753 B2 | 6/2018 | Schmitt et al. |
| 10,028,725 B2 | 7/2018 | Petroff |
| 10,089,755 B2 | 10/2018 | Griffin et al. |
| 10,092,188 B2 | 10/2018 | Jaffer et al. |
| 10,109,058 B2 | 10/2018 | Ambwani et al. |
| 10,124,153 B2 | 11/2018 | Feig et al. |
| 10,140,712 B2 | 11/2018 | Ambwani |
| 10,162,114 B2 | 12/2018 | Bhagavatula et al. |
| 10,172,582 B2 | 1/2019 | Dascal et al. |
| 10,186,056 B2 | 1/2019 | Senzig et al. |
| 10,207,124 B2 | 2/2019 | Shimizu et al. |
| 10,213,109 B2 | 2/2019 | Itoh et al. |
| 10,213,186 B2 | 2/2019 | Inoue et al. |
| 10,219,780 B2 | 3/2019 | Castella et al. |
| 10,222,956 B2 | 3/2019 | Gopinath et al. |
| 10,238,349 B2 | 3/2019 | Furuichi et al. |
| 10,261,223 B2 | 4/2019 | Tearney et al. |
| 10,271,818 B2 | 4/2019 | Kobayashi |
| 10,285,568 B2 | 5/2019 | Tearney et al. |
| 10,327,726 B2 | 6/2019 | Dascal et al. |
| 10,331,099 B2 | 6/2019 | Adler et al. |
| 10,335,039 B2 | 7/2019 | Xu |
| 10,338,795 B2 | 7/2019 | Gopinath et al. |
| 10,342,502 B2 | 7/2019 | Dascal et al. |
| 10,387,013 B2 | 8/2019 | Jamello |
| 10,453,190 B2 | 10/2019 | Griffin |
| 10,453,191 B2 | 10/2019 | Shalev et al. |
| 10,453,196 B2 | 10/2019 | Ambwani |
| 10,463,254 B2 | 11/2019 | Tearney et al. |
| 10,499,813 B2 | 12/2019 | Adler |
| 10,529,093 B2 | 1/2020 | Griffin et al. |
| 10,551,251 B2 | 2/2020 | Friedman et al. |
| 10,593,037 B2 | 3/2020 | Gopinath |
| 10,631,754 B2 | 4/2020 | Gopinath |
| 10,646,198 B2 | 5/2020 | Peterson et al. |
| 10,648,918 B2 | 5/2020 | Schmitt |
| 10,687,777 B2 | 6/2020 | Dascal et al. |
| 10,713,786 B2 | 7/2020 | Ambwani et al. |
| 10,729,376 B2 | 8/2020 | Courtney |
| 10,792,012 B2 | 10/2020 | Hutchins et al. |
| 10,878,572 B2 | 12/2020 | Gopinath et al. |
| 10,902,599 B2 | 1/2021 | Ambwani et al. |
| 2002/0041724 A1 | 4/2002 | Ronnekleiv et al. |
| 2002/0072880 A1 | 6/2002 | Svanerudh et al. |
| 2002/0099289 A1 | 7/2002 | Crowley |
| 2002/0131049 A1 | 9/2002 | Schmitt |
| 2002/0151823 A1 | 10/2002 | Miyata et al. |
| 2002/0163622 A1 | 11/2002 | Magnin et al. |
| 2002/0183601 A1 | 12/2002 | Tearney et al. |
| 2002/0183622 A1 | 12/2002 | Zuluaga et al. |
| 2002/0188204 A1 | 12/2002 | McNamara et al. |
| 2002/0198457 A1 | 12/2002 | Tearney et al. |
| 2003/0004417 A1 | 1/2003 | Ariura et al. |
| 2003/0013952 A1 | 1/2003 | Iizuka et al. |
| 2003/0073909 A1 | 4/2003 | Gruhl |
| 2003/0081875 A1 | 5/2003 | Kochergin et al. |
| 2003/0165291 A1 | 9/2003 | Bhagavatula et al. |
| 2003/0216621 A1 | 11/2003 | Alpert et al. |
| 2004/0017961 A1 | 1/2004 | Petersen et al. |
| 2004/0034290 A1 | 2/2004 | Zuluaga |
| 2004/0082861 A1 | 4/2004 | Gruhl |
| 2004/0092913 A1 | 5/2004 | Hennings et al. |
| 2004/0215166 A1 | 10/2004 | Atlas |
| 2005/0004453 A1 | 1/2005 | Tearney et al. |
| 2005/0038406 A1 | 2/2005 | Epstein et al. |
| 2005/0101870 A1 | 5/2005 | Yamaguchi et al. |
| 2005/0128488 A1 | 6/2005 | Yelin et al. |
| 2005/0168751 A1 | 8/2005 | Horii et al. |
| 2005/0187422 A1 | 8/2005 | Maschke |
| 2005/0201662 A1 | 9/2005 | Petersen et al. |
| 2005/0221277 A1 | 10/2005 | Kawanishi |
| 2005/0259242 A1 | 11/2005 | Bridge et al. |
| 2005/0272975 A1 | 12/2005 | McWeeney et al. |
| 2005/0288583 A1 | 12/2005 | Hirota |
| 2006/0039004 A1 | 2/2006 | De Boer et al. |
| 2006/0055936 A1 | 3/2006 | Yun et al. |
| 2006/0058622 A1 | 3/2006 | Tearney et al. |
| 2006/0067620 A1 | 3/2006 | Shishkov et al. |
| 2006/0091566 A1 | 5/2006 | Yang et al. |
| 2006/0093276 A1 | 5/2006 | Bouma et al. |
| 2006/0095065 A1 | 5/2006 | Tanimura et al. |
| 2006/0135870 A1 | 6/2006 | Webler |
| 2006/0166176 A1 | 7/2006 | Lakin et al. |
| 2006/0227333 A1 | 10/2006 | Tearney et al. |
| 2006/0241484 A1 | 10/2006 | Horiike et al. |
| 2006/0241493 A1 | 10/2006 | Feldman et al. |
| 2006/0241503 A1 | 10/2006 | Schmitt et al. |
| 2006/0244973 A1 | 11/2006 | Yun et al. |
| 2006/0247743 A1 | 11/2006 | Hayakawa et al. |
| 2006/0279742 A1 | 12/2006 | Tearney et al. |
| 2007/0012886 A1 | 1/2007 | Tearney et al. |
| 2007/0015969 A1 | 1/2007 | Feldman et al. |
| 2007/0035743 A1 | 2/2007 | Vakoc et al. |
| 2007/0038040 A1 | 2/2007 | Cense et al. |
| 2007/0038274 A1 | 2/2007 | Ishii et al. |
| 2007/0060822 A1 | 3/2007 | Alpert et al. |
| 2007/0073162 A1 | 3/2007 | Tearney et al. |
| 2007/0081236 A1 | 4/2007 | Tearney et al. |
| 2007/0106155 A1 | 5/2007 | Goodnow et al. |
| 2007/0121196 A1 | 5/2007 | Tearney et al. |
| 2007/0201033 A1 | 8/2007 | Desjardins et al. |

(56) References Cited

U.S. PATENT DOCUMENTS

| | | |
|---|---|---|
| 2007/0229801 A1 | 10/2007 | Tearney et al. |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0233396 A1 | 10/2007 | Tearney et al. |
| 2007/0236700 A1 | 10/2007 | Yun et al. |
| 2007/0244391 A1 | 10/2007 | Hirota |
| 2007/0260198 A1 | 11/2007 | Atlas |
| 2008/0002211 A1 | 1/2008 | Park et al. |
| 2008/0004530 A1 | 1/2008 | Feldman et al. |
| 2008/0007734 A1 | 1/2008 | Park et al. |
| 2008/0019908 A1 | 1/2008 | Akitsu et al. |
| 2008/0021275 A1 | 1/2008 | Tearney et al. |
| 2008/0045394 A1 | 2/2008 | Fletcher et al. |
| 2008/0049232 A1 | 2/2008 | Vakoc et al. |
| 2008/0161696 A1 | 7/2008 | Schmitt et al. |
| 2008/0165366 A1 | 7/2008 | Schmitt |
| 2008/0177139 A1 | 7/2008 | Courtney et al. |
| 2008/0181263 A1 | 7/2008 | Bouma et al. |
| 2008/0208227 A1 | 8/2008 | Kadykowski et al. |
| 2008/0225301 A1 | 9/2008 | Yamaguchi |
| 2008/0262346 A1 | 10/2008 | Assis et al. |
| 2008/0269572 A1 | 10/2008 | Kanz et al. |
| 2008/0291463 A1 | 11/2008 | Milner et al. |
| 2008/0297806 A1 | 12/2008 | Motaghiannezam et al. |
| 2009/0018393 A1 | 1/2009 | Dick et al. |
| 2009/0027689 A1 | 1/2009 | Yun et al. |
| 2009/0036782 A1 | 2/2009 | Vakoc et al. |
| 2009/0043191 A1 | 2/2009 | Castella et al. |
| 2009/0046295 A1 | 2/2009 | Kemp et al. |
| 2009/0046980 A1 | 2/2009 | Rohlen |
| 2009/0073454 A1 | 3/2009 | Ozawa |
| 2009/0073455 A1 | 3/2009 | Onimura |
| 2009/0093980 A1 | 4/2009 | Kemp et al. |
| 2009/0122320 A1 | 5/2009 | Petersen et al. |
| 2009/0131801 A1 | 5/2009 | Suter et al. |
| 2009/0135429 A1 | 5/2009 | Masuda |
| 2009/0143686 A1 | 6/2009 | Onimura et al. |
| 2009/0182246 A1 | 7/2009 | Kinoshita et al. |
| 2009/0192519 A1 | 7/2009 | Omori |
| 2009/0196477 A1 | 8/2009 | Cense et al. |
| 2009/0196554 A1 | 8/2009 | Irisawa |
| 2009/0251704 A1 | 10/2009 | Masuda |
| 2009/0261240 A1 | 10/2009 | Watanabe et al. |
| 2009/0262361 A1 | 10/2009 | Tanioka et al. |
| 2009/0283258 A1 | 11/2009 | Poitzsch et al. |
| 2009/0299195 A1* | 12/2009 | Muller ................ A61B 5/0062 600/478 |
| 2009/0306520 A1 | 12/2009 | Schmitt et al. |
| 2009/0323076 A1 | 12/2009 | Li et al. |
| 2010/0019189 A1 | 1/2010 | Kurita |
| 2010/0042084 A1 | 2/2010 | Nariyuki et al. |
| 2010/0073682 A1 | 3/2010 | Inoue |
| 2010/0076320 A1 | 3/2010 | Petersen et al. |
| 2010/0094127 A1 | 4/2010 | Xu |
| 2010/0110414 A1 | 5/2010 | Colice et al. |
| 2010/0130872 A1 | 5/2010 | Irisawa |
| 2010/0157309 A1 | 6/2010 | Tearney et al. |
| 2010/0158339 A1 | 6/2010 | Omori |
| 2010/0160134 A1 | 6/2010 | Scibona |
| 2010/0160780 A1 | 6/2010 | Swan et al. |
| 2010/0168587 A1 | 7/2010 | Feldman et al. |
| 2010/0220334 A1 | 9/2010 | Condit et al. |
| 2010/0241154 A1 | 9/2010 | Larson et al. |
| 2010/0249588 A1 | 9/2010 | Knight |
| 2010/0249601 A1 | 9/2010 | Courtney |
| 2010/0253949 A1 | 10/2010 | Adler et al. |
| 2010/0298908 A1 | 11/2010 | Vardiman |
| 2010/0305452 A1 | 12/2010 | Black et al. |
| 2010/0309477 A1 | 12/2010 | Yun et al. |
| 2011/0007315 A1 | 1/2011 | Petersen et al. |
| 2011/0009741 A1 | 1/2011 | Matthews et al. |
| 2011/0019182 A1 | 1/2011 | Hlavinka et al. |
| 2011/0058178 A1 | 3/2011 | Tearney et al. |
| 2011/0071404 A1 | 3/2011 | Schmitt et al. |
| 2011/0071405 A1 | 3/2011 | Judell et al. |
| 2011/0092823 A1 | 4/2011 | Tearney et al. |
| 2011/0101207 A1 | 5/2011 | Schmitt |
| 2011/0143905 A1 | 6/2011 | Kolenbrander et al. |
| 2011/0144504 A1 | 6/2011 | Tearney et al. |
| 2011/0149296 A1 | 6/2011 | Tearney et al. |
| 2011/0151980 A1 | 6/2011 | Petroff |
| 2011/0152771 A1 | 6/2011 | Milner et al. |
| 2011/0157686 A1 | 6/2011 | Huber et al. |
| 2011/0172511 A1 | 7/2011 | Petersen et al. |
| 2011/0178398 A1 | 7/2011 | Tearney et al. |
| 2011/0178413 A1 | 7/2011 | Schmitt et al. |
| 2011/0196217 A1 | 8/2011 | Myoujou et al. |
| 2011/0201924 A1 | 8/2011 | Tearney et al. |
| 2011/0216325 A1 | 9/2011 | Schmitt |
| 2011/0218403 A1 | 9/2011 | Tearney et al. |
| 2011/0224541 A1 | 9/2011 | Yun et al. |
| 2011/0228280 A1 | 9/2011 | Schmitt et al. |
| 2011/0237958 A1 | 9/2011 | Onimura |
| 2011/0245683 A1 | 10/2011 | Onimura |
| 2011/0245684 A1 | 10/2011 | Onimura |
| 2011/0261366 A1 | 10/2011 | Tearney et al. |
| 2011/0267340 A1 | 11/2011 | Kraus et al. |
| 2011/0270091 A1 | 11/2011 | Hossack et al. |
| 2011/0292400 A1 | 12/2011 | Fleming et al. |
| 2011/0299091 A1 | 12/2011 | Yun et al. |
| 2012/0002928 A1 | 1/2012 | Irisawa |
| 2012/0004506 A1 | 1/2012 | Tearney et al. |
| 2012/0007974 A1 | 1/2012 | Kaneko |
| 2012/0008146 A1 | 1/2012 | Tearney et al. |
| 2012/0013914 A1 | 1/2012 | Kemp et al. |
| 2012/0022360 A1 | 1/2012 | Kemp |
| 2012/0035454 A1 | 2/2012 | Tearney et al. |
| 2012/0053918 A1 | 3/2012 | Taylor |
| 2012/0057157 A1 | 3/2012 | Petersen et al. |
| 2012/0063570 A1 | 3/2012 | Furuichi et al. |
| 2012/0065517 A1 | 3/2012 | Goodnow et al. |
| 2012/0071736 A1 | 3/2012 | Luevano et al. |
| 2012/0123352 A1 | 5/2012 | Fruland et al. |
| 2012/0127476 A1 | 5/2012 | De Boer et al. |
| 2012/0135384 A1 | 5/2012 | Nakao |
| 2012/0170848 A1 | 7/2012 | Kemp et al. |
| 2012/0190974 A1 | 7/2012 | Suehara |
| 2012/0215091 A1 | 8/2012 | Suzuki et al. |
| 2012/0220836 A1 | 8/2012 | Alpert et al. |
| 2012/0226151 A1 | 9/2012 | Irisawa |
| 2012/0236883 A1 | 9/2012 | Adler |
| 2012/0238869 A1 | 9/2012 | Schmitt et al. |
| 2012/0243761 A1 | 9/2012 | Senzig et al. |
| 2012/0245459 A1 | 9/2012 | Senoo |
| 2012/0250028 A1 | 10/2012 | Schmitt et al. |
| 2012/0253114 A1 | 10/2012 | Kinoshita et al. |
| 2012/0253123 A1 | 10/2012 | Shimizu et al. |
| 2012/0253184 A1 | 10/2012 | Furuichi et al. |
| 2012/0253185 A1 | 10/2012 | Furuichi |
| 2012/0281237 A1 | 11/2012 | Tearney et al. |
| 2012/0310081 A1 | 12/2012 | Adler et al. |
| 2012/0330101 A1 | 12/2012 | Brennan et al. |
| 2013/0002843 A1 | 1/2013 | Horiike |
| 2013/0006104 A1 | 1/2013 | Mitsuhashi et al. |
| 2013/0006105 A1 | 1/2013 | Furuichi |
| 2013/0010303 A1 | 1/2013 | Petersen et al. |
| 2013/0012810 A1 | 1/2013 | Nakamoto et al. |
| 2013/0012811 A1 | 1/2013 | Schmitt et al. |
| 2013/0023760 A1 | 1/2013 | Liu et al. |
| 2013/0023761 A1 | 1/2013 | Petroff |
| 2013/0046190 A1 | 2/2013 | Davies et al. |
| 2013/0051728 A1 | 2/2013 | Petroff et al. |
| 2013/0072367 A1 | 3/2013 | Fletcher et al. |
| 2013/0072805 A1 | 3/2013 | Schmitt et al. |
| 2013/0079630 A1 | 3/2013 | Horiike |
| 2013/0079631 A1 | 3/2013 | Horiike et al. |
| 2013/0100455 A1 | 4/2013 | Tearney et al. |
| 2013/0107043 A1 | 5/2013 | Fletcher et al. |
| 2013/0116671 A1 | 5/2013 | Scheller et al. |
| 2013/0128274 A1 | 5/2013 | Yun et al. |
| 2013/0148106 A1 | 6/2013 | Tearney et al. |
| 2013/0176571 A1 | 7/2013 | Tearney et al. |

(56) References Cited

U.S. PATENT DOCUMENTS

| | | |
|---|---|---|
| 2013/0185023 A1 | 7/2013 | Vakoc et al. |
| 2013/0188850 A1 | 7/2013 | Tearney et al. |
| 2013/0215427 A1 | 8/2013 | Bouma et al. |
| 2013/0217964 A1 | 8/2013 | Kumoyama et al. |
| 2013/0222813 A1 | 8/2013 | Watanabe et al. |
| 2013/0246034 A1 | 9/2013 | Sharma et al. |
| 2013/0266259 A1 | 10/2013 | Bhagavatula et al. |
| 2013/0278936 A1 | 10/2013 | Inoue |
| 2013/0281844 A1 | 10/2013 | Karino et al. |
| 2013/0303907 A1 | 11/2013 | Corl |
| 2013/0310698 A1 | 11/2013 | Judell et al. |
| 2013/0314716 A1 | 11/2013 | Tearney et al. |
| 2013/0331689 A1 | 12/2013 | Le et al. |
| 2014/0005023 A1 | 1/2014 | Kolenbrander et al. |
| 2014/0018669 A1 | 1/2014 | Xu |
| 2014/0024930 A1 | 1/2014 | Furuichi et al. |
| 2014/0024931 A1 | 1/2014 | Winston et al. |
| 2014/0031677 A1 | 1/2014 | Iftimia et al. |
| 2014/0031679 A1 | 1/2014 | Tashiro et al. |
| 2014/0036941 A1 | 2/2014 | Desmond |
| 2014/0063488 A1 | 3/2014 | Adler |
| 2014/0066706 A1 | 3/2014 | McWeeney et al. |
| 2014/0066756 A1 | 3/2014 | Sinclair et al. |
| 2014/0083970 A1 | 3/2014 | Kumar et al. |
| 2014/0088411 A1 | 3/2014 | Suehara et al. |
| 2014/0094697 A1 | 4/2014 | Petroff et al. |
| 2014/0100451 A1 | 4/2014 | Tolkowsky et al. |
| 2014/0114182 A1 | 4/2014 | Petersen et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0150782 A1 | 6/2014 | Vazales et al. |
| 2014/0177935 A1 | 6/2014 | Nair et al. |
| 2014/0180071 A1 | 6/2014 | Stigall et al. |
| 2014/0187929 A1 | 7/2014 | Schmitt et al. |
| 2014/0200867 A1 | 7/2014 | Lavi et al. |
| 2014/0206989 A1 | 7/2014 | Colice et al. |
| 2014/0207168 A1 | 7/2014 | Kawaura et al. |
| 2014/0218742 A1 | 8/2014 | Adler |
| 2014/0243876 A1 | 8/2014 | Suehara |
| 2014/0247454 A1 | 9/2014 | Bhagavatula et al. |
| 2014/0249407 A1 | 9/2014 | Adler et al. |
| 2014/0257087 A1 | 9/2014 | Elbasiony et al. |
| 2014/0267038 A1 | 9/2014 | Adler et al. |
| 2014/0268167 A1 | 9/2014 | Friedman et al. |
| 2014/0270436 A1 | 9/2014 | Dascal et al. |
| 2014/0270445 A1 | 9/2014 | Kemp |
| 2014/0276020 A1 | 9/2014 | Hutchins et al. |
| 2014/0276108 A1 | 9/2014 | Vertikov |
| 2014/0277072 A1 | 9/2014 | Suehara |
| 2014/0301620 A1 | 10/2014 | Tearney et al. |
| 2014/0323877 A1 | 10/2014 | Courtney et al. |
| 2014/0346693 A1 | 11/2014 | Hartkorn |
| 2014/0371598 A1 | 12/2014 | Okubo et al. |
| 2014/0376000 A1 | 12/2014 | Swanson et al. |
| 2014/0378845 A1 | 12/2014 | Nadkarni |
| 2014/0379269 A1 | 12/2014 | Schmitt |
| 2015/0005615 A1 | 1/2015 | Inoue et al. |
| 2015/0005626 A1 | 1/2015 | Kaneko |
| 2015/0005627 A1 | 1/2015 | Itoh et al. |
| 2015/0005628 A1 | 1/2015 | Itoh et al. |
| 2015/0025369 A1 | 1/2015 | Bhagavatula et al. |
| 2015/0029513 A1 | 1/2015 | Tearney et al. |
| 2015/0036146 A1 | 2/2015 | Staloff |
| 2015/0049339 A1 | 2/2015 | Tearney et al. |
| 2015/0051485 A1 | 2/2015 | Itoh et al. |
| 2015/0057958 A1 | 2/2015 | Watanabe et al. |
| 2015/0077755 A1 | 3/2015 | Yun et al. |
| 2015/0080700 A1 | 3/2015 | Fruland et al. |
| 2015/0099968 A1 | 4/2015 | Jamello |
| 2015/0099975 A1 | 4/2015 | Lam et al. |
| 2015/0119707 A1 | 4/2015 | Petroff |
| 2015/0133773 A1 | 5/2015 | Jaffer et al. |
| 2015/0133776 A1 | 5/2015 | Hoffman |
| 2015/0133789 A1 | 5/2015 | Ariura et al. |
| 2015/0153157 A1 | 6/2015 | Schmitt et al. |
| 2015/0164331 A1* | 6/2015 | Burgess ............... A61B 8/12 601/3 |
| 2015/0164423 A1 | 6/2015 | Webler |
| 2015/0182192 A1 | 7/2015 | Kaneko |
| 2015/0190054 A1 | 7/2015 | Kaneko |
| 2015/0192405 A1 | 7/2015 | Schmitt |
| 2015/0196285 A1 | 7/2015 | Mori |
| 2015/0216415 A1 | 8/2015 | Uribe-Patarroyo et al. |
| 2015/0219854 A1 | 8/2015 | Bhagavatula et al. |
| 2015/0230775 A1 | 8/2015 | Kobayashi |
| 2015/0238084 A1 | 8/2015 | Tearney et al. |
| 2015/0238121 A1 | 8/2015 | Tu et al. |
| 2015/0245768 A1 | 9/2015 | Hasegawa et al. |
| 2015/0257704 A1 | 9/2015 | Courtney |
| 2015/0257850 A1 | 9/2015 | Sakamoto |
| 2015/0265152 A1 | 9/2015 | Feldman et al. |
| 2015/0265162 A1 | 9/2015 | Lavi et al. |
| 2015/0268039 A1 | 9/2015 | Tu et al. |
| 2015/0282737 A1 | 10/2015 | Tolkowsky et al. |
| 2015/0297097 A1* | 10/2015 | Matsubara ............ A61B 8/085 600/407 |
| 2015/0297373 A1 | 10/2015 | Schmitt et al. |
| 2015/0306361 A1 | 10/2015 | Feig et al. |
| 2015/0320317 A1 | 11/2015 | Furuichi et al. |
| 2015/0366534 A1 | 12/2015 | Nair et al. |
| 2015/0370229 A1 | 12/2015 | Adler et al. |
| 2015/0371382 A1 | 12/2015 | Furuichi et al. |
| 2016/0000406 A1 | 1/2016 | Petroff |
| 2016/0007838 A1 | 1/2016 | Ariura et al. |
| 2016/0008090 A1 | 1/2016 | Yokoi et al. |
| 2016/0015337 A1 | 1/2016 | Inoue et al. |
| 2016/0018211 A1 | 1/2016 | Adler et al. |
| 2016/0022208 A1 | 1/2016 | Gopinath |
| 2016/0022248 A1 | 1/2016 | Mori et al. |
| 2016/0070066 A1 | 3/2016 | Schmitt et al. |
| 2016/0073885 A1 | 3/2016 | Adler |
| 2016/0089203 A1 | 3/2016 | Shimizu et al. |
| 2016/0089547 A1 | 3/2016 | Shimizu et al. |
| 2016/0092749 A1 | 3/2016 | Sakamoto |
| 2016/0093049 A1 | 3/2016 | Kobayashi |
| 2016/0095577 A1 | 4/2016 | Itoh et al. |
| 2016/0120408 A1 | 5/2016 | Bhagavatula et al. |
| 2016/0120492 A1 | 5/2016 | Honma et al. |
| 2016/0124134 A1 | 5/2016 | Zhu et al. |
| 2016/0157803 A1* | 6/2016 | Keller ................ A61B 8/12 600/467 |
| 2016/0166815 A1 | 6/2016 | Suehara |
| 2016/0171701 A1 | 6/2016 | Zagrodsky et al. |
| 2016/0171711 A1 | 6/2016 | Gopinath et al. |
| 2016/0174925 A1 | 6/2016 | Dascal et al. |
| 2016/0199017 A1 | 7/2016 | Shimizu et al. |
| 2016/0202417 A1 | 7/2016 | Bhagavatula et al. |
| 2016/0206208 A1 | 7/2016 | Yamamoto et al. |
| 2016/0206267 A1 | 7/2016 | Shimizu et al. |
| 2016/0206290 A1 | 7/2016 | Itoh et al. |
| 2016/0228071 A1 | 8/2016 | Wang et al. |
| 2016/0270766 A1 | 9/2016 | Kobayashi |
| 2016/0301189 A1 | 10/2016 | Cable et al. |
| 2016/0313507 A1 | 10/2016 | Adler et al. |
| 2016/0320170 A1 | 11/2016 | Yun et al. |
| 2016/0320564 A1 | 11/2016 | Murashima et al. |
| 2016/0335763 A1 | 11/2016 | Ambwani et al. |
| 2016/0335766 A1 | 11/2016 | Ambwani et al. |
| 2016/0338753 A1 | 11/2016 | Ryba et al. |
| 2016/0341538 A1 | 11/2016 | Tumlinson et al. |
| 2016/0349417 A1 | 12/2016 | Tearney et al. |
| 2016/0370168 A1 | 12/2016 | Krol et al. |
| 2017/0014100 A1 | 1/2017 | Mori |
| 2017/0020392 A1 | 1/2017 | Xu |
| 2017/0024532 A1 | 1/2017 | Gopinath et al. |
| 2017/0024910 A1 | 1/2017 | Griffin et al. |
| 2017/0103520 A1 | 4/2017 | Gopinath et al. |
| 2017/0135663 A1 | 5/2017 | Dascal et al. |
| 2017/0140243 A1 | 5/2017 | Ambwani |
| 2017/0140531 A1 | 5/2017 | Dascal et al. |
| 2017/0140532 A1 | 5/2017 | Dascal et al. |
| 2017/0140560 A1 | 5/2017 | Kraus et al. |
| 2017/0143296 A1 | 5/2017 | Peterson et al. |

(56) References Cited

U.S. PATENT DOCUMENTS

| | | |
|---|---|---|
| 2017/0148161 A1 | 5/2017 | Griffin |
| 2017/0153439 A1 | 6/2017 | Horiike |
| 2017/0188831 A1 | 7/2017 | Adler et al. |
| 2017/0238809 A1 | 8/2017 | Tearney et al. |
| 2017/0261378 A1 | 9/2017 | Friedman et al. |
| 2017/0301084 A1 | 10/2017 | Gopinath |
| 2017/0309018 A1 | 10/2017 | Shalev et al. |
| 2017/0311806 A1 | 11/2017 | Comstock, II et al. |
| 2017/0325712 A1 | 11/2017 | Gopinath |
| 2017/0367581 A1 | 12/2017 | Tearney et al. |
| 2018/0003482 A1 | 1/2018 | Schmitt |
| 2018/0085095 A1 | 3/2018 | Hutchins et al. |
| 2018/0085170 A1 | 3/2018 | Gopinath |
| 2018/0125372 A1 | 5/2018 | Petroff et al. |
| 2018/0172424 A1 | 6/2018 | Comstock, II et al. |
| 2018/0177404 A1 | 6/2018 | Liu |
| 2018/0192957 A1 | 7/2018 | Schmitt et al. |
| 2018/0192983 A1 | 7/2018 | Dascal et al. |
| 2018/0225830 A1 | 8/2018 | Gopinath et al. |
| 2018/0226773 A1 | 8/2018 | Yun et al. |
| 2018/0275622 A1 | 9/2018 | Adler et al. |
| 2018/0293730 A1 | 10/2018 | Ambwani et al. |
| 2018/0306569 A1 | 10/2018 | Schmitt et al. |
| 2018/0344173 A1 | 12/2018 | Tu et al. |
| 2018/0344174 A9 | 12/2018 | Schmitt et al. |
| 2018/0353241 A1 | 12/2018 | Tu et al. |
| 2019/0035114 A1 | 1/2019 | Griffin et al. |
| 2019/0096063 A1 | 3/2019 | Ambwani |
| 2019/0099237 A1 | 4/2019 | Booker et al. |
| 2019/0220980 A1 | 7/2019 | Ambwani et al. |
| 2019/0307412 A1 | 10/2019 | Dascal et al. |
| 2019/0365480 A1 | 12/2019 | Gopinath et al. |
| 2019/0380594 A1 | 12/2019 | Schmitt et al. |
| 2020/0142575 A1 | 5/2020 | Gopinath et al. |
| 2020/0167923 A1 | 5/2020 | Gopinath |
| 2020/0355557 A1 | 11/2020 | Friedman et al. |
| 2020/0397405 A1 | 12/2020 | Hutchins et al. |
| 2021/0004955 A1 | 1/2021 | Ambwani et al. |

FOREIGN PATENT DOCUMENTS

| | | |
|---|---|---|
| CN | 1780584 | 5/2006 |
| CN | 203801215 | 9/2014 |
| CN | 203801216 | 9/2014 |
| CN | 203805643 | 9/2014 |
| CN | 203805646 | 9/2014 |
| CN | 105019592 | 11/2015 |
| CN | 204826364 | 12/2015 |
| CN | 105662387 | 6/2016 |
| CN | 106570313 | 4/2017 |
| CN | 106650029 | 5/2017 |
| CN | 106805989 | 6/2017 |
| CN | 106974622 | 7/2017 |
| CN | 107115108 | 9/2017 |
| CN | 107133959 | 9/2017 |
| CN | 107233106 | 10/2017 |
| CN | 107745346 | 3/2018 |
| CN | 107978371 | 5/2018 |
| CN | 108022650 | 5/2018 |
| CN | 108038848 | 5/2018 |
| CN | 207464715 | 6/2018 |
| DE | 69738291 | 9/2008 |
| DE | 112016005442 | 8/2018 |
| DE | 112016005603 | 10/2018 |
| EP | 0883793 | 12/1998 |
| EP | 1685366 | 8/2006 |
| EP | 2505129 | 10/2012 |
| EP | 2803973 | 11/2014 |
| GB | 2512077 | 9/2014 |
| JP | 2000503237 | 3/2000 |
| JP | 2000097845 | 4/2000 |
| JP | 2000097846 | 4/2000 |
| JP | 2005230552 | 9/2005 |
| JP | 2005533610 | 11/2005 |
| JP | 2006271869 | 10/2006 |
| JP | 2007268131 | 10/2007 |
| JP | 2008510586 | 4/2008 |
| JP | 2008523954 | 7/2008 |
| JP | 2009072291 | 4/2009 |
| JP | 4494203 | 6/2010 |
| JP | 2010167029 | 8/2010 |
| JP | 2010188138 | 9/2010 |
| JP | 2010533052 | 10/2010 |
| JP | 2011078550 | 4/2011 |
| JP | 2012147860 | 8/2012 |
| JP | 2012521852 | 9/2012 |
| JP | 5093787 | 12/2012 |
| JP | 2012254211 | 12/2012 |
| JP | 2013500142 | 1/2013 |
| JP | 2013506136 | 2/2013 |
| JP | 5269809 | 8/2013 |
| JP | 2014505496 | 3/2014 |
| JP | 5474190 | 4/2014 |
| JP | 2014180575 | 9/2014 |
| JP | 2014526283 | 10/2014 |
| JP | 5622796 | 11/2014 |
| JP | 5635149 | 12/2014 |
| JP | 5643315 | 12/2014 |
| JP | 2015013217 | 1/2015 |
| JP | 5689728 | 3/2015 |
| JP | 5721721 | 5/2015 |
| JP | 2015518393 | 7/2015 |
| JP | 5778579 | 9/2015 |
| JP | 2015164660 | 9/2015 |
| JP | 5814860 | 11/2015 |
| JP | 2015532717 | 11/2015 |
| JP | 5856605 | 2/2016 |
| JP | 2016508750 | 3/2016 |
| JP | 2016514996 | 5/2016 |
| JP | 5987025 | 9/2016 |
| JP | 5997232 | 9/2016 |
| JP | 2018507400 | 3/2018 |
| JP | 2018527961 | 9/2018 |
| WO | 2004010856 | 2/2004 |
| WO | 2004096049 | 11/2004 |
| WO | 2005047813 | 5/2005 |
| WO | 2006024015 | 3/2006 |
| WO | 2006068927 | 6/2006 |
| WO | 2008134449 | 11/2008 |
| WO | 2009009799 | 1/2009 |
| WO | 2009009802 | 1/2009 |
| WO | 2009010963 | 1/2009 |
| WO | 2010095370 | 8/2010 |
| WO | 2010113374 | 10/2010 |
| WO | 2011038010 | 3/2011 |
| WO | 2011059829 | 5/2011 |
| WO | 2012002302 | 1/2012 |
| WO | 2012064966 | 5/2012 |
| WO | 2013033415 | 3/2013 |
| WO | 2013126390 | 8/2013 |
| WO | 2014142789 | 9/2014 |
| WO | 2014142815 | 9/2014 |
| WO | 2014149127 | 9/2014 |
| WO | 2014163601 | 10/2014 |
| WO | 2014175853 | 10/2014 |
| WO | 2015044978 | 4/2015 |
| WO | 2015044982 | 4/2015 |
| WO | 2015044983 | 4/2015 |
| WO | 2015044984 | 4/2015 |
| WO | 2015074018 | 5/2015 |
| WO | 2015103277 | 7/2015 |
| WO | 2015136853 | 9/2015 |
| WO | 2015141136 | 9/2015 |
| WO | 2016168605 | 10/2016 |
| WO | 2016187218 | 11/2016 |
| WO | 2016187231 | 11/2016 |
| WO | 2016210132 | 12/2016 |
| WO | 2017011587 | 1/2017 |
| WO | 2017019626 | 2/2017 |
| WO | 2017019634 | 2/2017 |
| WO | 2015044987 | 3/2017 |
| WO | 2015045368 | 3/2017 |
| WO | 2017040484 | 3/2017 |
| WO | 2017097074 | 6/2017 |

(56) References Cited

FOREIGN PATENT DOCUMENTS

| WO | 2017189942 | 11/2017 |
|---|---|---|
| WO | 2017200381 | 11/2017 |
| WO | 2019108598 | 6/2019 |
| WO | 2020237024 | 11/2020 |

OTHER PUBLICATIONS

Chinese Office Action dated May 25, 2020 issued in corresponding Chinese Application No. 201680034490.4, with English summary.
International Preliminary Report on Patentability dated Dec. 2, 2021 issued in related International Application No. PCT/US2020/033953.
Japanese Office Action dated Nov. 17, 2020 issued in corresponding Japanese Application No. 2018-505582, with English translation.
"Imaging System Includes Imaging Probe and Delivery Devices" Specification, Drawings, and Prosecution History of U.S. Appl. No. 15/751,570, filed Feb. 9, 2018, now U.S. Pat. No. 10,631,718, issued Apr. 28, 2020, by Christopher Petroff, et al., which is stored in the United States Patent and Trademark Office (USPTO).
Athanasiou, L.S. et al. "Fully automated lumen segmentation of intracoronary optical coherence tomography images", Medical Imaging 2017, vol. 10133, p. 101332I-1-101332I-7. Downloaded from the internet on Mar. 6, 2017: http://proceedings.spiedigitallibrary.org/.
Berger, J.D. et al. "Widely tunable external cavity diode laser based on a MEMS electrostatic rotary actuator", OSA/OFC 2001, pp. TuJ2-1-TuJ2-3.
Buus, J. et al. "Tunable Lasers in Optical Networks", Journal of Lightwave Technology, vol. 24, No. 1 (Jan. 2006), pp. 5-11.
Chang-Hasnain, C.J. "Tunable VCSEL", IEEE Journal on Selected Topics in Quantum Electronics, vol. 6, No. 6 (Nov./Dec. 2000), pp. 978-987.
Chang-Hasnain, C.J., "Progress and Prospects of Long-Wavelength VCSELs", IEEE Optical Communications (Feb. 2003), pp. S30-S34.
Chinn, S.R. et al. "Optical coherence tomography using a frequency-tunable optical source", Optics Letters, vol. 22, No. 5 (Mar. 1, 1997), pp. 340-342.
Chinese Office Action dated Aug. 28, 2019 issued in corresponding Chinese Application No. 201680034490.4, with English summary.
Chinese Office Action dated Feb. 27, 2019 issued in corresponding Chinese Application No. 201680034490.4, with English translation.
European Office Action dated Feb. 4, 2020 issued in corresponding European Application No. 16780839.3.
Extended European Search Report dated Apr. 9, 2019 issued in corresponding European Application No. 16842796.1.
Extended European Search Report dated Jan. 2, 2019 issued in corresponding European Application No. 16780839.3.
International Preliminary Report on Patentability dated Mar. 15, 2018 issued in corresponding International Application No. PCT/US2016/049415.
International Preliminary Report on Patentability dated Oct. 17, 2017 issued in corresponding International Application No. PCT/US2016/027764.
International Search Report & Written Opinion dated Feb. 11, 2019, issued in related International Application No. PCT/US2018/062766.
International Search Report and Written Opinion dated Jan. 31, 2020 issued in corresponding International Application No. PCT/US2019/051447.
International Search Report dated Jul. 14, 2016 issued in corresponding International Application No. PCT/US2016/027764.
International Search Report dated Nov. 7, 2016, issued in corresponding International Application No. PCT/US2016/049415.
Japanese Office Action dated Mar. 31, 2020 issued in corresponding Japanese Application No. 2018-505582, with English translation.
Fermann, M.E. et al. "Ultrawide tunable Er solition fiber laser amplified in Yb-doped fiber", Optics Letters, vol. 24, No. 20 (Oct. 15, 1999), pp. 1428-1430.
Focabex, "Core Structure of Optical Cables" Article (online). Feb. 1, 2002 (retrieved Jan. 8, 2020). Retrieved from the Internet: URL: http://www.focabex.com/library-n/CORE-STRUCTURE-OF-OPTICAL-FIBER-CABLES.pdf.
Golubovic, B. et al. "Optical frequency-domain reflectometry using rapid wavelength tuning of a Cr4+:forsterite laser", Optics Letters, vol. 22, No. 22 (Nov. 15, 1997), pp. 1704-1706.
Harris Jr., J.S. "Tunable Long-Wavelength Vertical-Cavity Lasers: The Engine of Next Generation Optical Networks?", IEEE Journal on Selected Topics in Quantum Electronics, vol. 6, No. 6 (Nov./Dec. 2000), pp. 1145-1160.
Kakuta, T. et al. "Behavior of optical fibers under heavy irradiation", Fusion Engineering and Design, vol. 41 (1998), pp. 201-205.
Meuwissen, M. et al. "Role of Variability in Microvascular Resistance onFractional Flow Reserve and Coronary Blood Flow Velocity Reserve in Intermediate Coronary Lesions", Circulation, 103 (2001), pp. 184-187 [online—retrieved on Mar. 7, 2018]. Retrieved from the Internet URL: http://circ.ahajournals.org/content/103/2/184.
Ofili, E.O. et al. "Differential characterization of blood flow, velocity, and vascular resistance between proximal and distal normal epicardial human coronary arteries: Analysis by intracoronary Doppler spectral flow velocity", American Heart Journal (Jul. 1995), pp. 37-46.
Reed, W.A. et al. "Gradient-index fiber-optic microprobes for minimally invasive in vivo low-coherence interferometry", Optics Letters, vol. 27, No. 20 (Oct. 15, 2002), pp. 1794-1796.
Fearney, G.J. et al. "High-speed phase- and group-delay scanning with a grating-based phase control delay line", Optics Letters, vol. 22, No. 23 (Dec. 1, 1997), pp. 1811-1813.
Thorlabs, "Single Wavelength Graded-Index (GRIN) Lenses" Product Catalogue (online). Apr. 9, 2016 (retrieved Jan. 8, 2020). Retrieved from the Internet: URL: https://www.thorlabs.com/NewGroupPage9.cfm? ObjectGroup_ID=1209.
Von der Weid, J.P. et al. "On the Characterization of Optical Fiber Network Components with Optical Frequency Domain Reflectometry", Journal of Lightwave Technology, vol. 15, No. 7 (Jul. 1997), pp. 1131-1141.
Xi et al. "Diffractive catheter for ultrahigh-resolution spectral-domain volumetric OCT imaging", Optics Letters, vol. 39, No. 7 (Mar. 26, 2014), pp. 2016-2019.
Youngquist, R.C. et al."Optical coherence-domain reflectometry: a new optical evaluation technique", Optics Letters, vol. 12, No. 3 (Mar. 1987), pp. 158-160.
Yun, S.H. et al. "High-speed optical frequency-domain imaging", Optics Express, vol. 11, No. 22 (Nov. 3, 2003), pp. 2953-2963.
Zheng, W. "Optic Lenses Manufactured on Fiber Ends", IEEE, 978-1-4673-7732-4/15, 2015, pp. 1-10.
International Preliminary Report on Patentability dated Jun. 11, 2020 issued in corresponding International Application No. PCT/US2018/062766.
Japanese Office Action dated Mar. 16, 2021 issued in corresponding Japanese Application No. 2018-510969, with English language summary.
Ghannam, M.T., et al. "Rheological Properties of Poly(dimethylsiloxane)". Industrial & Engineering Chemistry Research vol. 37, No. 4 (1998) pp. 1335-1340.
Extended European Search Report dated Nov. 26, 2021 issued in corresponding European Application No. 18883166.3.
International Preliminary Report on Patentability dated Nov. 11, 2021 issued in corresponding International Application No. PCT/US20/30616.
Extended European Search Report dated Apr. 21, 2022 issued in corresponding European Application No. 19862071.8.
Tran et al. "In vivo endoscopic optical coherence tomography by use of a rotational microelectromechanical system probe", Optics Letters, vol. 29 No. 11 (Jun. 1, 2004), p. 1236-1238.
Japanese Office Action dated Apr. 26, 2022 issued in corresponding Japanese Application No. 2021-068226, with English translation.

(56) References Cited

OTHER PUBLICATIONS

Japanese Office Action dated Sep. 15, 2020 issued in corresponding Japanese Application No. 2018-510969, with English language summary.
International Search Report and Written Opinion dated Sep. 14, 2020 issued in corresponding International Application No. PCT/US20/30616.
International Search Report and Written Opinion dated Jul. 30, 2020 issued in corresponding International Application No. PCT/US20/33953.
Abozenadah, H., et al. Consumer Chemistry: How Organic Chemistry Impacts Our Lives. CC BY-NC-SA. Available at: https://wou.edu/chemistry/courses/online-chemistry-textbooks/ch105-consumer-chemistry/ (2017).
Introduction to silicone fluids (https://www.clearcoproducts.com/introduction-to-silicone-fluids.html), retrieved Sep. 24, 2020.
Madigan, Jeremy. "Vascular access: guide catheter selection, usage, and compatibility." Interventional Neuroradiology, Springer, London (2014), pp. 27-38.
European Office Action dated Apr. 21, 2021 issued in corresponding European Application No. 16842796.1.
International Search Report and Written Opinion dated Aug. 2, 2021 issued in corresponding International Application No. PCT/US2021/029836.
Chinese Notice of Allowance and Supplementary Search Report dated Jan. 13, 2021 issued in corresponding Chinese Application No. 201680034490.4.
BiazePhotonics. "NL-2.4-800 Highly nonlinear PCF" technical specification sheet (Oct. 2011) (Resubmission with publication date of reference originally submitted with IDS dated Jul. 8, 2020).
NKT Photonics. "ESM-12 SingleOmode 12 um core fiber" technical specification sheet (Jul. 2011) (Resubmission with publication date of reference originally submitted with IDS dated Jul. 8, 2020).
NKT Photonics. "HC-1550-02 Hollow Core Photonic Bandgap Fiber" technical specification sheet (Oct. 2007) (Resubmission with publication date of reference originally submitted with IDS dated Jul. 8, 2020).
NKT Photonics. "HC-800-02 Hollow Core Photonic Bandgap Fiber" technical specification sheet (Oct. 2007) (Resubmission with publication date of reference originally submitted with IDS dated Jul. 8, 2020).
Japanese Office Action dated Nov. 15, 2022 issued in related Japanese Application No. 2021-068226, with English translation.
International Preliminary Report on Patentability electronically transmitted to Applicant on Nov. 10, 2022, issued in related International Application No. PCT/US2021/029836.
Japanese Office Action dated Aug. 2, 2022 issued in corresponding Japanese Application No. 2021-117103, with English translation.
Japanese Office Action dated Feb. 21, 2023 issued in corresponding Japanese Application No. 2021-117103, with English summary.
Summons To Attend Oral Proceedings dated Mar. 17, 2023 issued in related European Application No. 16842796.1.
Brezinski et al. "Optical Coherence Tomography: High-Resolution Imaging in Nontransparent Tissue", IEEE Journal of Selected Topics in Quantum Electronics, vol. 5, No. 4, Jul./Aug. 1999, pp. 1185-1192.
Extended European Search Report dated Mar. 21, 2023 issued in corresponding European Application No. 20798343.8.
International Search Report and Written Opinion dated Apr. 14, 2023 issued in related International Application No. PCT/US2023/010508.
Atif et al. "Catheters for optical coherence tomography", Laser Physics Letters, vol. 8, No. 9, (Jul. 1, 2011), pp. 629-646.
Extended European Search Report dated Apr. 21, 2023 issued in related European Application No. 20810126.1.
Japanese Office Action dated Apr. 25, 2023 issued in related Japanese Application No. 2021-514598, with English summary.

\* cited by examiner

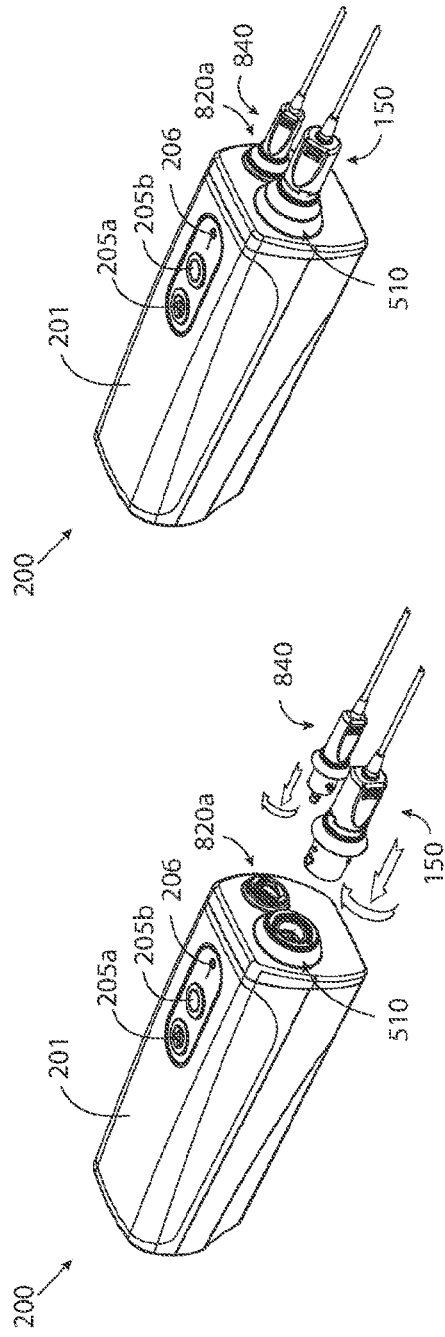
FIG. 4A
FIG. 4B
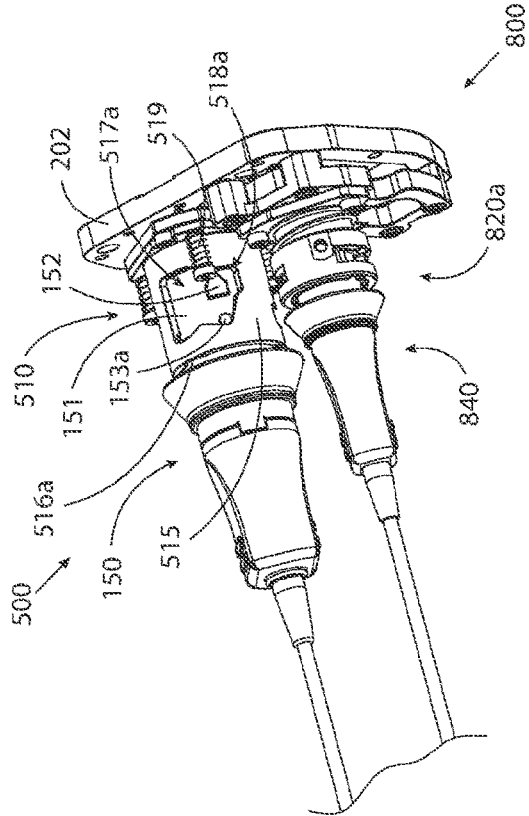
FIG. 4C

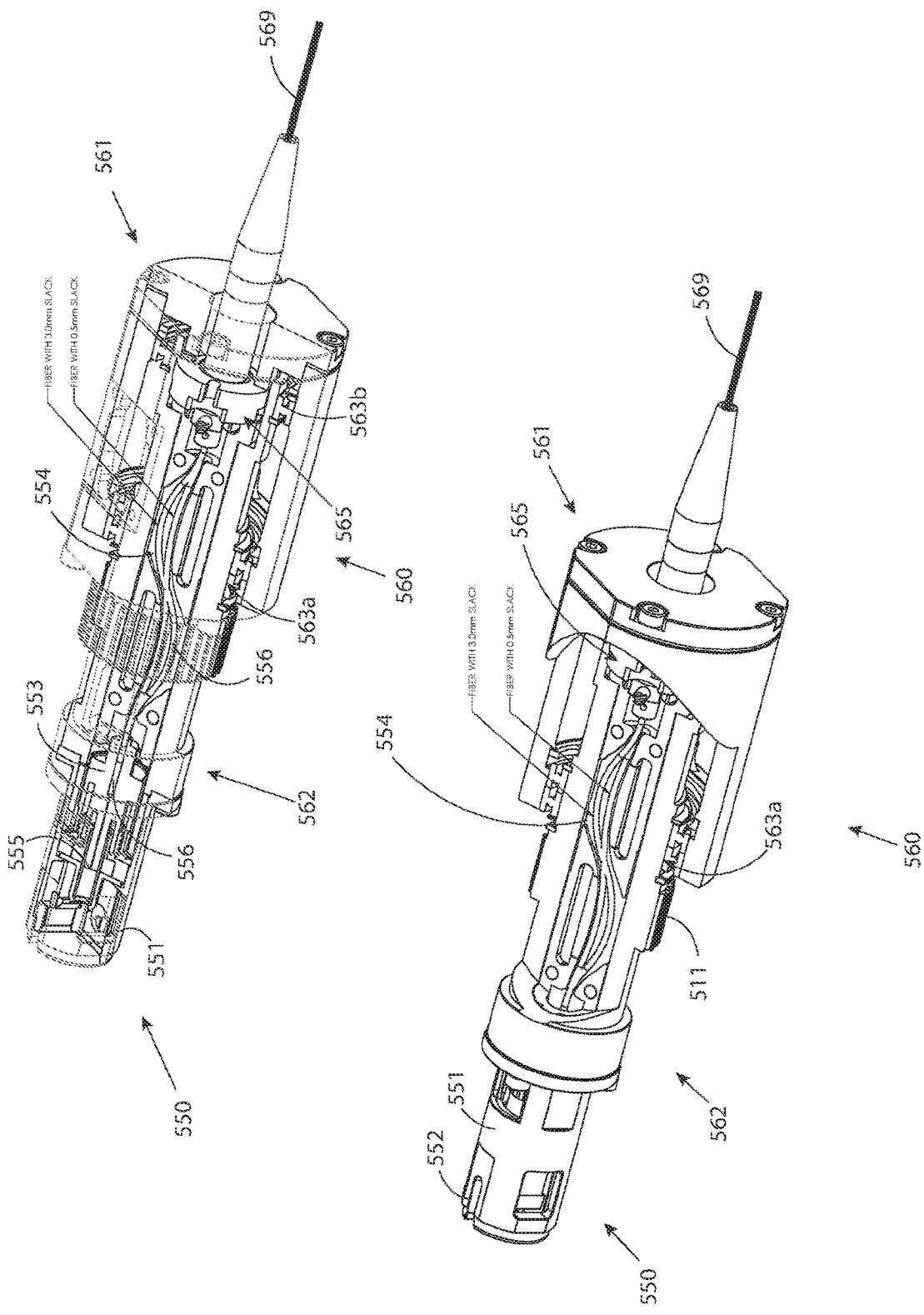

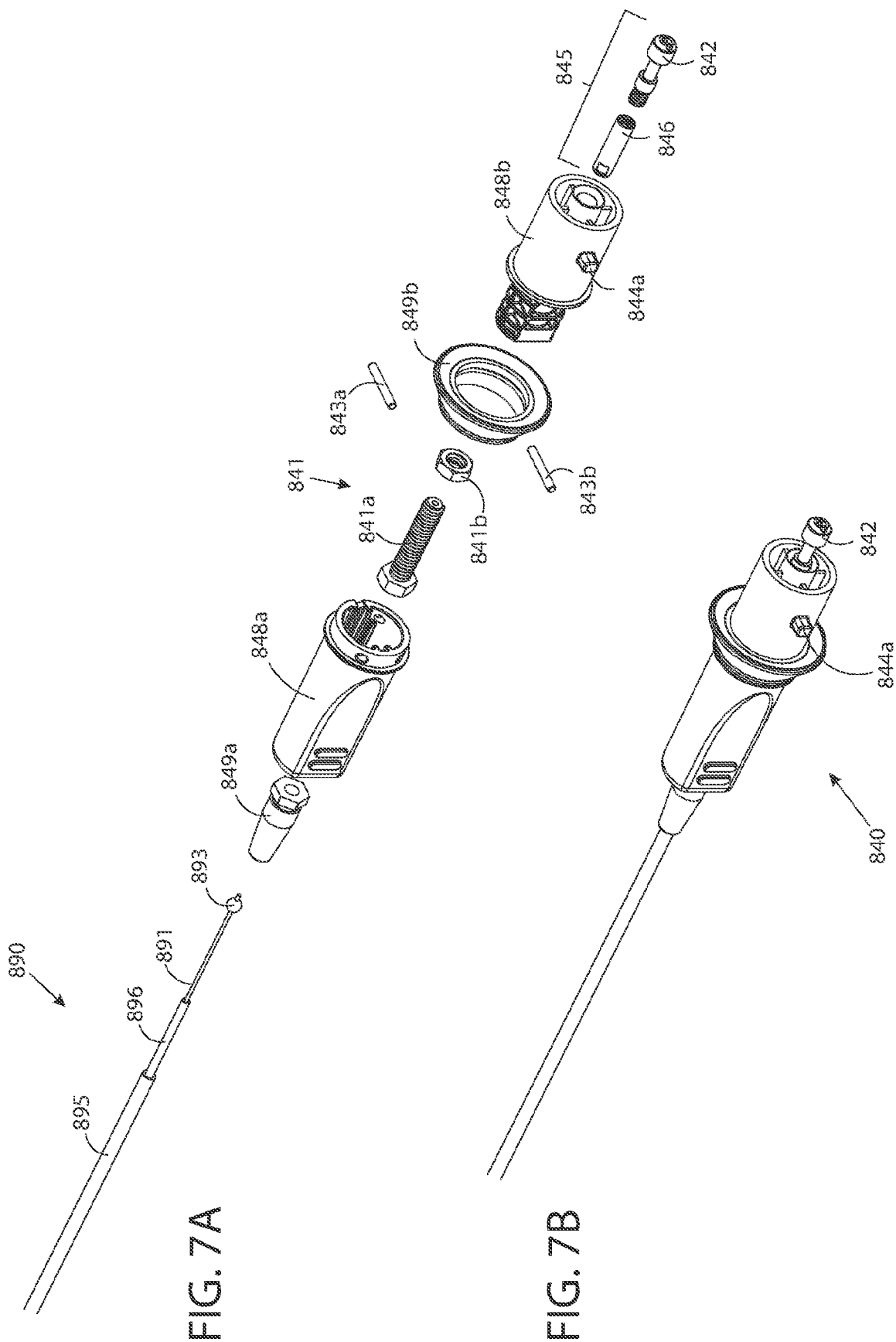

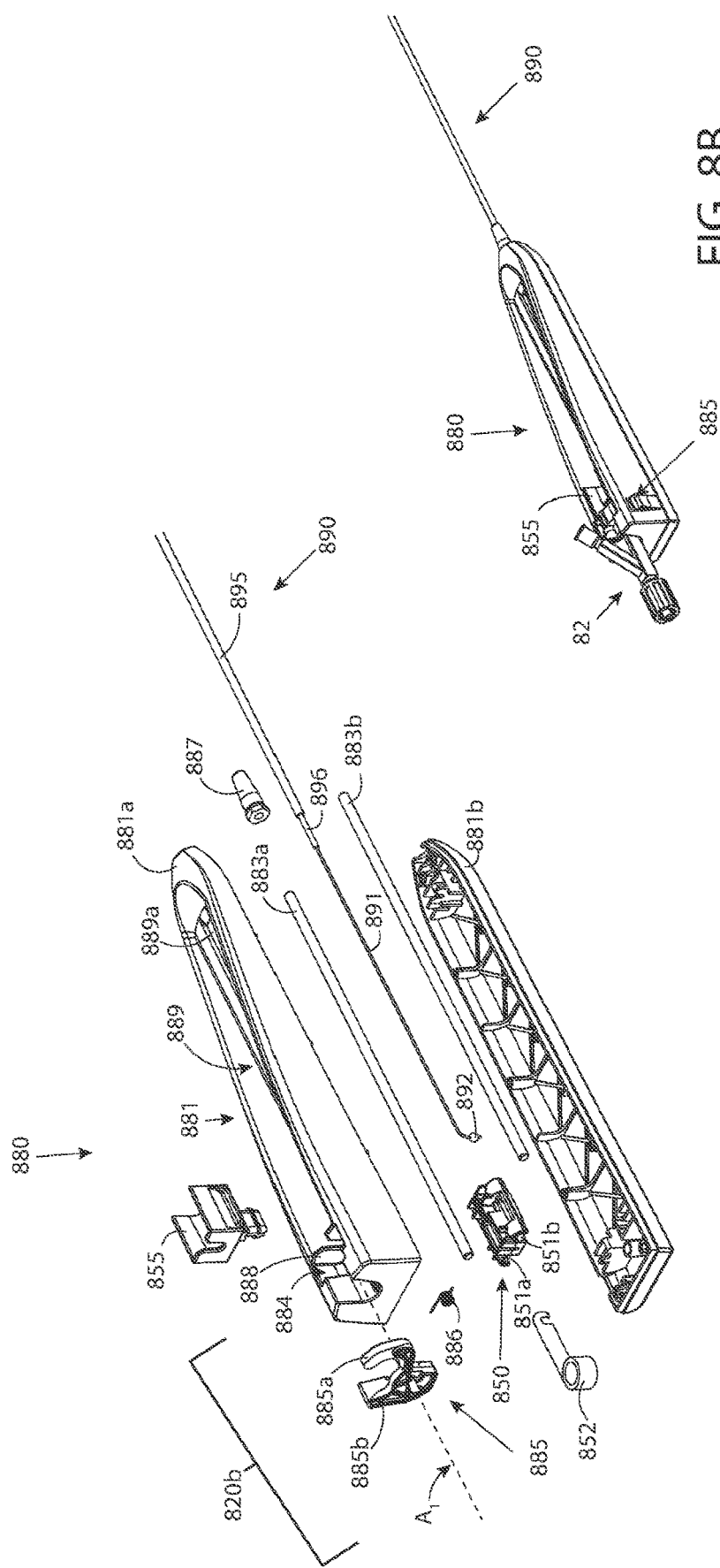
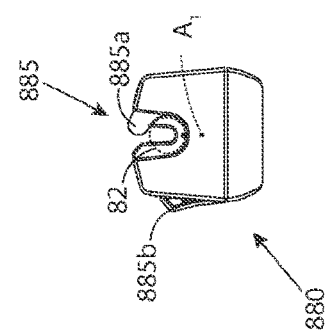

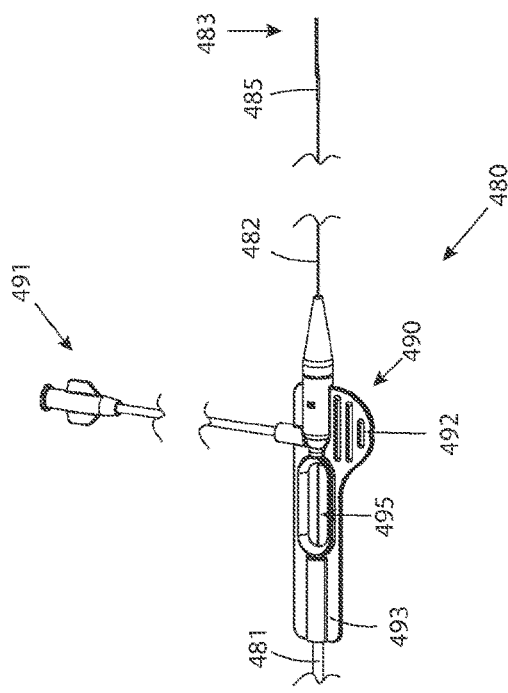
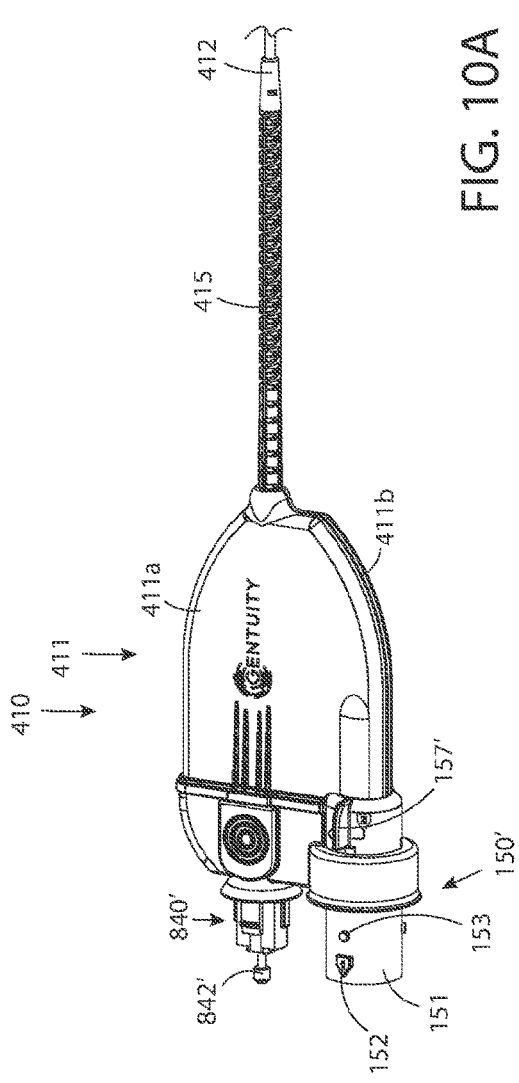
FIG. 10A
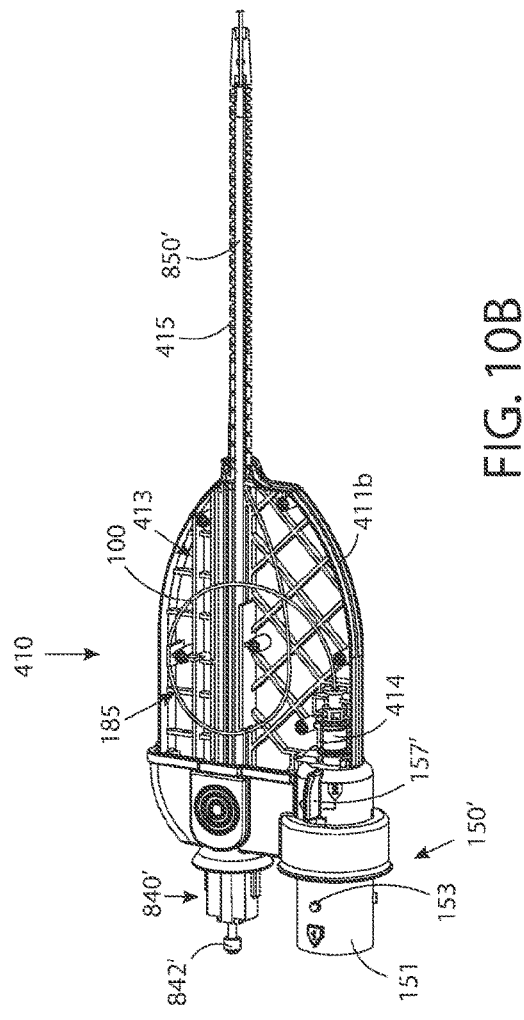
FIG. 10B

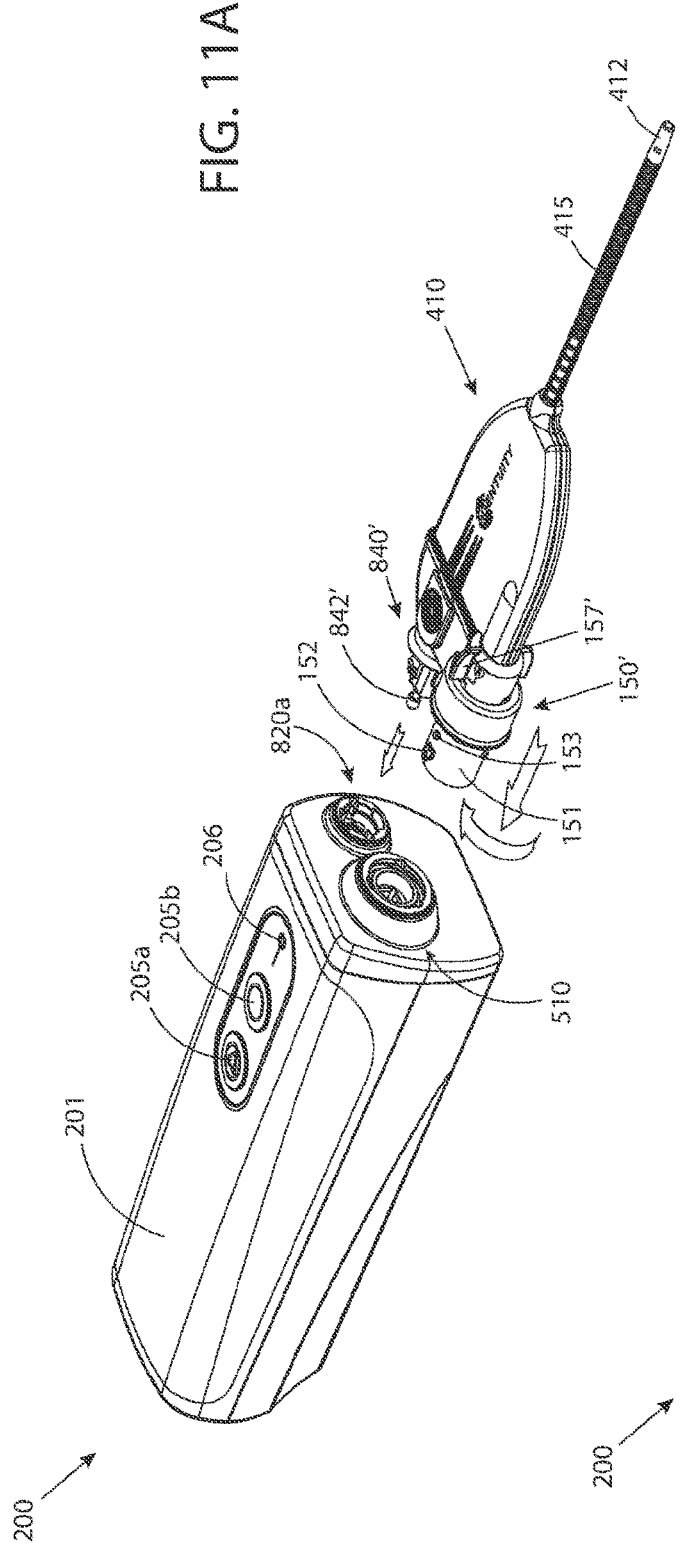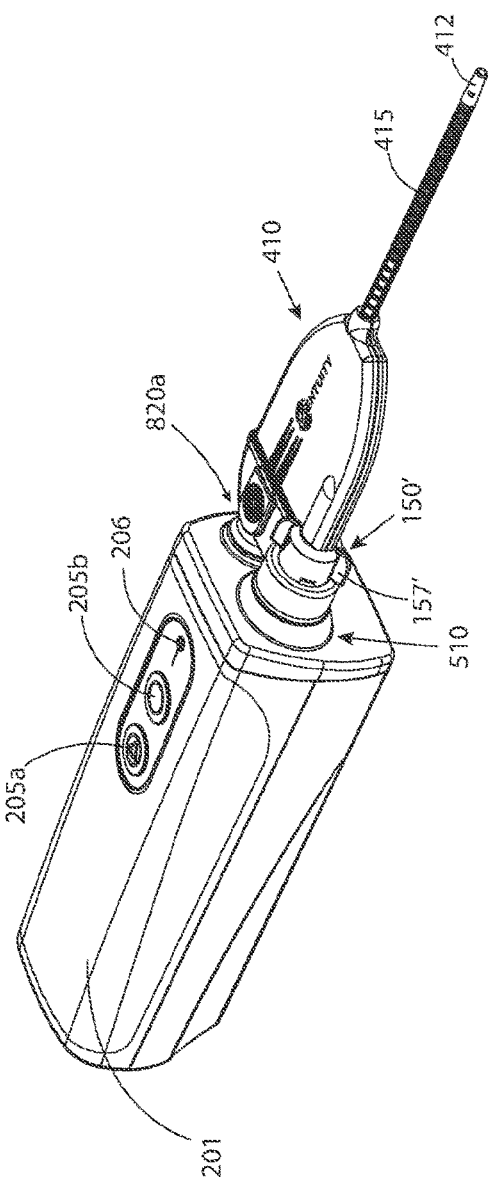

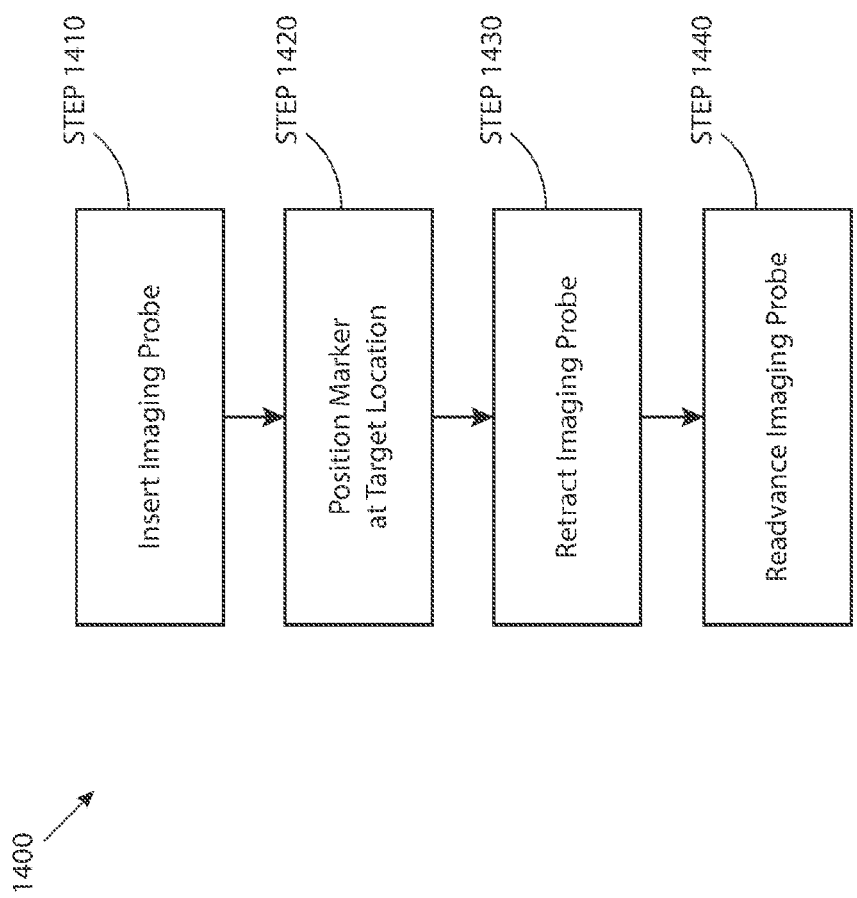

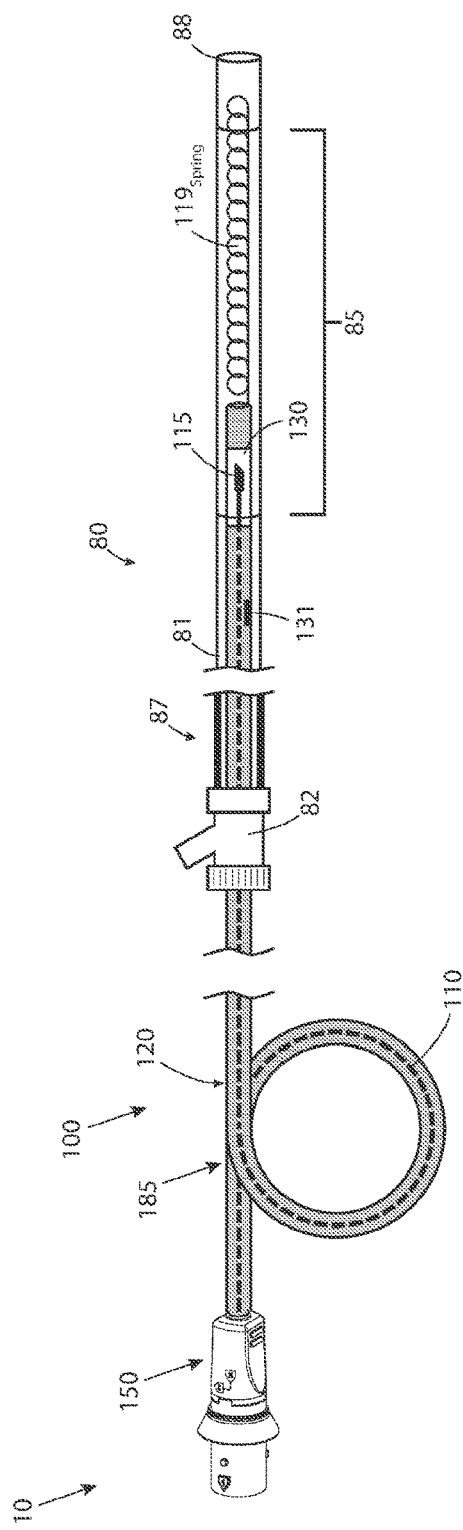
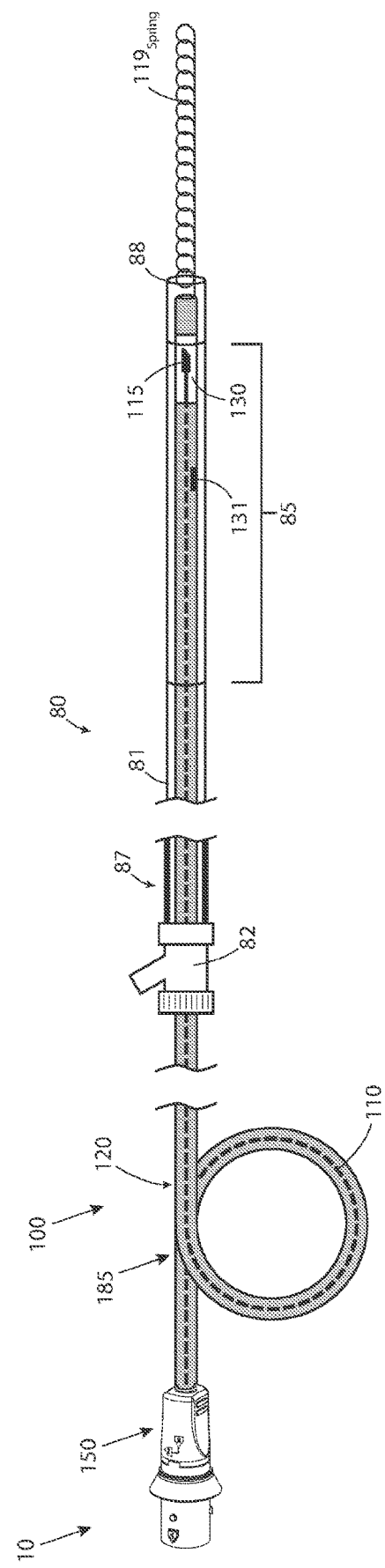
FIG. 15A
FIG. 15B

IMAGING SYSTEM

RELATED APPLICATIONS

This application claims priority to U.S. Provisional Application Ser. No. 62/591,403, titled "Imaging System", filed Nov. 28, 2017, and U.S. Provisional Application Ser. No. 62/671,142, titled "Imaging System", filed May 14, 2018, the content of each of which is incorporated herein by reference in its entirety.

This application is related to U.S. Provisional Application Ser. No. 62/148,355, titled "Micro-Optic Probes for Neurology", filed Apr. 16, 2015, the content of which is incorporated by reference in its entirety.

This application is related to U.S. Provisional Application Ser. No. 62/322,182, titled "Micro-Optic Probes for Neurology", filed Apr. 13, 2016, the content of which is incorporated by reference in its entirety.

This application is related to International PCT Patent Application Serial Number PCT/US2016/027764, titled "Micro-Optic Probes for Neurology" filed Apr. 15, 2016, published as WO 2016/168605, published Oct. 20, 2016, the content of which is incorporated by reference in its entirety.

This application is related to U.S. patent application Ser. No. 15/566,041, titled "Micro-Optic Probes for Neurology", filed Apr. 15, 2016, published as U.S. Publication No. 2018-0125372, published May 10, 2018, the content of which is incorporated by reference in its entirety.

This application is related to U.S. Provisional Application Ser. No. 62/212,173, titled "Imaging System Includes Imaging Probe and Delivery Devices", filed Aug. 31, 2015, the content of which is incorporated by reference in its entirety.

This application is related to U.S. Provisional Application Ser. No. 62/368,387, titled "Imaging System Includes Imaging Probe and Delivery Devices", filed Jul. 29, 2016, the content of which is incorporated by reference in its entirety.

This application is related to International PCT Patent Applicant Serial Number PCT/US2016/049415, titled "Imaging System Includes Imaging Probe and Delivery Devices", filed Aug. 30, 2016, published as WO 2017/040484, published Mar. 9, 2017, the content of which is incorporated by reference in its entirety.

This application is related to U.S. patent application Ser. No. 15/751,570, titled "Imaging System Includes Imaging Probe and Delivery Devices", filed Feb. 9, 2018, published as US Publication No. 20190274528, published September 2019, the content of which is incorporated by reference in its entirety.

This application is related to U.S. Provisional Application Ser. No. 62/732,114, titled "Imaging System with Optical Pathway", filed Sep. 17, 2018, the content of which is incorporated by reference in its entirety.

FIELD

The present disclosure relates generally to imaging systems, and in particular, intravascular imaging systems including imaging probes and delivery devices.

BACKGROUND

Imaging probes have been commercialized for imaging various internal locations of a patient, such as an intravascular probe for imaging a patient's heart. Current imaging probes are limited in their ability to reach certain anatomical locations due to their size and rigidity. Current imaging probes are inserted over a guidewire, which can compromise their placement and limit use of one or more delivery catheters through which the imaging probe is inserted. There is a need for imaging systems that include probes with reduced diameter, high flexibility and ability to be advanced to a patient site to be imaged without a guidewire, as well as systems with one or more delivery devices compatible with these improved imaging probes.

SUMMARY

According to an aspect of the present inventive concepts, an imaging system for a patient comprising: an imaging probe, comprising: an elongate shaft comprising a proximal end, a distal portion, and a lumen extending between the proximal end and the distal portion; a rotatable optical core positioned within the lumen of the elongate shaft and comprising a proximal end and a distal end; and an optical assembly positioned in the elongate shaft distal portion and proximate the rotatable optical core distal end, the optical assembly configured to direct light to tissue and collect reflected light from the tissue; and the imaging probe is constructed and arranged to collect image data from a patient site; a rotation assembly constructed and arranged to optically and mechanically connect to the imaging probe, and to rotate the optical assembly; a retraction assembly constructed and arranged to mechanically connect to the imaging probe, and to retract the optical assembly and the elongate shaft in unison.

In some embodiments, the imaging probe further comprises a service loop configured to allow retraction of the imaging probe relative to the patient while the rotation assembly remains stationary.

In some embodiments, the elongate shaft comprises a first segment and a second segment, and the first segment is more flexible than the second segment. The first segment can comprise a spiral cut. The first segment can comprise a braided construction. The first segment can be positioned proximal to the second segment.

In some embodiments, the rotatable optical core comprises a non-zero dispersion shifted fiber. The system can optically match the dispersion of the non-zero dispersion shifted fiber.

In some embodiments, the rotatable optical core comprises a radiation-resistant fiber. The rotatable optical core can further comprise an acrylate coating.

In some embodiments, the rotatable optical core comprises a first portion and a second portion, and the first portion comprises a first set of properties, and the second portion comprises a second set of properties different than the first set of properties. The first portion can comprise a non-zero dispersion shifted fiber and/or a depressed cladding, and the second portion can comprise a non-shifted optical fiber.

In some embodiments, the optical assembly comprises a lens. The lens can comprise a GRIN lens with a distal end, and the distal end can comprise a beam deflector. The lens can comprise a doping profile configured to provide a particular focus requirement and/or to allow polishing of a beam-deflecting surface directly into the lens while preserving intended optical function. The distal end can comprise a plated distal end. The distal end can comprise an aspherical distal end. The distal end can comprise a polished facet.

In some embodiments, the imaging probe comprises a proximal connector; and the retraction assembly comprises a pullback module and a linkage assembly; and the pullback module is configured to attach to the elongate shaft of the imaging probe and to retract the imaging probe. The system can further comprise a patient interface module configured to: attach to the proximal connector; attach to the linkage assembly; provide a retraction force to the pullback module via the linkage assembly; and rotate the rotatable optical core. The pullback module can comprise a first discrete component that can be positioned at a first location, and the patient interface module can further comprise a second discrete component that can be positioned at a second location that can be remote from the first location. The imaging probe can enter the patient at a vascular access site, and the first location can comprise a location proximate the vascular access site. The second location can be at least 15 cm remote from the first location. The first location can be within 30 cm of the vascular access site. The retraction assembly can comprise a linkage assembly including a sheath with a distal end, a puller, and a motive element, and the motive element can apply a pullback force to the puller via the linkage assembly to cause the puller to move proximally relative to the distal end of the sheath.

In some embodiments, the imaging probe comprises a proximal portion and a proximal connector within the proximal portion; and the system further comprises a connector module including a housing, a first connector, and a linkage, and the housing surrounds the proximal portion of the imaging probe, and the proximal connector is attached to the housing, and the linkage is attached to the elongate shaft of the imaging probe, and the first connector slidingly receives the linkage. The system can further comprise a patient interface module, including a second connector that attaches to the first connector and a third connector that attaches to the proximal connector, and the patient interface module retracts the linkage of the connector module, and the housing of the connector module surrounds the retracted portion of the imaging probe, and the patient interface module rotates the rotatable optical core.

In some embodiments, the rotation assembly rotates the optical assembly and the rotatable optical core in unison.

In some embodiments, the imaging probe comprises a proximal end including a connector, and the rotation assembly comprises a rotary joint that operably engages the connector, and the rotary joint rotates the rotatable optical core via the connector. The rotary joint can comprise an optical connector and a floating portion, and the floating portion can be configured to compensate for linear motion of the optical connector. The floating portion can be biased toward the optical connector. The floating portion can comprise a spring that provides the bias. The rotary joint can further comprise a rotary coupler and a fiber optic cable, and the rotary coupler can be connected to the floating portion via the fiber optic cable, and the fiber optic cable can be configured to buckle during the linear motion compensation by the floating portion. The rotary joint can further comprise a channel configured to limit buckling of the fiber optic cable, such as to achieve a rotationally balanced configuration. The channel can be configured to confine the buckling of the fiber optic cable to a single plane. The fiber optic cable can comprise a portion configured to accommodate the buckling, and the portion can comprise an S-shape. The channel can comprise an S-shape. The S-shape can comprise a radius configured to minimize light loss through the fiber optic cable.

In some embodiments, the retraction assembly comprises a connector assembly configured to attach to a reference point. The reference point can comprise a patient introduction device and/or a surgical table.

In some embodiments, the imaging probe further comprises a proximal end and a connector assembly positioned on the proximal end. The connector assembly can be configured to be operably attached to the rotation assembly. The connector assembly can include a fiber optic connector and one or more alignment components, and the one or more alignment components can be configured to maintain a rotational orientation of the fiber optic connector relative to the rotation assembly, and the rotational orientation can be maintained during attachment and detachment of the connector assembly to the rotation assembly. The system may not require additional alignment steps to maintain the rotational orientation. The connector assembly can comprise a rotating assembly operably attached to the rotatable optical core, and the rotation assembly can rotate the rotatable optical core via the rotating assembly of the connector assembly. The rotating assembly can comprise one or more projections and/or one or more reliefs, and the one or more projections and/or the one or more reliefs can be configured to rotationally balance the rotating assembly. The connector assembly can comprise an optical connector, and the optical connector can comprise a rotationally unbalanced optical connector. The rotating assembly can comprise a locking assembly configured to prevent rotation of the rotating assembly when the connector assembly is not attached to the rotation assembly. The locking assembly can include a rotational lock and a spring, and the rotational lock can lock to the rotating assembly via the spring. The rotating assembly can comprise one or more recesses, and the rotational lock can comprise one or more projections that mate with the one or more recesses.

In some embodiments, the imaging probe further comprises a viscous dampening material positioned between the elongate shaft and the optical assembly. The viscous dampening material can be further positioned between the elongate shaft and at least a portion of the rotatable optical core. The viscous dampening material can comprise a shear-thinning fluid. The viscous dampening material can comprise a static viscosity of at least 500 centipoise. The viscous dampening material can comprise a shear viscosity and a static viscosity, and the shear viscosity can be less than the static viscosity. The ratio of shear viscosity to static viscosity can be between 1:1.2 and 1:100. The imaging probe can further comprise: a lens; a sheath surrounding and extending beyond the lens; a sealing element positioned within the sheath distal to the lens and in contact with the viscous dampening fluid; and a chamber positioned between the lens and the sealing element. The sealing element can comprise a porous sealing element. The sealing element can be configured to prevent the viscous damping material from contacting the lens. The sealing element can be configured to allow pressure to equalize within the chamber. The sealing element can comprise a porous sealing element. The sealing element can comprise an opening. The chamber can be filled with a gas.

In some embodiments, the elongate shaft of the imaging probe comprises a proximal portion, and the imaging probe further comprises a torque shaft including a distal end and surrounding the proximal portion of the elongate shaft. The torque shaft can be configured to rotate in a single direction. The imaging probe can comprise a proximal end, and the torque shaft distal end can be positioned approximately 100 cm from the proximal end of the imaging probe. The torque shaft can be fixedly attached to the rotatable optical core. The rotatable optical core can comprise a proximal portion, and the imaging probe can comprise: a rotating alignment element positioned between the torque shaft and the rotatable optical core; an outer shaft surrounding the torque shaft and the proximal portion of the rotatable optical core; an intermediate shaft surrounding the rotatable optical core distal to the torque shaft; and a tube positioned between the outer shaft and the intermediate shaft; and the rotating alignment element and the tube form a rotary joint such that the torque shaft rotatably attaches to the intermediate shaft.

In some embodiments, the imaging probe further comprises a distal tip portion including a sealing element positioned within the elongate shaft at a location distal to the optical assembly. The distal tip portion can comprise a proximal end, and the optical assembly can include a lens, and the sealing element can comprise an angled proximal end that can be configured to reduce coupling of light between the lens of the optical assembly and the proximal end of the distal tip portion.

In some embodiments, the system further comprises a compression relief assembly configured to prevent the imaging probe from exceeding a compression threshold, and the compression relief assembly comprises: a first shaft with a proximal end, a distal end, and a first lumen therebetween; a second shaft with a proximal end, a distal end, and a second lumen therebetween; a housing with a proximal end, a distal end, and an opening therebetween; and the distal end of the first shaft connects to the proximal end of the housing; and the proximal end of the second shaft connects to the distal end of the housing; and the imaging probe is configured to pass through the first lumen, through the opening, and into the second lumen; and the opening is sized to accommodate a buckling of a portion of the elongate shaft positioned within the opening when the imaging probe exceeds the compression threshold.

In some embodiments, the system further comprises an algorithm. The algorithm can adjust a retraction parameter of the system. The retraction parameter can comprise initiation of retraction, and the algorithm can initiate retraction based on a condition selected from the group consisting of: the lumen in which the optical assembly can be positioned has been flushed; an indicator signal can be received from a fluid injector device; a desired change in image data collected can be detected; and combinations of these. The algorithm can adjust a system parameter that can be related to the imaging probe. The imaging probe can include an ID that can be detectable by the system, and the system parameter can be adjusted based on the ID. The system parameter adjustment can comprise an arm path length parameter.

In some embodiments, the system further comprises a fluid injector. The fluid injector can be configured to deliver a first fluid and a second fluid. The fluid injector can be configured to deliver the first fluid and the second fluid simultaneously and/or sequentially. The first fluid can comprise a contrast at a first concentration, and the second fluid can comprise a contrast at a second concentration that can be less than the first concentration. The second fluid can comprise no contrast.

In some embodiments, the system further comprises a marker positioned proximate the distal portion of the elongate shaft.

In some embodiments, the system further comprises a first delivery catheter constructed and arranged to slidingly receive the imaging probe, and the first delivery catheter is configured to access a body location in the patient selected from the group consisting of: an intracerebral location; an intracardiac location; and combinations of these. The imaging system can further comprise a second delivery catheter constructed and arranged to slidingly receive the first imaging catheter. The first delivery catheter can be further configured to slidingly receive a second device. The first delivery device can be configured to sequentially receive the imaging probe and the second device. The first delivery device can be configured to simultaneously receive the imaging probe and the second device. The second device can comprise a device selected from the group consisting of: a second imaging device; a treatment device; an implant delivery device; and combinations of these.

In some embodiments, the system further comprises a light source configured to deliver light to the optical assembly.

In some embodiments, the system further comprises a second imaging device. The second imaging device can be selected from the group consisting of: an X-ray; a fluoroscope such as a single plane or biplane fluoroscope; a CT Scanner; an MRI; a PET Scanner; an ultrasound imager; a rotational angiography imaging device; and combinations of these. The system can provide images based on both data provided by the imaging probe, as well as data provided by the second imaging device. The second imaging device can comprise a rotational angiography device.

In some embodiments, the system further comprises: two microcatheters; an intermediate catheter; and a treatment device. The intermediate catheter can be constructed and arranged to slidingly receive the two microcatheters in a side-by-side arrangement. The imaging probe can be advanced through the first microcatheter, and the treatment device can be advanced through the second microcatheter. The probe can be configured to perform a pullback imaging procedure prior to, during, and/or after treatment by the treatment device. The treatment device can comprise an implant delivery device. The implant delivery device can comprise a coil delivery device. The system can be configured to automatically deliver a flush medium during the pullback imaging procedure.

In some embodiments, the imaging probe comprises a spring tip including a distal end. The imaging probe can comprise a length configured to allow a clinician to position the optical assembly at a first location and subsequently perform a pullback imaging procedure, and the spring tip distal end can be positioned at or distal to the first location at the end of the pullback imaging procedure. The imaging probe can further comprise a marker positioned relative to the distal end of the spring tip distal, and the marker can provide information related to the position of the spring tip at the end of the pullback imaging procedure. The imaging probe can further comprise a marker positioned relative to the optical assembly, and the marker can provide information related to the position of the optical assembly at the end of the pullback imaging procedure. The spring tip can comprise a length of at least 35 mm, at least 50 mm, and/or at least 75 mm.

In some embodiments, the system further comprises a microcatheter including a distal transparent window, and the microcatheter can be configured to slidingly receive the imaging probe. The optical assembly can remain within the transparent window during the pullback imaging procedure. The microcatheter can include a reinforced portion proximal to the transparent window.

In some embodiments, the system further comprises a bed rail mount for attaching the rotation assembly to a patient bed rail. The bed rail mount can comprise a jaw biased in a closed position. The jaw can be constructed and arranged to capture bed rails of various size. The bed rail mount can comprise a connector that rotatably connects to the rotation assembly. The connector can comprise a persistent frictional rotation resistance.

The technology described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

FIGS. 4A-C illustrate two perspective views of connectors being attached to a patient interface module and a perspective view of a portion of the patient interface module with the outer casing removed, consistent with the present inventive concepts.

FIGS. 5A-D illustrate perspective, partial cut away views of components of a patient interface module, consistent with the present inventive concepts.

FIGS. 7A-C illustrate an exploded view, a perspective view, and a sectional view of a connector assembly, consistent with the present inventive concepts.

FIGS. 8A-C illustrate an exploded view, a perspective view, and an end view of a pullback housing, consistent with the present inventive concepts.

FIGS. 10A and 10B illustrate perspective and partial sectional views of a connector assembly, respectively, consistent with the present inventive concepts.

FIGS. 11A and 11B illustrate perspective views of connectors being attached to a patient interface module, consistent with the present inventive concepts.

FIG. 14 illustrates a flow chart of a method of creating an image, consistent with the present inventive concepts.

FIGS. 15A and 15B illustrate schematic views of a system including an imaging probe, consistent with the present inventive concepts.

DETAILED DESCRIPTION OF THE DRAWINGS

Figure 1:
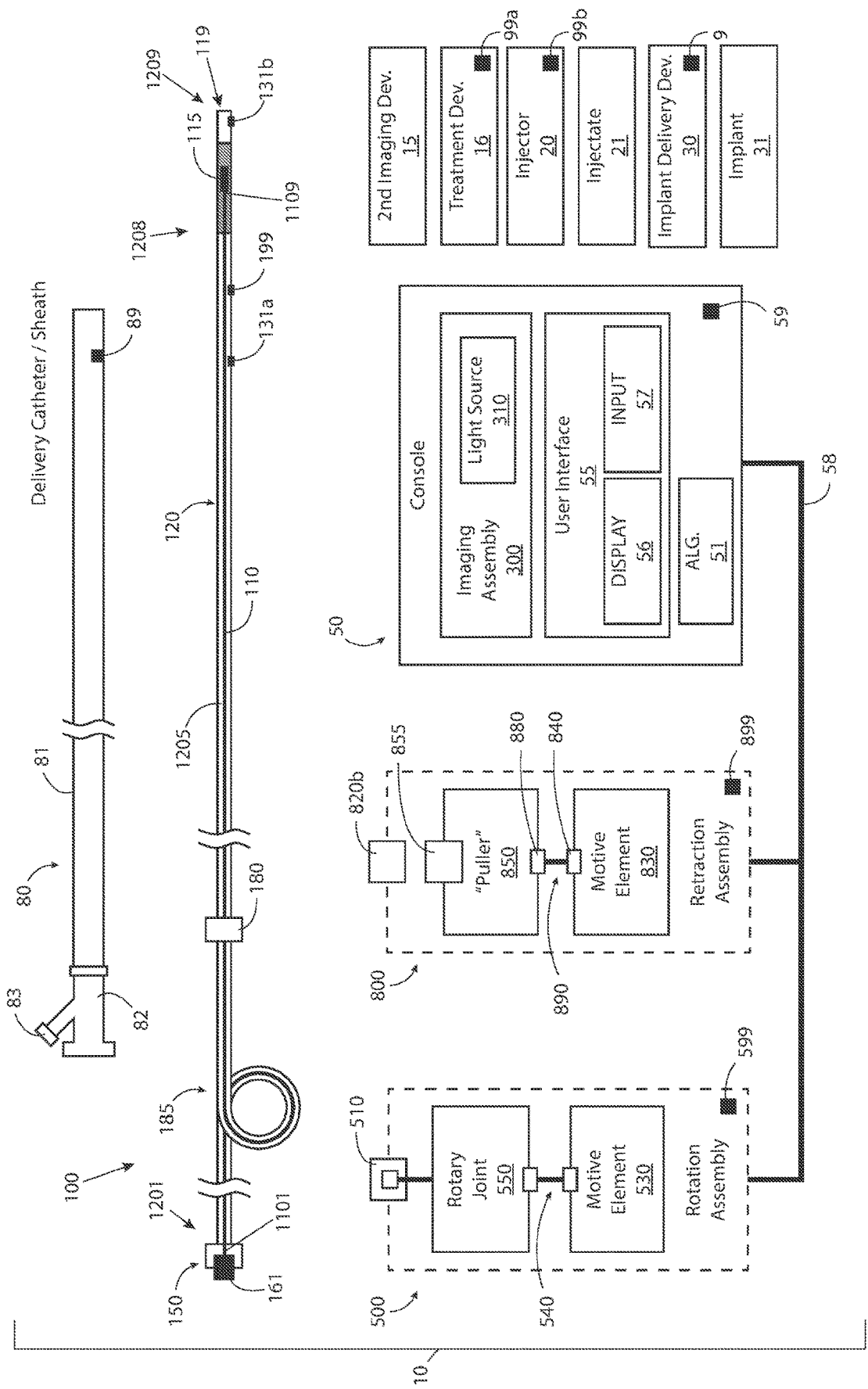
FIG. 1 illustrates a schematic view of an imaging system comprising an imaging probe and independent retraction and rotation assemblies, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element);

positioned on an external and/or internal surface of the second element; and combinations of one or more of these.

As used herein, the term "proximate" shall include locations relatively close to, on, in and/or within a referenced component or other location.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence.

The term "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

In this specification, unless explicitly stated otherwise, "and" can mean "or," and "or" can mean "and." For example, if a feature is described as having A, B, or C, the feature can have A, B, and C, or any combination of A, B, and C. Similarly, if a feature is described as having A, B, and C, the feature can have only one or two of A, B, or C.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure, as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross-sectional area as the cross section of the component being described.

The terms "major axis" and "minor axis" of a component where used herein are the length and diameter, respectively, of the smallest volume hypothetical cylinder which can completely surround the component.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

Provided herein are systems for use in a patient to create an image of the patient's anatomy. The image can comprise a two-dimensional and/or three-dimensional image of the patient's anatomy, and it can further include an image of one or more devices positioned proximate the patient's anatomy being imaged. The systems include an imaging probe, a rotation assembly, and a retraction assembly. The imaging probe collects image data from a patient site and includes an elongate shaft with a proximal end and a distal portion, with a lumen extending therebetween. A rotatable optical core is positioned within the elongate shaft lumen and an optical assembly is positioned in the elongate shaft distal portion. The optical assembly directs light to tissue at the patient site and collects reflected light from the tissue. The rotation assembly connects to the imaging probe and rotates the optical assembly. The retraction assembly connects to the imaging probe and retracts the optical assembly and the elongate shaft in unison.

Referring now to FIG. 1, a schematic view of an imaging system comprising an imaging probe and independent retraction and rotation assemblies is illustrated, consistent with the present inventive concepts. Imaging system 10 is constructed and arranged to collect image data and produce one or more images based on the recorded data, such as when imaging system 10 comprises an Optical Coherence Tomography (OCT) imaging system constructed and arranged to collect image data of an imaging location (e.g.

a segment of a blood vessel, such as during a pullback procedure). Imaging system 10 comprises catheter-based probe, imaging probe 100, as well as a rotation assembly 500 and a retraction assembly 800, each of which can operably attach to imaging probe 100. Imaging system 10 can further comprise console 50 which is configured to operably connect to imaging probe 100, such as via rotation assembly 500 and/or retraction assembly 800. Imaging probe 100 can be introduced into a conduit of the patient, such as a blood vessel or other conduit of the patient, using one or more delivery catheters, for example delivery catheter 80 shown. Alternatively or additionally, imaging probe 100 can be introduced though an introducer device, such as an endoscope, arthroscope, balloon dilator, or the like. In some embodiments, imaging probe 100 is configured to be introduced into a conduit selected from the group consisting of: an artery; a vein; an artery within or proximate the heart; a vein within or proximate the heart; an artery within or proximate the brain; a vein within or proximate the brain; a peripheral artery; a peripheral vein; through a natural body orifice into a conduit, such as the esophagus; through a surgically created orifice into a body cavity, such as the abdomen; and combinations of these. Imaging system 10 can further comprise one or more (additional) imaging devices, such as second imaging device 15 shown. Imaging system 10 can further comprise a device configured to treat the patient, treatment device 16. Imaging system 10 can further comprise a fluid injector, such as injector 20, which can be configured to inject one or more fluids, such as a flushing fluid, an imaging contrast agent (e.g. a radiopaque contrast agent, hereinafter "contrast") and/or other fluid, such as injectate 21 shown. Imaging system 10 can further comprise an implant, such as implant 31, which can be implanted in the patient via a delivery device, such as an implant delivery device 30 and/or delivery catheter 80.

In some embodiments, imaging probe 100 and/or another component of imaging system 10 can be of similar construction and arrangement to the similar components described in applicants co-pending U.S. patent application Ser. No. 15/566,041, titled "Micro-Optic Probes for Neurology", filed Oct. 12, 2017; the content of which is incorporated herein by reference in its entirety for all purposes. Imaging probe 100 can be constructed and arranged to collect image data from a patient site, such as an intravascular cardiac site, an intracranial site, or other site accessible via the vasculature of the patient. In some embodiments, imaging system 10 can be of similar construction and arrangement to the similar systems and their methods of use described in applicants co-pending U.S. patent application Ser. No. 15/751,570, titled "Imaging System includes Imaging Probe and Delivery Devices", filed Feb. 9, 2018; the content of which is incorporated herein by reference in its entirety for all purposes.

Delivery catheter 80 comprises an elongate shaft, shaft 81, with a lumen therethrough, and a connector 82 positioned on its proximal end. Connector 82 can comprise a Touhy or valved connector, such as a valved connector configured to prevent fluid egress from the associated delivery catheter 80 (with and/or without a separate shaft positioned within the connector 82). Connector 82 can comprise a port 83, such as a port constructed and arranged to allow introduction of fluid into delivery catheter 80 and/or for removing fluids from delivery catheter 80. In some embodiments, a flushing fluid, as described herebelow, is introduced via one or more ports 83, such as to remove blood and/or other undesired material from locations proximate optical assembly 115 (e.g. from a location proximal to optical assembly 115 to a location distal to optical assembly 115). Port 83 can be positioned on a side of connector 82 and can include a luer fitting and a cap and/or valve. Shafts 81, connectors 82, and ports 83 can each comprise standard materials and be of similar construction to commercially available introducers, guide catheters, diagnostic catheters, intermediate catheters and microcatheters used in interventional procedures. Delivery catheter 80 can comprise a catheter configured to deliver imaging probe 100 to an intracerebral location, an intracardiac location, and/or another location within a patient.

Imaging system 10 can comprise two or more delivery catheters 80, such as three or more delivery catheters 80. Multiple delivery catheters 80 can comprise at least a vascular introducer, and other delivery catheters 80 that can be inserted into the patient therethrough, after the vascular introducer is positioned through the skin of the patient. Two or more delivery catheters 80 can collectively comprise sets of inner diameters (IDs) and outer diameters (ODs) such that a first delivery catheter 80 slidingly receives a second delivery catheter 80 (e.g. the second delivery catheter OD is less than or equal to the first delivery catheter ID), and the second delivery catheter 80 slidingly receives a third delivery catheter 80 (e.g. the third delivery catheter OD is less than or equal to the second delivery catheter ID), and so on. In these configurations, the first delivery catheter 80 can be advanced to a first anatomical location, the second delivery catheter 80 can be advanced through the first delivery catheter to a second anatomical location distal or otherwise remote (hereinafter "distal") to the first anatomical location, and so on as appropriate, using sequentially smaller diameter delivery catheters 80. In some embodiments, one or more delivery catheters are configured to deliver (e.g. sequentially and/or simultaneously deliver) both imaging probe 100 and a second device (e.g. a second catheter-based device), such as another delivery catheter 80, a second imaging device (e.g. second imaging device 15), a treatment device (e.g. treatment device 16), and/or a coil, stent, and/or other implant delivery device (e.g. implant delivery device 30). In some embodiments, delivery catheters 80 can be of similar construction and arrangement to the similar components described in applicants co-pending U.S. patent application Ser. No. 15/751,570, titled "Imaging System includes Imaging Probe and Delivery Devices", filed Feb. 9, 2018; the content of which is incorporated herein by reference in its entirety for all purposes.

Imaging probe 100 comprises an elongate body, comprising one or more elongate shafts and/or tubes, elongate shaft 120 herein. Shaft 120 comprises a proximal end 1201, distal end 1209, and a lumen 1205 extending therebetween. In some embodiments, lumen 1205 includes multiple coaxial lumens within the one or more elongate shafts 120, such as one or more lumens abutting each other to define a single lumen 1205. Shaft 120 further comprises a distal portion 1208. Shaft 120 construction is described herebelow in reference to FIGS. 2 and 2A-C. Shaft 120 operably surrounds a rotatable optical fiber, optical core 110 (e.g. optical core 110 is positioned within lumen 1205), comprising a proximal end 1101 and a distal end 1109. An optical assembly, optical assembly 115, is positioned on the distal end 1109 of optical core 110. A connector assembly, connector assembly 150, is positioned on the proximal end of shaft 120. Connector assembly 150 operably attaches imaging probe 100 to rotation assembly 500, as described herein. Connector assembly 150 surrounds and operably attaches to an optical connector 161, fixedly attached to the proximal end of optical core 110. In some embodiments, connector assembly 150, including optical connector 161, can be of similar construction and arrangement to those described herebelow in reference to FIGS. 3 and 3A-G. A second connector, pullback connector 180, is positioned on shaft 120. Connector 180 can be removably attached and/or adjustably positioned along the length of shaft 120. Connector 180 can be positioned along shaft 120, such as by an operator, proximate the proximal end of delivery catheter 80 after imaging probe 100 has been inserted into a patient via delivery catheter 80. Shaft 120 can comprise a portion between connector assembly 150 and the placement location of connector 180 that accommodates slack in shaft 120, a proximal portion of shaft 120 (e.g. a proximal portion of imaging probe 100), service loop 185.

Imaging probe 100 can comprise one or more visualizable markers along its length (e.g. along shaft 120), markers 131a-b shown (marker 131 herein). Marker 131 can comprise markers selected from the group consisting of: radiopaque markers; ultrasonically reflective markers; magnetic markers; ferrous material; and combinations of these. In some embodiments, marker 131 comprises a marker positioned at a location (e.g. a location within and/or at least proximate distal portion 120B) to assist an operator of imaging system 10 in performing a pullback procedure, such as to cause tip 119 to be positioned at a location distal to the proximal end of an implant after the pullback is completed (e.g. so that imaging probe 100 can be safely advanced through the implant after the pullback).

Rotation assembly 500 comprises a connector assembly 510, operably attached to a rotary joint 550. Rotation assembly 500 further comprises a motor or other rotational energy source, motive element 530. Motive element 530 is operably attached to rotary joint 550 via a linkage assembly 540. In some embodiments, linkage assembly 540 comprises one or more gears, belts, pulleys, or other force transfer mechanisms, such as described herebelow in reference to FIGS. 5A-D. Motive element 530 can drive (e.g. rotate via linkage assembly 540) rotary joint 550 (and in turn core 110) at speeds of at least 100 rotations per second, such as at least 200 rotations per second or 250 rotations per second, or between 20 rotations per second and 1000 rotations per second. Motive element 530 can comprise a mechanism selected from the group consisting of: a motor; a servo; a stepper motor (e.g. a stepper motor including a gear box); a linear actuator; a hollow core motor; and combinations of these.

Connector assembly 510 operably attaches to connector assembly 150 of imaging probe 100, allowing optical connector 161 to operably engage rotary joint 550. In some embodiments, connector assembly 510 operably engages connector assembly 150, as described herebelow in reference to FIGS. 5A-D. In some embodiments, connector assembly 510 operably engages connector assembly 150 such that rotary joint 550 and optical connector 161 are free to rotate within the engaged assemblies.

Retraction assembly 800 comprises a connector assembly 820, that operably attaches to a reference point, for example connector 82 of delivery catheter 80, such as to establish a reference for retraction assembly 800 relative to the patient. Connector assembly 820 can attach to a reference point such as a patient introduction device, surgical table, and/or another fixed or semi-fixed point of reference. A retraction element, puller 850, releasably attaches to connector 180 of imaging probe 100, such as via a carrier 855. Retraction assembly 800 retracts at least a portion of imaging probe 100 (e.g. the portion of imaging probe 100 distal to the attached connector 180), relative to the established reference. Service loop 185 of imaging probe 100 can be positioned between retraction assembly 800 and/or at least connector assembly 820, and rotation assembly 500, such that imaging probe 100 can be retracted relative to the patient while rotation assembly 500 remains stationary (e.g. attached to the surgical table and/or to a portion of console 50).

Retraction assembly 800 further comprises a linear drive, motive element 830. In some embodiments, motive element 830 comprises a linear actuator, a worm drive operably attached to a motor, a pulley system, and/or other linear force transfer mechanisms. In some embodiments, motive element 830 can be of similar construction and arrangement to motive element 830 described herebelow in reference to FIG. 9. Puller 850 can be operably attached to motive element 830 via a linkage assembly 890. In some embodiments, linkage assembly 890 comprises one or more components of a "pullback assembly", as described herebelow in reference to FIGS. 1A, 7A-C and 8A-C. Alternatively or additionally, linkage assembly 890 can comprise one or more components of an enclosed pullback connector, as described herebelow in reference to FIGS. 1B and 10A-B. One or more components of linkage assembly 890 can establish a frame of reference (e.g. an internal pullback reference) between puller 850 and the motive element 830, such that motive element 830 applies a pullback force to puller 850 via linkage assembly 890, and puller 850 retracts relative to the distal portion of linkage assembly 890 (e.g. relative to the distal end of sheath 895), as described herebelow. In some embodiments, the distal end of linkage assembly 890 and connector assembly 820 are fixed relative to each other, and puller 850 translates linearly between the two in reaction to a force applied from motive element 830.

Console 50 comprises an imaging assembly 300, a user interface 55, and one or more algorithms 51. Imaging assembly 300 can be configured to provide light to optical assembly 115 (e.g. via optical core 110) and collect light from optical assembly 115 (e.g. via optical core 110). Imaging assembly 300 can include a light source 310 configured to provide the light to optical assembly 115. Light source 310 can comprise one or more light sources, such as one or more light sources configured to provide one or more wavelengths of light to optical assembly 115 via optical core 110. Light source 310 is configured to provide light to optical assembly 115 (e.g. via optical core 110) such that image data can be collected (e.g. reflected light is collected by an opto-electronic module of optical assembly 115 that is configured to collect and analyze light returned from optical assembly 115). The collected image data can comprise cross-sectional, longitudinal and/or volumetric information related to a patient site and/or implanted device being imaged. Light source 310 can be configured to provide light such that the image data collected includes characteristics of tissue within the patient site being imaged, such as to quantify, qualify or otherwise provide information related to a patient disease or disorder present within the patient site being imaged. Light source 310 can be configured to deliver broadband light and have a center wavelength in the range from 800 nm to 1700 nm, such as from 1280 nm and 1310 nm, or such as approximately 1300 nm (e.g. light delivered with a sweep range from 1250 nm to 1350 nm). The light source 310 bandwidth can be selected to achieve a desired resolution, which can vary according to the needs of the intended use of imaging system 10. In some embodiments, bandwidths are about 5% to 15% of the center wavelength, which allows resolutions of between 20 microns and 5 microns. Light source 310 can be configured to deliver light at a power level meeting ANSI Class 1 ("eye safe") limits;

higher power levels can be employed. In some embodiments, light source 310 delivers light in the 1.3 μm band at a power level of approximately 20 mW. Tissue light scattering is reduced as the center wavelength of delivered light increases, and water absorption increases. Light source 310 can deliver light at a wavelength approximating 1300 nm to balance these two effects. Light source 310 can be configured to deliver shorter wavelength light (e.g. approximately 800 nm light) to traverse patient sites to be imaged including large amounts of fluid. Alternatively or additionally, light source 310 can be configured to deliver longer wavelengths of light (e.g. approximately 1700 nm light), such as to reduce a high level of scattering within a patient site to be imaged. In some embodiments, light source 310 comprises a tunable light source (e.g. light source 310 emits a single wavelength that changes repetitively over time), and/or a broad-band light source. Light source 310 can comprise a single spatial mode light source or a multimode light source (e.g. a multimode light source with spatial filtering).

Console 50 can comprise an algorithm, such as algorithm 51 shown, which can be configured to adjust (e.g. automatically and/or semi-automatically adjust) one or more operational parameters of imaging system 10, such as an operational parameter of console 50, imaging probe 100 and/or a delivery catheter 80. Alternatively or additionally, algorithm 51 can be configured to adjust an operational parameter of a separate device, such as injector 20 or implant delivery device 30 described herebelow. In some embodiments, algorithm 51 is configured to adjust an operational parameter based on one or more sensor signals, such as a sensor signal provided by a sensor-based functional element of the present inventive concepts, as described herein. Algorithm 51 can be configured to adjust an operational parameter selected from the group consisting of: a rotational parameter such as rotational velocity of optical core 110 and/or optical assembly 115; a retraction parameter of shaft 120 and/or optical assembly 115, such as retraction velocity, distance, start position, end position and/or retraction initiation timing (e.g. when retraction is initiated); a position parameter, such as position of optical assembly 115; a line spacing parameter, such as lines per frame; an image display parameter, such as a scaling of display size to vessel diameter; an imaging probe 100 configuration parameter; an injectate 21 parameter, such as a saline to contrast ratio configured to determine an appropriate index of refraction; a light source 310 parameter, such as power delivered and/or frequency of light delivered; and combinations of these. In some embodiments, algorithm 51 is configured to adjust a retraction parameter, such as a parameter triggering the initiation of the pullback, such as a pullback that is initiated based on a parameter selected from the group consisting of: lumen flushing (the lumen proximate optical assembly 115 has been sufficiently cleared of blood or other matter that would interfere with image creation); an indicator signal is received from injector 20 (e.g. a signal indicating sufficient flushing fluid has been delivered); a change in image data collected (e.g. a change in an image is detected, based on the image data collected, that correlates to proper evacuation of blood from around optical assembly 115); and combinations of these. In some embodiments, algorithm 51 is configured to adjust an imaging system 10 configuration parameter related to imaging probe 100, such as when algorithm 51 identifies (e.g. automatically identifies via an RF or other embedded ID) the attached imaging probe 100 and adjusts an imaging system 10 parameter, such as an arm path length parameter, a dispersion parameter, and/or other parameter as listed above.

Imaging system 10 can comprise one or more interconnect cables, bus 58 shown. Bus 58 can operably connect rotation assembly 500 to console 50, retraction assembly 800 to console 50, and or rotation assembly 500 to retraction assembly 800. Bus 58 can comprise one or more optical transmission fibers, electrical transmission cables, fluid conduits, and combinations of these. In some embodiments, bus 58 comprises at least an optical transmission fiber that optically couples rotary joint 550 to imaging assembly 300 of console 50. Alternatively or additionally, bus 58 comprises at least power and/or data transmission cables that transfer power and/or motive information to one or more of motive elements 530 and 830.

Second imaging device 15 can comprise an imaging device such as one or more imaging devices selected from the group consisting of: an X-ray; a fluoroscope, such as a single plane or biplane fluoroscope; a CT Scanner; an MRI; a PET Scanner; an ultrasound imager; and combinations of these. In some embodiments, a clinician uses images provided by imaging device 15 in combination with images provided by probe 100. In some embodiments, system 10 provides image processing to combine images provided by probe 100 and images provided by second imaging device 15 (e.g. co-register and/or digitally combined images based on data provided by probe 100 and device 15). In some embodiments, second imaging device 15 comprises a device configured to perform rotational angiography. In these embodiments, system 10 can provide combined images including rotational angiography images and probe 100 derived images.

Treatment device 16 can comprise an occlusion treatment device or other treatment device selected from the group consisting of: a balloon catheter constructed and arranged to dilate a stenosis or other narrowing of a blood vessel; a drug eluting balloon; an aspiration catheter; a sonolysis device; an atherectomy device; a thrombus removal device such as a stent retriever device; a Trevo™ stentriever; a Solitaire™ stentriever; a Revive™ stentriever; an Eric™ stentriever; a Lazarus™ stentriever; a stent delivery catheter; a microbraid implant; an embolization system; a WEB™ embolization system; a Luna™ embolization system; a Medina™ embolization system; and combinations of these. In some embodiments, imaging probe 100 is configured to collect data related to treatment device 16 (e.g. treatment device 16 location, orientation, and/or other configuration data), after treatment device 16 has been inserted into the patient.

Injector 20 can comprise a power injector, syringe pump, peristaltic pump or other fluid delivery device configured to inject a contrast agent, such as radiopaque contrast, and/or other fluids. In some embodiments, injector 20 is configured to deliver contrast and/or other fluid (e.g. contrast, saline and/or Dextran). In some embodiments, injector 20 delivers fluid in a flushing procedure as described herebelow. In some embodiments, injector 20 delivers contrast or other fluid through a delivery catheter 80 with an ID of between 5 Fr and 9 Fr, a delivery catheter 80 with an ID of between 0.53" to 0.70", or a delivery catheter 80 with an ID between 0.0165" and 0.027". In some embodiments, contrast or other fluid is delivered through a delivery catheter as small as 4 Fr (e.g. for distal injections). In some embodiments, injector 20 delivers contrast and/or other fluid through the lumen of one or more delivery catheters 80, while one or more smaller delivery catheters 80 also reside within the lumen. In some embodiments, injector 20 is configured to deliver two dissimilar fluids simultaneously and/or sequentially, such as a first fluid delivered from a first reservoir and comprising a first concentration of contrast, and a second fluid from a second reservoir and comprising less or no contrast.

Injectate 21 can comprise fluid selected from the group consisting of: optically transparent material; saline; visualizable material; contrast; Dextran; an ultrasonically reflective material; a magnetic material; and combinations of these. Injectate 21 can comprise contrast and saline. Injectate 21 can comprise at least 20% contrast. During collection of image data, a flushing procedure can be performed, such as by delivering one or more fluids, injectate 21 (e.g. as propelled by injector 20 or other fluid delivery device), to remove blood or other somewhat opaque material (hereinafter non-transparent material) proximate optical assembly 115 (e.g. to remove non-transparent material between optical assembly 115 and a delivery catheter and/or non-transparent material between optical assembly 115 and a vessel wall), such as to allow light distributed from optical assembly 115 to reach and reflectively return from all tissue and other objects to be imaged. In these flushing embodiments, injectate 21 can comprise an optically transparent material, such as saline. Injectate 21 can comprise one or more visualizable materials, as described herebelow.

As an alternative or in addition to its use in a flushing procedure, injectate 21 can comprise material configured to be viewed by second imaging device 15, such as when injectate 21 comprises a contrast material configured to be viewed by a second imaging device 15 comprising a fluoroscope or other X-ray device; an ultrasonically reflective material configured to be viewed by a second imaging device 15 comprising an ultrasound imager; and/or a magnetic material configured to be viewed by a second imaging device 15 comprising an MRI.

Implant 31 can comprise an implant (e.g. a temporary or chronic implant) for treating one or more of a vascular occlusion or an aneurysm. In some embodiments, implant 31 comprises one or more implants selected from the group consisting of: a flow diverter; a Pipeline™ flow diverter; a Surpass™ flow diverter; an embolization coil; a stent; a Wingspan™ stent; a covered stent; an aneurysm treatment implant; and combinations of these.

Implant delivery device 30 can comprise a catheter or other tool used to deliver implant 31, such as when implant 31 comprises a self-expanding or balloon expandable portion. In some embodiments, imaging system 10 comprises imaging probe 100, one or more implants 31 and/or one or more implant delivery devices 30. In some embodiments, imaging probe 100 is configured to collect data related to implant 31 and/or implant delivery device 30 (e.g. implant 31 and/or implant delivery device 30 anatomical location, orientation and/or other configuration data), after implant 31 and/or implant delivery device 30 has been inserted into the patient, such as is described in reference to FIG. 12 herebelow.

In some embodiments, one or more system components, such as console 50, delivery catheter 80, imaging probe 100, rotation assembly 500, retraction assembly 800, treatment device 16, injector 20, and/or implant delivery device 30, further comprise one or more functional elements ("functional element" herein), such as functional elements 59, 89, 199, 599, 899, 99a, 99b, and/or 99c, respectively, shown. Each functional element can comprise at least two functional elements. Each functional element can comprise one or more elements selected from the group consisting of: sensor; transducer; and combinations of these. The functional element can comprise a sensor configured to produce a signal. The functional element can comprise a sensor selected from the group consisting of: a physiologic sensor; a pressure sensor; a strain gauge; a position sensor; a GPS sensor; an accelerometer; a temperature sensor; a magnetic sensor; a chemical sensor; a biochemical sensor; a protein sensor; a flow sensor, such as an ultrasonic flow sensor; a gas detecting sensor, such as an ultrasonic bubble detector; a sound sensor, such as an ultrasound sensor; and combinations of these. The sensor can comprise a physiologic sensor selected from the group consisting of: a pressure sensor, such as a blood pressure sensor; a blood gas sensor; a flow sensor, such as a blood flow sensor; a temperature sensor, such as a blood or other tissue temperature sensor; and combinations of these. The sensor can comprise a position sensor configured to produce a signal related to a vessel path geometry (e.g. a 2D or 3D vessel path geometry). The sensor can comprise a magnetic sensor. The sensor can comprise a flow sensor. The system can further comprise an algorithm configured to process the signal produced by the sensor-based functional element. Each functional element can comprise one or more transducers. Each functional element can comprise one or more transducers selected from the group consisting of: a heating element, such as a heating element configured to deliver sufficient heat to ablate tissue; a cooling element, such as a cooling element configured to deliver cryogenic energy to ablate tissue; a sound transducer, such as an ultrasound transducer; a vibrational transducer; and combinations of these.

As described herein, retraction assembly 800 and rotation assembly 500 can be constructed and arranged to independently perform a retraction operation and a rotation operation, respectively. For example, retraction assembly 800 can be configured to independently retract at least a portion of imaging probe 100, with or without simultaneous rotation of optical core 110. Rotation assembly 500 can be configured to independently rotate optical core 110, with or without simultaneous retraction of probe 100. Additionally or alternatively, retraction assembly 800 and rotation assembly 500 can comprise separate (discrete) components that can be positioned independently. For example, retraction assembly 800 can be constructed and arranged such that it imparts no tensile forces and/or other forces, on rotation assembly 500 (e.g. retraction assembly 800 does not cause nor require rotation assembly 500 to retract or otherwise move during retraction of probe 100). Alternatively or additionally, rotation assembly 500 can be constructed and arranged such that it imparts no rotational forces and/or other forces, on retraction assembly 800 (e.g. rotation assembly 500 does not cause nor require retraction assembly 800 to rotate or otherwise move during rotation of optical core 110).

Figure 1A:
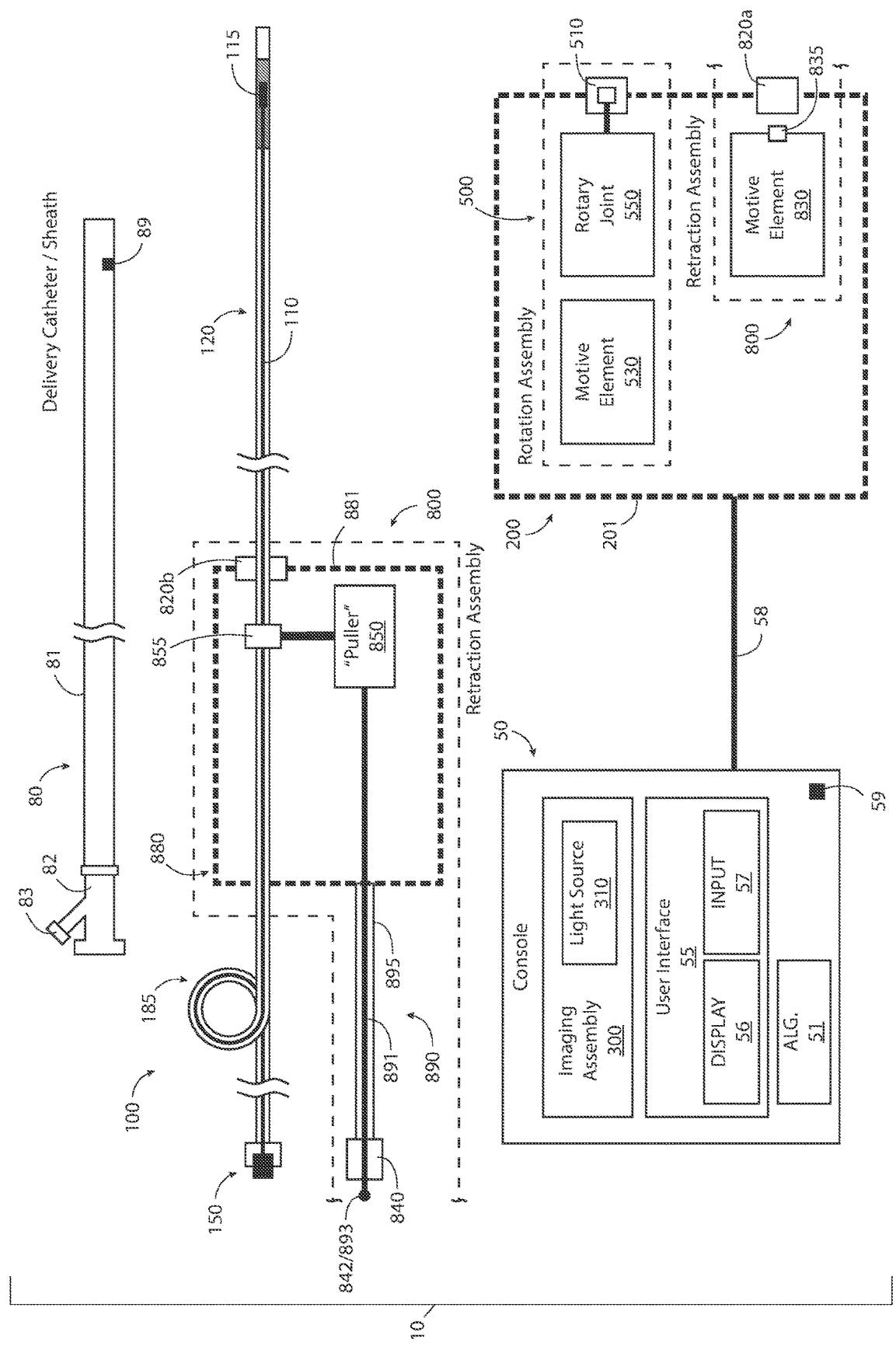
FIG. 1A illustrates a schematic view of an imaging system comprising an imaging probe operably attachable to a patient interface module, and an independent pullback module operably attachable to the patient interface module and the imaging probe, consistent with the present inventive concepts.

Referring now to FIG. 1A, a schematic view of an imaging system is illustrated, the system comprising an imaging probe operably attachable to a patient interface module, and an independent pullback module operably attachable to the patient interface module and the imaging probe, consistent with the present inventive concepts. Imaging system 10 can comprise a patient interface module 200. Patient interface module 200 comprises a housing, housing 201, surrounding at least a portion of rotation assembly 500, and at least a portion of retraction assembly 800. Imaging system 10 can further comprise a second, discrete component, pullback module 880. Pullback module 880 comprises a housing, housing 881, surrounding at least a portion of retraction assembly 800. Pullback module 880 and patient interface module 200 can be operably attached to each other via a connector assembly, linkage assembly 890 described herein. Pullback module 880 and patient interface module 200 can be constructed and arranged (e.g. via each having a separate housing) to enable positioning at different locations (e.g. linkage assembly 890 connecting modules 880 and 200 can comprise a length of at least 15 cm such that the two remote locations can be at least 15 cm apart). For example, patient interface module 200 can be positioned on or near a surgical bed rail, and pullback module 880 can be positioned near a vascular access site of the patient (e.g. within 30 cm of the vascular access site thru which imaging probe 100 enters the patient). Linkage assembly 890 can comprise a linkage 891 slidingly received within sheath 895. Linkage 891 is operably attached to puller 850, and the proximal end 893 of linkage 891 can comprise a connection point, 842. Components shown in FIG. 1A can be of similar construction and arrangement to like components described in FIG. 1 hereabove, and elsewhere herein.

Pullback module 880 and its associated components can be of similar construction and arrangement to pullback module 880 described herebelow in reference to FIGS. 7A-8C. Housing 881 and its associated components can be of similar construction and arrangement to housing 881 described herebelow in reference to FIGS. 8A-C. Connector assembly 845 and its associated components can be of similar construction and arrangement to connector assembly 845 described herebelow in reference to FIG. 7A-B. Pullback module 880 can comprise a connector assembly 820b that operably attaches to connector 82 of delivery catheter 80, such as described herebelow in reference to FIGS. 8A-C. Connector assembly 845 can comprise a connector 840 that operably attaches to a connector assembly 820a of patient interface module 200, as described herebelow in reference to FIGS. 4A-C. Imaging probe 100 can comprise a connector assembly 150 that operably attaches to a connector assembly 510 of patient interface module 200, as described herebelow in reference to FIGS. 4A-C.

Figure 1B:
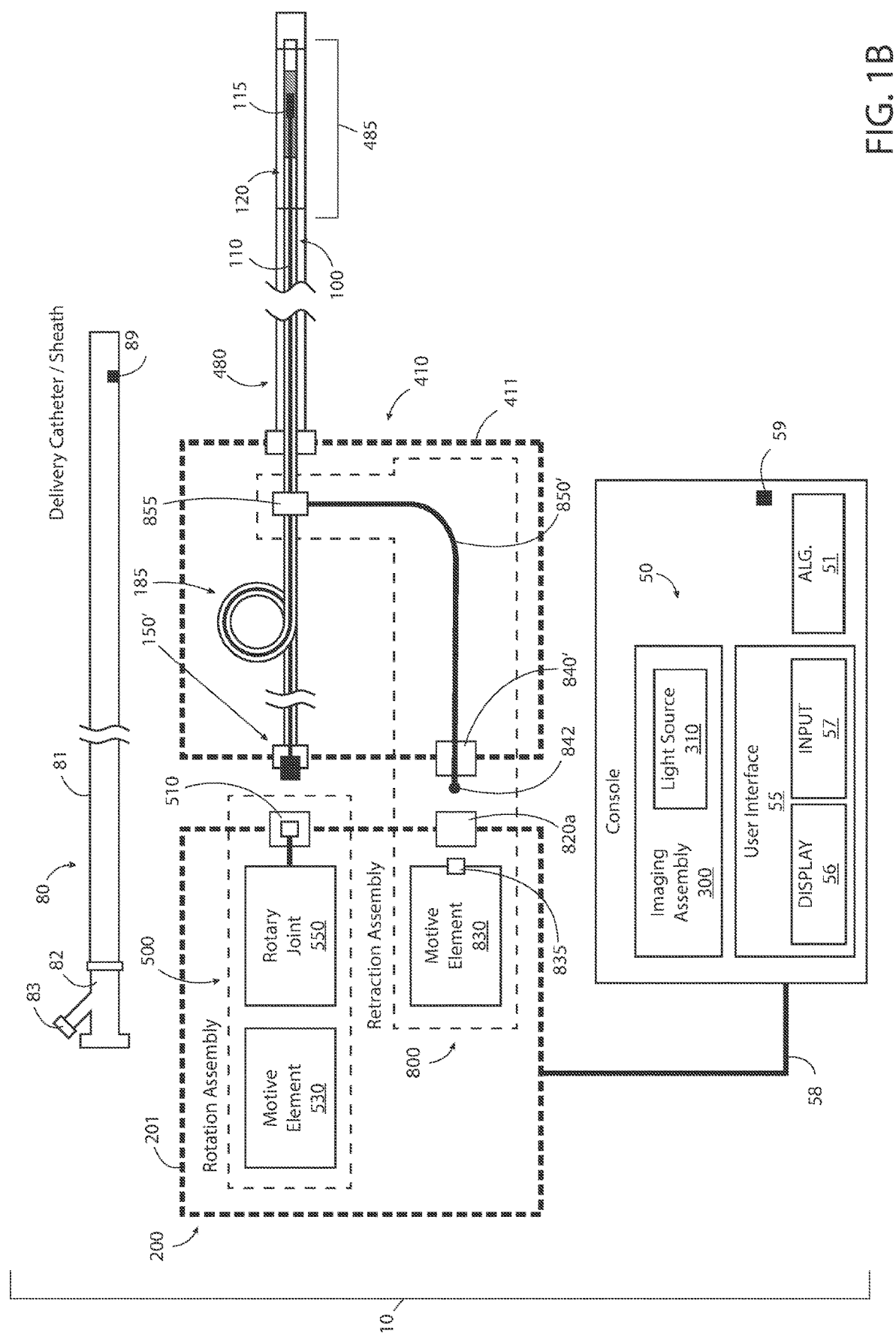
FIG. 1B illustrates a schematic view of an imaging system comprising an imaging probe operably attachable to a module comprising a first connector for attaching to a rotation motive element and a second connector for attaching to a retraction motive element, consistent with the present inventive concepts.

Referring now to FIG. 1B, a schematic view of an imaging system is illustrated, the system comprising an imaging probe operably attachable to a module comprising a first connector for attaching to a rotation motive element and a second connector for attaching to a retraction motive element, consistent with the present inventive concepts. Imaging system 10 can comprise a patient interface module 200, as described herein. Imaging system 10 can further comprise a connector module, module 410. Module 410 comprises a housing, housing 411, surrounding at least a portion of retraction assembly 800, service loop 185 of imaging probe 100, connector assembly 150', and connector 840'. Module 410 can be configured to operably attach both imaging probe 100 and a linkage, puller 850', to patient interface module 200, and can be of similar construction and arrangement to module 410 and its associated components (e.g. delivery catheter 480 which includes window 485) described herebelow in reference to FIGS. 10A-B. Components shown in FIG. 1B can be of similar construction and arrangement to like components described in FIG. 1 hereabove, and elsewhere herein.

Figure 2:
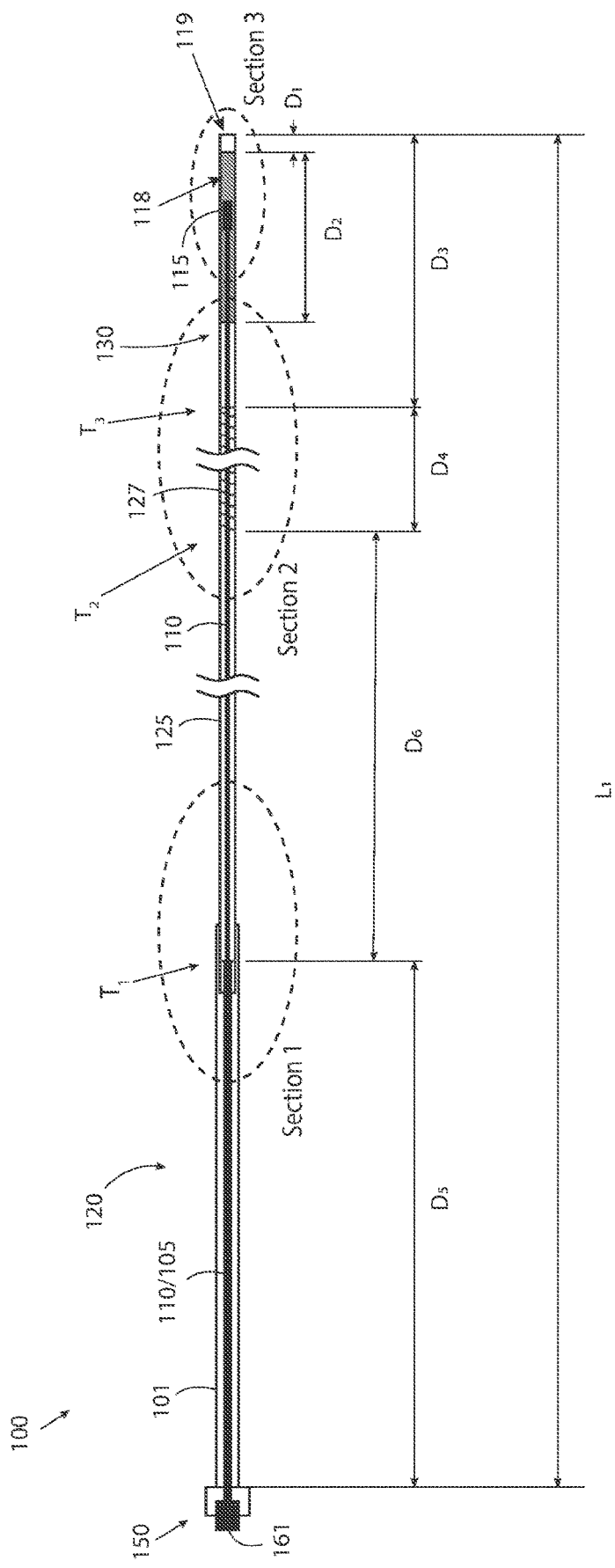
FIG. 2 illustrates a schematic view of an optical probe, consistent with the present inventive concepts.

Referring now to FIG. 2, a schematic view of an optical probe is illustrated, consistent with the present inventive concepts. Imaging probe 100 can comprise an elongate body, including one or more elongate shafts along its length, surrounding optical core 110, for example a rotatable core comprising an optical fiber, which is configured to transmit light. Collectively, the one or more elongate shafts may be referred to herein as shaft 120. Optical core 110 can comprise a non-zero dispersion shifted (NZDS) fiber, for example a fiber in which the dispersion of the fiber is shifted away from a natural dispersion zero of approximately 1300 nm. In these embodiments, imaging system 10 can operate such that the system uses optically matched dispersion where the total dispersion of optical components within console 50 matches the optical core 110 (e.g. a NZDS fiber) dispersion in the desired wavelength operation range. Alternatively or additionally, algorithm 51 can detect and numerically correct any dispersion mismatches between console 50 and optical core 110. Optical core 110 can comprise a fiber with a pure silica core, and a low index, or "depressed", cladding. Optical core 110 can comprise a low bend loss fiber, such as less than 5% transmission loss at a minimum radius of less than or equal to 6 mm, and/or less than 30% transmission loss at a minimum radius of less than or equal to 3 mm. Optical core 110 can also comprise a radiation resistant fiber, capable of maintaining its optical transmission properties after radiation exposure, such as exposure from a radiation-based sterilization process. In some embodiments, imaging probe 100 is sterilized using E-beam sterilization. In these embodiments, materials used in optical core 110 can be selected that are compatible with (e.g. not damaged by) E-beam sterilization. For example, optical core 110 can comprise an acrylate coating which is compatible with E-beam sterilization. Optical core 110 can comprise a single mode fiber similar to those used in telecommunication applications. Optical core 110 can comprise a diameter (e.g. a diameter including cladding) of less than 130 microns, such as a diameter less than 85 microns, such as diameter of approximately 80 microns. In some embodiments, optical core 110 comprises at least a first portion comprising an NZDS fiber and/or a depressed cladding optical fiber, and at least a second portion comprising an optical fiber comprising differing optical properties (e.g. a non-shifted optical fiber). Optical core 110 can comprise an optical fiber with an outer diameter (e.g. including cladding) of less than or equal to 120 microns, such as less than or equal to 80 microns. In some embodiments, optical core 110 comprises a silica core with a diameter of approximately 6 μm, with a circumferential cladding with a thickness of approximately 37 μm, and a circumferential polyimide and/or acrylate coating, such as a coating with a thickness of approximately 10 μm.

Connector assembly 150 is positioned at a proximal portion of imaging probe 100 (e.g. a proximal portion of imaging probe 100 terminates at connector assembly 150), and optical core 110 is operably attached to fiber optic connector 161 of connector assembly 150. A rotatable first shaft, torque shaft 105, surrounds a proximal portion of optical core 110, and extends from connector assembly 150 distally to a first shaft transition point $T_1$. An outer second shaft, outer shaft 101, surrounds torque shaft 105 and a proximal portion of optical core 110, and extends from connector assembly 150, distally to the first shaft transition point $T_1$. Torque shaft 105 can comprise a length of approximately 100 cm, such as when imaging probe 100 comprises a length of approximately 300 cm. As described herebelow in reference to FIG. 2A, one or more components (e.g. intermediate shafts) can be used to operably connect, join, align, or otherwise transition from outer shaft 101 to an intermediate third shaft, shaft 125. Shaft 125 extends distally from the first transition point $T_1$, past a second transition point $T_2$, to a third transition point $T_3$. In some embodiments, shaft 125 comprises a segment configured to have a greater flexibility than the remainder of shaft 125, such as a segment including a spiral cut or other flexibility-enhancing feature, segment 127 shown. Segment 127 extends from the second transition point $T_2$ distally to the third transition point $T_3$. In some embodiments, segment 127 comprises a braided or other flexible construction.

Figure 2A:
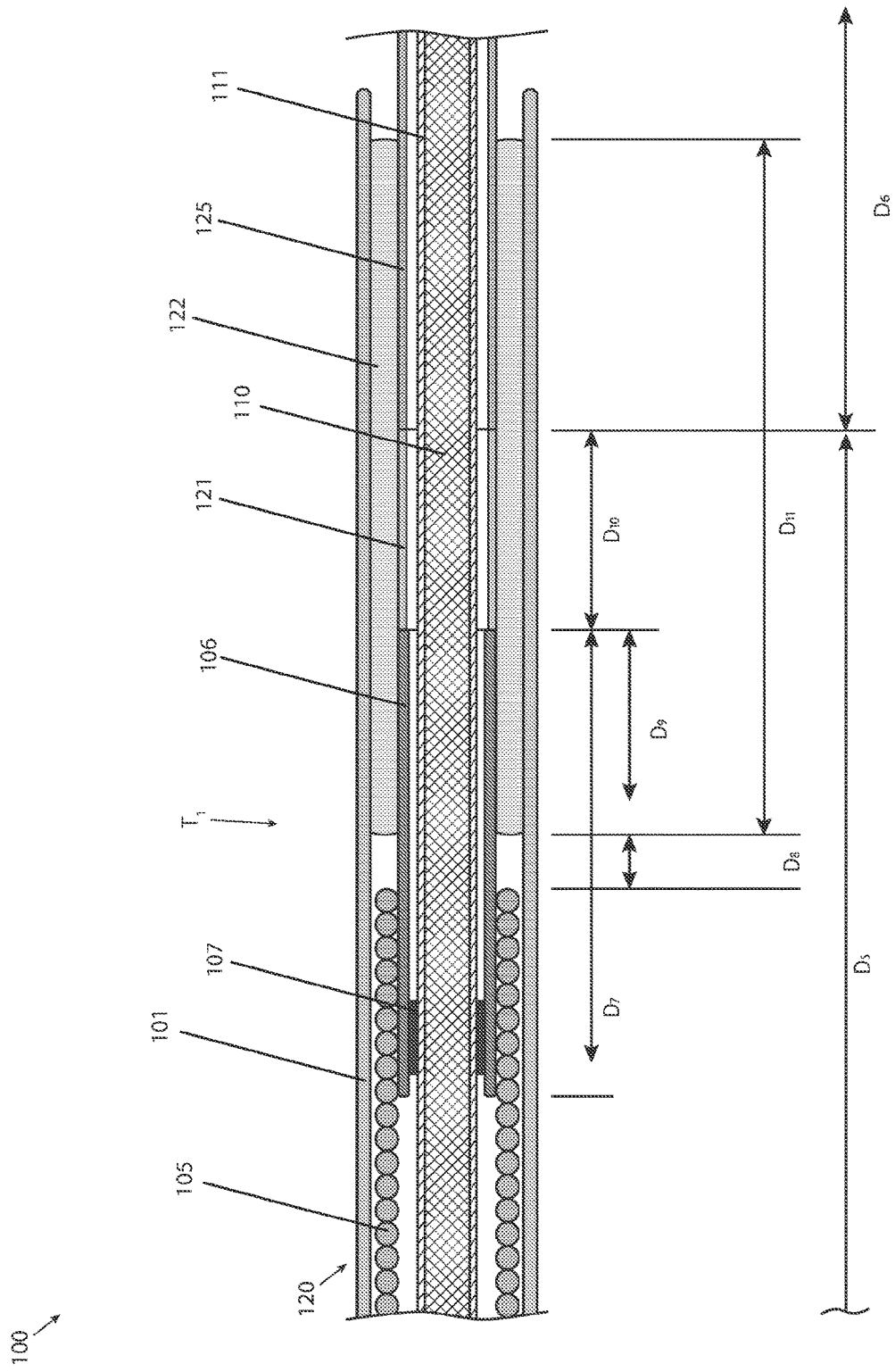
FIG. 2A illustrates a magnified view of transition T1, consistent with the present inventive concepts.
Figure 2B:
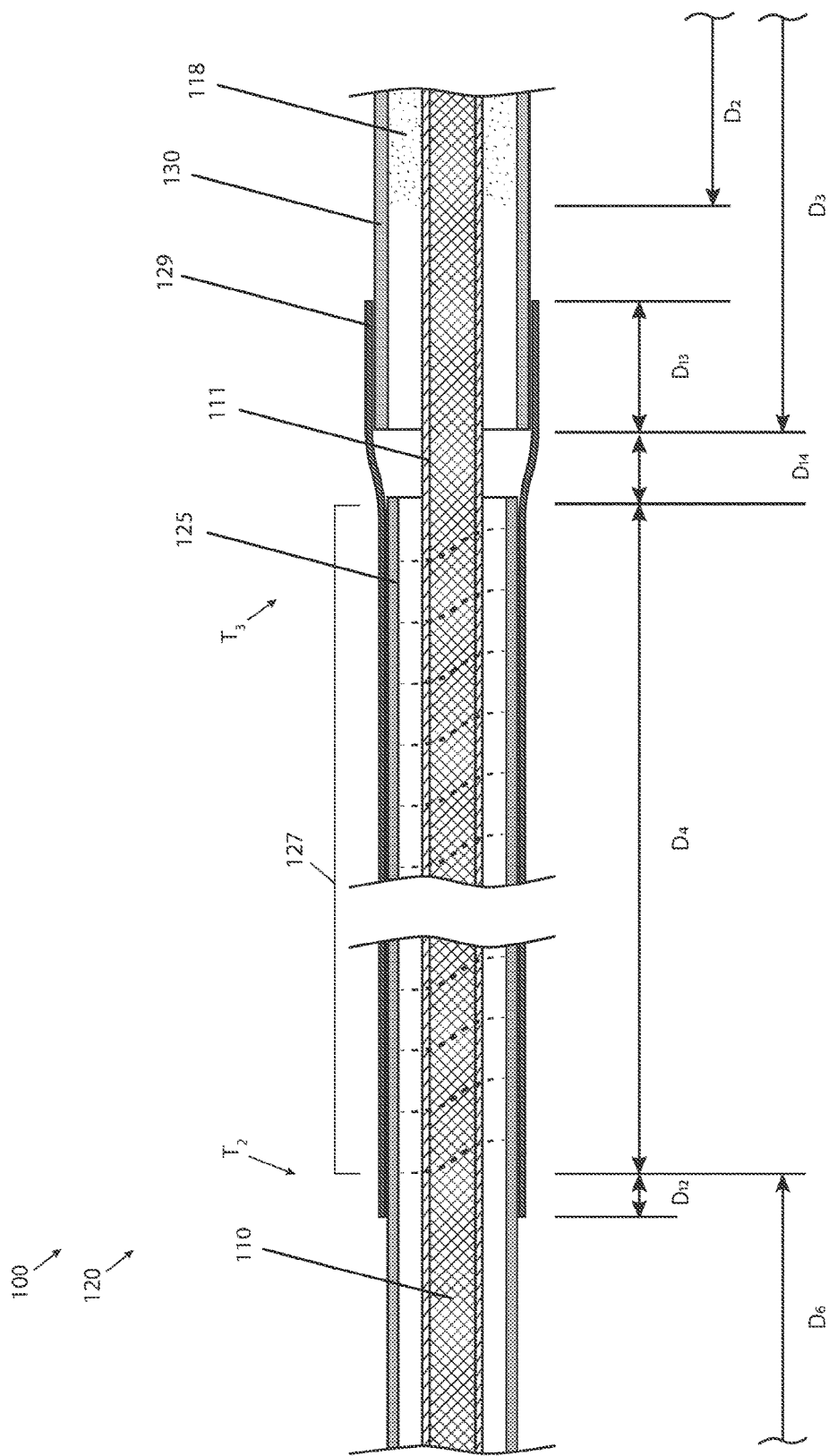
FIG. 2B illustrates a magnified view of transitions T2 and T3, consistent with the present inventive concepts.

As described herebelow in reference to FIG. 2B, one or more components (e.g. an outer shaft or covering) can surround segment 127, such as to prevent fluid ingress into shaft 125 via segment 127. Also described in reference to FIG. 2B, one or more components (e.g. intermediate shafts) can be used to operably connect, join, align, or otherwise transition from shaft 125 to a distal fourth shaft, window 130. Window 130 extends distally, from the third transition point T$_3$ to the distal end of imaging probe 100. Window 130 can comprise a length D3. D3 can comprise a length greater than 225 mm and/or less than 450 mm, such as a length of 250 mm.

In some embodiments, imaging probe 100 includes a viscous dampening material, gel 118, injected (or otherwise installed in a manufacturing process) into the distal portion of window 130. Gel 118 can comprise a non-Newtonian fluid, for example a sheer thinning fluid. In some embodiments, gel 118 comprises a static viscosity of greater than 500 centipoise, and a sheer viscosity of less than the static viscosity. In these embodiments, the ratio of static viscosity to sheer viscosity of gel 118 can be between 1.2:1 and 100:1. Gel 118 surrounds the distal portion of optical core 110, including optical assembly 115. In some embodiments, gel 118 is installed a distance D2 into window 130 (e.g. D2 represents the distance between the proximal end of gel 118 and the distal end of gel 118 within window 130). In some embodiments, D2 comprises a length greater than 175 mm and/or less than 400 mm, such as a length of 200 mm. Gel 118 can comprise a gel as described in reference to applicants co-pending U.S. patent application Ser. No. 15/566,041, titled "Micro-Optic Probes for Neurology", filed Oct. 12, 2017, the content of which is incorporated herein by reference in its entirety for all purposes.

Imaging probe 100 can include a distal tip portion, distal tip 119. In some embodiments, distal tip 119 comprises a spring tip, configured to improve the "navigability" of imaging probe 100 (e.g. to improve "trackability" and/or "steerability" of imaging probe 100), for example within a tortuous pathway. In some embodiments, tip 119 comprises a length of between 5 mm and 100 mm. Alternatively or additionally, tip 119 can comprise a cap or plug, configured to seal the distal opening of window 130. In some embodiments, tip 119 comprises a radiopaque marker, configured to increase the visibility of imaging probe 100 under an X-ray or fluoroscope. In some embodiments, tip 119 comprises a "rapid exchange" type tip.

In some embodiments, at least the distal portion of imaging probe 100 (e.g. the distal portion of shaft 120) comprises an outer diameter of no more than 0.020", or no more than 0.016".

In some embodiments, imaging probe 100 can be constructed and arranged for use in an intravascular neural procedure (e.g. a procedure in which the blood, vasculature and other tissue proximate the brain are visualized, and/or devices positioned temporarily or permanently proximate the brain are visualized). The dimensions of imaging probe 100 for use in a neural procedure can be as follows. Imaging probe 100 can comprise an overall length L1 of approximately 300 cm. Outer shaft 101 can extend a length D5 of approximately 100 cm from connector assembly 150 to transition T$_1$. In some embodiments, D5 comprises a length greater than 10 cm and/or less than 150 cm. From transition T1 to T2, length D6 can comprise a length of approximately 175 cm. D6 can comprise a length of greater than 1250 mm and/or less than 2000 mm, such as a length of 1525 mm. Between transition T2 and T3, length D4 (the length of segment 127) can comprise a length of greater than 10 mm and/or less than 50 mm, such as a length of 25 mm.

Alternatively or additionally, imaging probe 100 can be constructed and arranged for use in an intravascular cardiac procedure (e.g. a procedure in which the blood, vasculature, and other tissue proximate the heart are visualized, and/or devices positioned temporarily or permanently proximate the heart are visualized). The dimensions of imaging probe 100 for use in a cardiovascular procedure can be as follows. Imaging probe 100 can comprise an overall length L1 of at least 220 cm, such as an overall length L1 of approximately 280 cm. In some embodiments, L1 comprises a length greater than 2600 mm and/or less than 3200 mm. Outer shaft 101 can extend a length D5 of approximately 100 cm from connector assembly 150 to transition T$_1$. From transition T1 to T2, length D6 can comprise a length of approximately 155 cm. Between transition T2 and T3, length D4 (the length of segment 127) can comprise a length of approximately 10 mm. In some embodiments, D4 comprises a length of greater than 10 mm and/or less than 50 mm.

Referring now to FIG. 2A, a magnified view of Section 1 of FIG. 2 is illustrated, consistent with the present inventive concepts. Section 1 details transition T1 of imaging probe 100. The following describes a set of components constructed and arranged to transition shaft 120 from a first diameter shaft, outer shaft 101, that surrounds torque shaft 105, to a smaller diameter shaft, intermediate shaft 125, that surrounds optical core 110 after torque shaft 105 terminates. Outer shaft 101 can comprise a greater stiffness than shaft 125, a different material, and/or other varied physical properties. The components described also operably attach the distal end of torque shaft 105 to optical core 110, as described herebelow. Alternatively, various other components can be implemented to achieve the transition T1. Optical core 110 can comprise a coating 111. Coating 111 can comprise a cladding, such as an optical cladding known to those skilled in the art of optical design, a protective coating such as a polyimide coating, and/or combinations of these.

Torque shaft 105, which surrounds optical core 110, terminates at T1, approximately 100 cm from the proximal end of imaging probe 100. Torque shaft 105 is configured to rotate within outer shaft 101, and is fixedly attached to optical core 110, such as to transfer rotational force between the two. In some embodiments, torque shaft 105 is constructed and arranged to rotate in a single direction (unidirectionally). Alternatively, torque shaft 105 can be constructed and arranged to rotate in either direction (bidirectionally). A rotating alignment element, tube 106, is positioned between the distal portion of torque shaft 105 and optical core 110, (e.g. slidingly receives optical core 110 and is slidingly received by torque shaft 105). Tube 106 extends beyond the distal end of torque shaft 105. A bond 107, for example a bond comprising an epoxy or UV glue, fixedly attaches tube 106 to optical core 110 and/or torque shaft 105. Alternatively or additionally, a press or other frictional bond fixedly attaches tube 106 to optical core 110 and/or torque shaft 105. An intermediate "transition" tube, tube 122, is positioned between outer shaft 101 and shaft 125, as shown. Tube 122 is slidingly received within a distal portion of outer shaft 101, and the proximal portion of shaft 125 is slidingly received within the distal portion of tube 122 (as well as outer shaft 101). In some embodiments, shafts 101, 125, and tube 122 are fixedly attached to each other, such as via a glue and/or frictional fit. In some embodiments, the distal end of outer shaft 101 extends beyond the distal end of tube 122. A second alignment element, tube 121, can be positioned within tube 122, abutting the proximal end of shaft 125. In some embodiments, tube 106 does not rotate relative to tube 122. The distal end of tube 106 is slidingly and rotatably received within the proximal portion of tube 122, and frictionally abuts tube 121. Tube 121 can comprise a material selected to minimize the friction between tube 121 and tube 122. Tubes 121, 106, and 122 form a rotary type joint, allowing torque shaft 105 to rotatably attach to shaft 125. Tubes 121 and 106 abut to prevent torque shaft 105 and/or optical core 110 from moving distally within shaft 125.

Several dimensions of and/or between various components of imaging probe 100 are illustrated in FIG. 2A. Tube 106 can comprise a length D7. Imaging probe 100 can comprise a gap with length D8, D8 representing the length between the distal end of torque shaft 105 and the proximal end of tube 122. Tube 122 can overlap tube 106 with an overlapping length D9. Tube 121 can comprise a length D10. Tube 122 can comprise a length D11.

In some embodiments, D7 comprises a length of greater than 5 mm and/or a length of less than 50 mm, such as a length of 20 mm. D8 can comprise a length of greater than 1 mm and/or less than 10 mm, such as a length of 5 mm. Overlap D9 can comprise a length of greater than 3 mm and/or less than 30 mm, such as a length of 5 mm. D10 can comprise a length of greater than 3 mm and/or less than 30 mm, such as a length of 5 mm. Overlap D11 can comprise a length of greater than 10 mm and/or less than 100 mm, such as a length of 25 mm.

Referring now to FIG. 2B, a magnified view of Section 2 of FIG. 2 is illustrated, consistent with the present inventive concepts. Section 2 details transitions T2 and T3 of imaging probe 100. The following describes a set of components constructed and arranged to transition shaft 120 from a first portion with a first flexibility, to a second portion with a second flexibility (at transition T2), and from a first shaft comprised of a first material (shaft 125), to a second shaft comprised of a second material (window 130, comprising an optically transparent material). Alternatively, various other components can be implemented to achieve the transitions T2 and T3.

At transition T2, segment 127 of shaft 125 begins, transitioning shaft 125 from a first flexibility, to a second, greater flexibility. Segment 127 can comprise a flexibility enhancing "feature", such as a modification applied to segment 127 of shaft 125 selected from the group consisting of: a spiral cut (as shown); a corrugation; one or more relief cuts; one or more openings; a thinning of the outer wall; and combinations of these. In some embodiments, the modification of segment 127 creates one or more passageways (e.g. holes) into and/or out of shaft 125, such as passageways through which bodily fluids and/or other contaminates can enter and/or exit shaft 125. Alternatively or additionally, the modification of segment 127 can weaken the column and/or other structural strength of shaft 125. A covering, tube 129, can be slidingly received over segment 127, configured to prevent contamination ingress and/or provide additional structural support to segment 127. Tube 129 can comprise a flexible material, such as a material more flexible than segment 127 of shaft 125.

Shaft 125 terminates at T3. A covering, for example tube 129 shown, or alternatively a separate covering, can surround the transition point T3. Tube 129 can provide a seal around segment 127, for example when segment 127 comprises a spiral cut that could otherwise allow ingress and/or egress to or from shaft 120. Alternatively or additionally, segment 127 of shaft 125 can comprise a flexible material (e.g. a material with a greater flexibility than the remainder of shaft 125), such as a polymer, and can comprise a braided construction, such as a braided construction including a metallic and/or non-metallic braid. Window 130 begins at transition T3. Optical core 110 is slidingly received by both shaft 125 and window 130, exiting the distal end of shaft 125 and entering the proximal end of window 130 at transition T3. Tube 129 maintains the relative position of the distal portion of shaft 125 with the proximal portion of window 130, including the relative axial positions of each (e.g. a coaxial arrangement), and the longitudinal positioning of the proximal end of window 130 relative to the distal end of shaft 125 (e.g. the ends abut each other, or nearly abut each other). Additionally or alternately, other methods of maintaining the relative position of window 130 and shaft 125 can be used, such as in a manufacturing process, for example a reflowing process, a welding process, and/or a splicing process that can be used to join, and position, window 130 and shaft 125.

As shown, the gel 118 can be positioned from the proximal end of tip 119 to a location proximate location T3, where T3 is a location distal to the proximal end of window 130. Gel 118 can be injected (e.g. in a manufacturing process) into shaft 120 (e.g. from the distal end of window 130) such that the proximal end of gel 118 (after injection is complete) is positioned at a location between 50 mm and 500 mm from the proximal end of tip 119, such as at a location between 200 mm and 250 mm from the proximal end of tip 119 (e.g. distance D1+D2 of FIG. 2).

Several dimensions of and/or between various components of imaging probe 100 are illustrated in FIG. 2B. Tube 129 can extend a length D12 proximally beyond the proximal end of segment 127. Imaging probe 100 can comprise a gap with length D14, with D14 representing the length between the distal end of shaft 125 and the proximal end of window 130. Tube 129 can extend a length D13 over window 130, as shown.

In some embodiments, D12 comprises a length of greater than 5 mm and/or less than 20 mm, such as a length of 10 mm. D14 can comprise a length of less than 1 mm, such as less than 0.2 mm, such as a length of approximately 0, such as when shaft 125 abuts window 130. D13 can comprise a length of greater than 5 mm and/or less than 20 mm, such as a length of 15 mm.

Figure 2C:
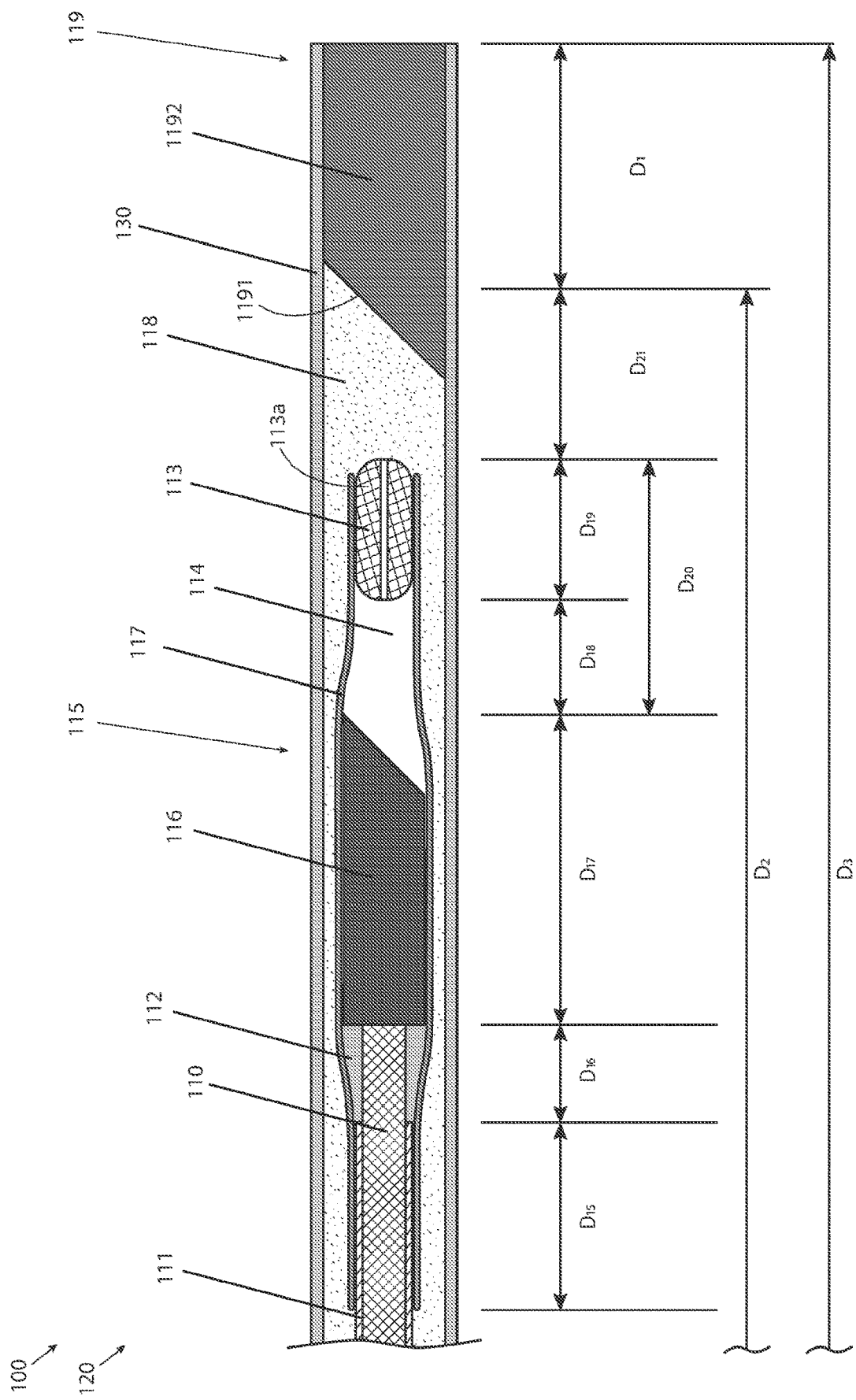
FIG. 2C illustrates a magnified view of the distal portion of imaging probe 100, consistent with the present inventive concepts.

Referring now to FIG. 2C, a magnified view of Section 3 of FIG. 2 is illustrated, consistent with the present inventive concepts. Section 3 details the distal portion of imaging probe 100. Optical assembly 115 is operably (e.g. optically) attached to the distal end of optical core 110. Optical assembly 115 is located within window 130, and it is configured to rotate about its longitudinal axis (e.g. rotate with optical core 110 within imaging probe 100). Gel 118 surrounds at least optical assembly 115 within window 130. Gel 118 can comprise a sheer thinning material, as described herein. Distal tip 119 can comprise sealing element 1192, configured to "plug" (e.g. prevent egress from) the distal end of window 130, such as to prevent gel 118 from exiting the distal end of window 130. Distal tip 119 can comprise a spring tip (not shown, but known to those skilled in the art of catheter design). Distal tip 119 can comprise a radiopaque, or other marker configured to increase the visibility of at least the distal tip 119 of imaging probe 100 using an imaging device, for example X-ray and/or fluoroscopy. In some embodiments, sealing element 1192 of distal tip 119 comprises an angled proximal end 1191, as shown, such as to prevent or at least reduce the reflection of light escaping from the distal end of lens 116 back towards lens 116 (e.g. to prevent or at least reduce coupling of light between lens 116 and the proximal end of distal tip 119).

Proximal end 1191 can comprise an angled proximal end between 15° and 80°, such as 45°.

Optical assembly 115 can comprise a focusing element, lens 116, such as a GRIN lens. Optical assembly 115 can further comprise a covering, sheath 117, and an enclosed volume, chamber 114, positioned distal to lens 116 (e.g. the distal end of lens 116 defines the proximal end of chamber 114). A sealing element, plug 113, defines the distal end of chamber 114. Lens 116 can be optically connected to optical core 110, such as via a weld, as is typical in the art of fiber optic design. Coating 111 (or another coating) of optical core 110 can be removed proximate the distal end of optical core 110, such that coating 111 does not interfere with the fiber optic joining process. Lens 116 can comprise an outer diameter of less than 300 microns, such as less than 250 microns, or less than 200 microns. Lens 116 can comprise a length of greater than or equal to 0.5 mm, such as a length greater than or equal to 1 mm. Lens 116 can comprise numerous configurations, such as when lens 116 comprises a beam deflector (e.g. a reflective surface configured to direct light into and out of lens 116) polished or otherwise formed onto the distal end of lens 116 (e.g. a GRIN lens with a polished facet). Additionally or alternatively, lens 116 can comprise a planar distal end, an aspherical distal end, a spherical distal end, and/or a cylindrical distal end. The distal end of lens 116 can comprise a directly reflecting beam deflector (e.g. a beam deflector reflectively coated with metallic and/or dielectric coatings) and/or a total internally reflective beam deflector (e.g. internal reflection within lens 116). In some embodiments, lens 116 comprises a doping profile configured to provide particular focus requirements and/or to allow polishing of a beam-deflecting surface directly into lens 116 (e.g. in manufacturing), without causing excessive beam distortion (e.g. while preserving the intended optical function of lens 116). In some embodiments, lens 116 comprises a numerical aperture of less than 0.2, such as less than 0.18. Additionally or alternatively, lens 116 can comprise a parabolic and/or quadratic doping profile constant of less than 2 $mm^{-1}$, such as less than 1.7 $mm^{-1}$. Sheath 117 can slidingly receive lens 116, and at least a distal portion of optical core 110 including coating 111, such that any portion of optical core 110 in which coating 111 has been removed is covered by sheath 117. In some embodiments, a protective material, filler 112, surrounds the uncladded portion of optical core 110 within sheath 117. Filler 112 can comprise a glue, such as an epoxy or a UV glue, configured to protect optical core 110 and/or increase the internal reflection within optical core 110 to help prevent light from escaping the fiber. In some embodiments, the distal end of lens 116 provides an internal reflective surface, configured to reflect light approximately 90° into and/or out of lens 116. Chamber 114 can be filled with atmospheric air, and/or a gas, such as an inert gas. Chamber 114 can provide a protective barrier, preventing gel 118 from contacting the distal end of lens 116, such that the index of refraction between lens 116 and the gas within chamber 114 facilitates the internal reflection of lens 116. Plug 113 can comprise a porous sealing element, such as when plug 113 comprises a filter material, such as a porous filter material, configured to prevent ingress of gel 118 into chamber 114 (e.g. during a manufacturing process in which gel 118 is injected into window 130) and/or to allow pressure to equalize within chamber 114 (e.g. during a manufacturing process, a sterilization process, or otherwise). In some embodiments, plug 113 comprises a plug with an opening (e.g. a non-porous plug with an opening), channel 113a, such as to allow pressure equalization.

Several dimensions of and/or between various components of imaging probe 100 are illustrated in FIG. 2C. Sheath 117 can overlap coating 111 with an overlap length D15. Optical core 110 can comprise a portion with length D16, with coating 111 removed. Lens 116 can comprise a length D17. Chamber 114 can comprise an opening with a length D18. Sheath 117 can extend beyond the distal end of lens 116 a length D20. Plug 113 can comprise a length D19. Imaging probe 100 can comprise a gap with length D21, D21 representing the length between the distal end of plug 113 and sealing element 1192. Sealing element 1192 can comprise a length D1.

In some embodiments, D15 comprises a length of greater than 0.5 mm and/or less than 10 mm, such as a length of 0.7 mm. D16 can comprise a length of greater than 0.5 mm and/or less than 10 mm, such as a length of 0.7 mm. D17 can comprise a length of greater than 0.5 mm and/or less than 5 mm, such as a length of 1.1 mm. D18 can comprise a length greater than 0.2 mm and/or less than 5 mm, such as a length of 0.4 mm. D19 can comprise a length greater than 0.2 mm and/or less than 5 mm, such as a length of 0.5 mm. D20 can comprise a length greater than 0.4 mm and/or less than 10 mm, such as a length of 0.9 mm. D21 can comprise a length greater than 0.5 mm and/or less than 10 mm, such as a length of 0.7 mm. D1 can comprise a length greater than 1 mm and/or less than 5 mm, such as a length of 2 mm.

Referring now to FIGS. 3, 3A-D, and 3E-G, an exploded view, four assembly views, a partial sectional view, a partially exploded view, and a perspective view of a connector assembly are illustrated, respectively, consistent with the present inventive concepts. Connector assembly 150 can be operably attached to the proximal end of an optical probe, such as imaging probe 100, as described herein. Connector assembly 150 can be constructed and arranged to operably attach (e.g. optically and mechanically attach) imaging probe 100 to a rotating fiber optic connector (e.g. a standard Fiber Optic Rotary Joint, FORJ). Connector assembly 150 comprises a fiber optic connector 161, configured to operably engage a mating connector and maintain a fiber optic connection. In some embodiments, fiber optic connector 161 comprises a commercially available fiber optic connector, such as a SC/APC fiber optic connector, such as those that are commonly used in telecommunication networks. In these embodiments, as described herein, connector assembly 150 can comprise one or more components constructed and arranged to operably engage, manipulate, and/or maintain the relative position and orientation of fiber optic connector 161 within connector assembly 150. Connector assembly 150 can include one or more alignment components, as described herebelow, to operably attach to a rotation assembly, such as rotation assembly 500 described herein, while maintaining the rotational orientation of fiber optic connector 161 relative to rotation assembly 500 during attachment and/or detachment. Connector assembly 150 can comprise numerous forms of connectors, such as a bayonet or other locking connector. The following describes a bayonet type connector constructed and arranged to provide the necessary forces and constraints to make and maintain a connection between imaging probe 100 and rotation assembly 500.

Figure 3:
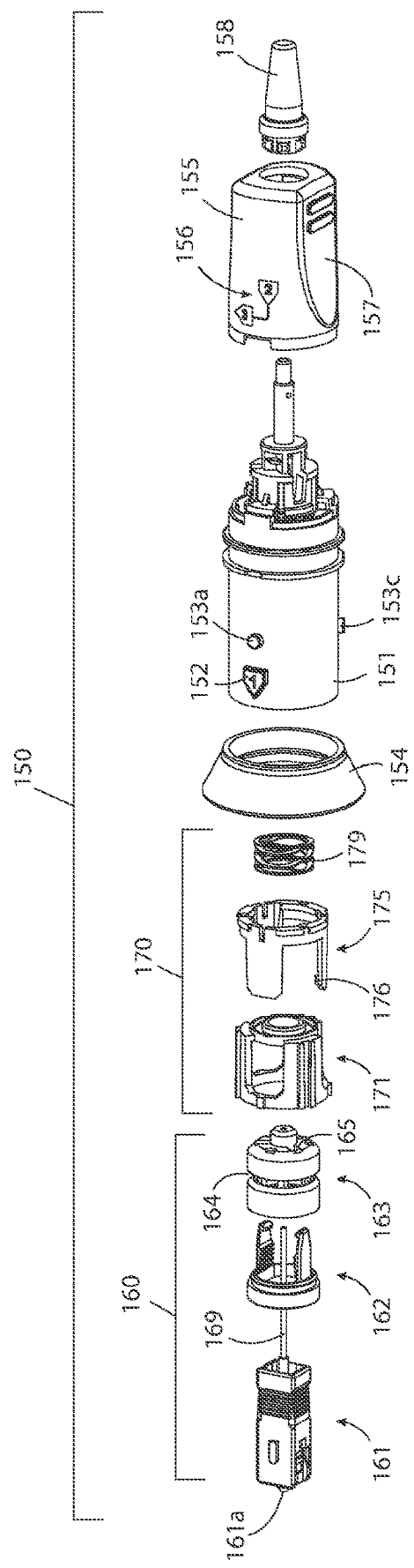
FIG. 3 illustrates an exploded view of a connector assembly, consistent with the present inventive concepts.
Figure 3B:
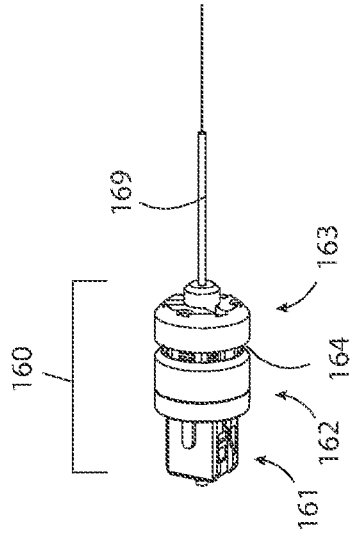
FIGS. 3A-D illustrate four assembly views of a connector assembly, consistent with the present inventive concepts.

Connector assembly 150 comprises a rotating assembly 160, a locking assembly 170, and a housing, connector body 151, surrounding at least a portion of rotating assembly 160 and locking assembly 170. Connector assembly 150 can include a protective covering, skirt 154. Skirt 154 can provide a seal between connector assembly 150 and connector assembly 510 of patient interface module 200, as described herein, such as to prevent ingress of contaminates into housing 201 of patient interface module 200. Rotating assembly 160 comprises optical connector 161. In some embodiments, optical connector 161 comprises a connector requiring proper rotational alignment with a mating optical connector, such as optical rotary joint 550 of rotation assembly 500 described herein. Connector assembly 150 can be constructed and arranged to provide the proper alignment between the two connectors when connecting and/or disconnecting without the need for an additional alignment step, such as to obviate the need for any user (e.g. manual) and/or systematic alignment step. Optical connector 161 further comprises a coupling shaft, shaft 169. Optical connector 161 (including coupling shaft 169) slidingly receives the proximal end of optical core 110 and torque shaft 105 (not shown). Torque shaft 105 and/or optical core 110 can operably attach to optical connector 161 (e.g. via coupling shaft 169), such that rotational force is applied to torque shaft 105 and/or optical core 110 by optical connector 161 (e.g. rotation of optical connector 161 causes the rotation of torque shaft 105 and/or optical core 110). In some embodiments, rotating assembly 160 is configured to rotate optical core 110 in a single direction (unidirectionally). Alternatively, rotating assembly 160 is configured to rotate optical core 110 in either direction (bidirectionally). The proximal end of optical core 110 is positioned within optical connector 161 such that the proximal end of optical core 110 is aligned with the proximal end of connector 161, forming a first optical transmission surface 161a, configured to abut a second optical transmission surface 555 (e.g. of a mating optical connector), to form an optical connection. In some embodiments, the first and second optical transmission surfaces 161a, 555, can each comprise a bevel, such as to increase the amount of light transmitted thru the connection. Optical connector 161 can comprise a non-circular shape (e.g. a rectangular shape as shown), with an asymmetric profile, such that optical connector 161 can only mate with a second connector in a particular, aligned orientation (e.g. such that the beveled optical transmission surfaces are properly aligned). Rotating assembly 160 includes a circular housing, carrier 163, and a locking connector, clip 162, configured to fixedly maintain optical connector 161 within carrier 163, such as is shown in FIGS. 3A and 3B, two assembly views of rotating assembly 160. Carrier 163 comprises a first radial recess, slot 164, and one or more alignment recesses, holes 165. Carrier 163 and/or clip 162 can comprise one or more reliefs (e.g. openings, slots and/or recesses) and/or projections sized and positioned to rotationally balance rotating assembly 160. These reliefs and/or projections can be configured to offset any rotational imbalances of optical connector 161 or other component of rotating assembly 160 (e.g. optical connector 161 can be an unbalanced connector). When fully assembled, rotating assembly 160 is rotationally balanced such as to limit vibration or other adverse effects of an imbalanced load at high rotational speeds.

Locking assembly 170 comprises a housing, rotational lock 171, a retention mechanism, connector retainer 175, comprising one or more retention elements, projections 176, and a biasing element, locking spring 179.

Figure 3D:
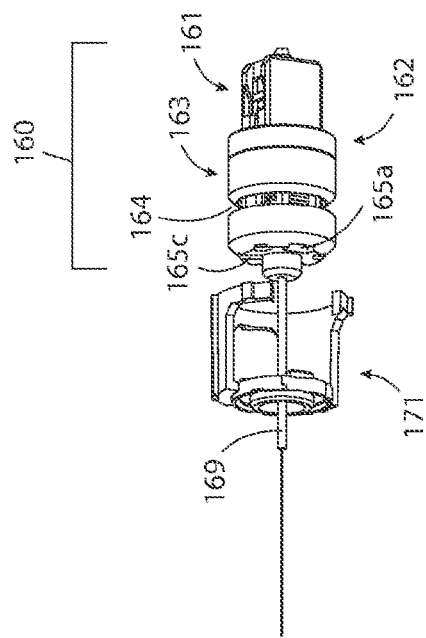
Figure 3A:
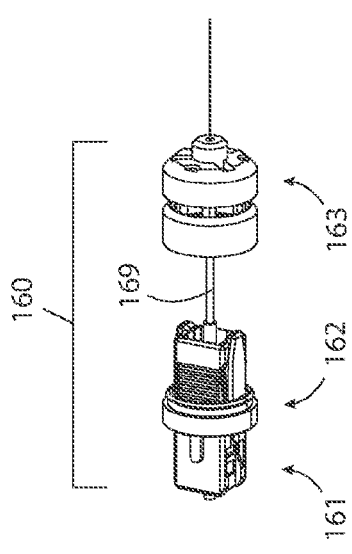
Figure 3C:
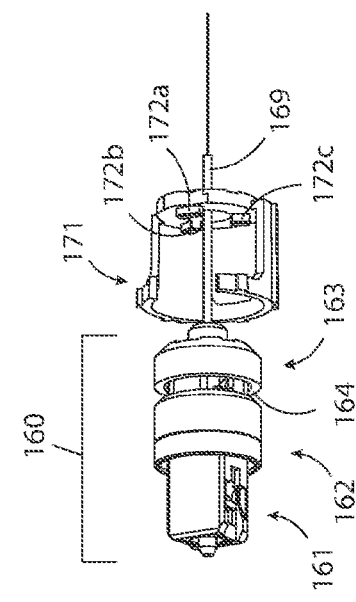

Referring to FIGS. 3C and 3D, opposing, partial sectional views of a portion of connector assembly 150 are illustrated. Rotational lock 171 comprises one or more projections, locking teeth 172 (three teeth 172a-c shown). Rotating assembly 160 is slidingly received within rotational lock 171, such that locking teeth 172a-c slidingly engage holes 165 of carrier 163 (165a and 165c shown, with 165b positioned opposite projection 172b), when rotating assembly 160 is fully inserted within rotational lock 171. This engagement locks the rotational orientation between rotational lock 171 and rotating assembly 160. In some embodiments, locking teeth 172 comprises an asymmetric pattern, and holes 165 comprise a matching asymmetric pattern, such that there is a single rotational orientation in which carrier 163 can be fully engaged within rotational lock 171 (e.g. hole 165a and projection 172a are sized to mate exclusively). Alternatively or additionally, rotational lock 171 can comprise a friction plate for frictionally engaging carrier 163. Connector retainer 175 is positioned about rotational lock 171 and carrier 163 (e.g. slidingly positioned about rotational lock 171 and carrier 163 in an assembly process), such that projections 176 are captured within slot 164, preventing rotating assembly 160 from exiting rotational lock 171. Slot 164 can comprise a width greater than the width of projection 176, such that rotating assembly 160 can travel longitudinally (e.g. axially) within rotational lock 171. For example, rotating assembly 160 can travel proximally such that locking teeth 172 disengage from holes 165 (e.g. rotational lock 171 can travel distally relative to rotating assembly 160 when a force is applied to rotational lock 171 as described herebelow). Projections 176 can operably engage the distal edge of slot 164, preventing rotating assembly 160 from exiting rotational lock 171. Additionally, carrier 163 can travel distally from the proximal most position, such that locking teeth 172 engage holes 165, and the distal end of carrier 163 abuts the back wall of rotational lock 171.

Figure 3G:
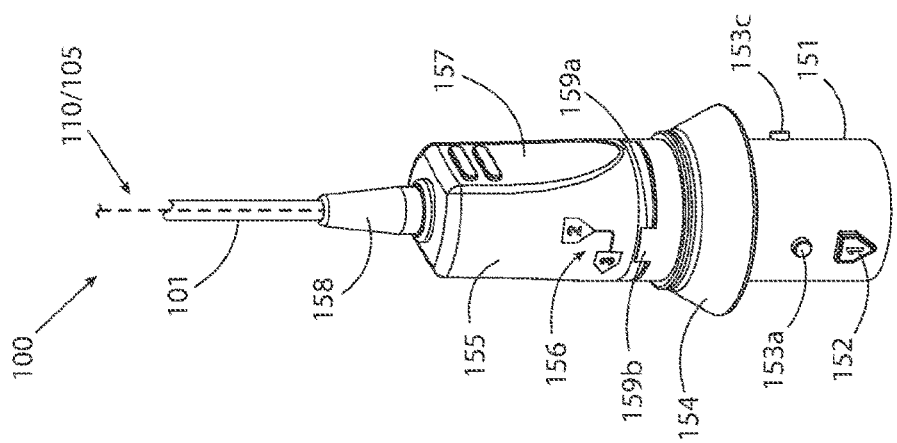
FIGS. 3E-G illustrate a partial sectional view, a partially exploded view, and a perspective view of a connector assembly, consistent with the present inventive concepts.
Figure 3F:
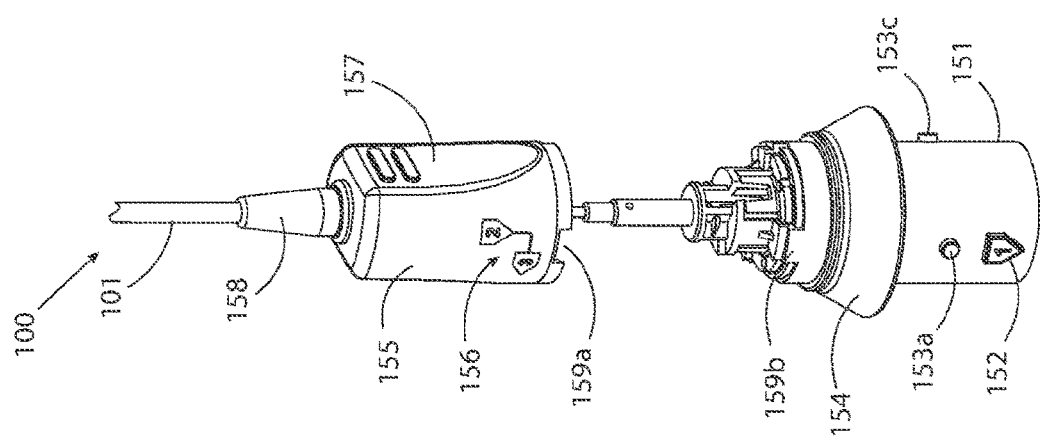
Figure 3E:
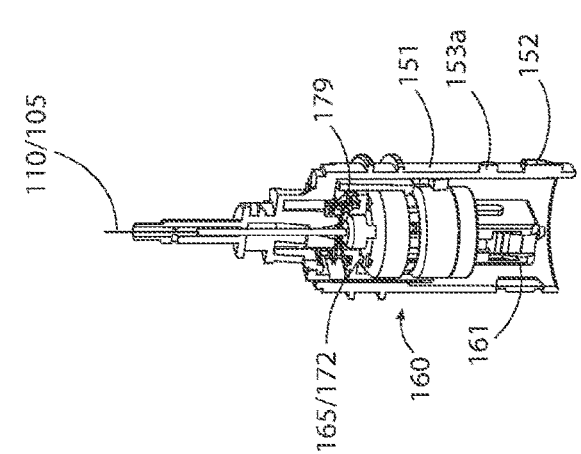

Referring to FIGS. 3E-G, rotating and locking assemblies 160, 170 shown are slidingly received within connector body 151. Locking assembly 170 is rotationally fixed within connector body 151. Rotating assembly 160 is rotationally fixed to locking assembly 170 when locking teeth 172 are engaged with holes 165, and therefore also fixed to connector body 151; otherwise rotating assembly 160 is free to rotate within connector body 151. In some embodiments, connector retainer 175 is fixedly positioned within connector body 151, and rotational lock 171, as well as rotating assembly 160 "float" within connector body 151, relative to connector retainer 175. Rotating assembly 160 is "captured" by connector retainer 175, such that it is allowed to rotate and travel longitudinally, as described hereabove, between a proximal-most location (where projections 176 engage slot 164) and a distal-most location (where the distal end of rotating assembly 160 abuts rotational lock 171). Connector assembly 150 can further comprise a biasing element, spring 179, configured to bias one or more components of connector assembly 150, such as when connector assembly 150 is not connected to a mating connector. For example, spring 179 can be positioned between a portion of connector body 151 and rotational lock 171, biasing rotational lock 171 distally against rotating assembly 160. Rotating assembly 160 is in turn biased against connector retainer 175 in its proximal-most position. This biased arrangement can prevent disengagement of locking teeth 172 from holes 165, maintaining the relative rotational orientation between rotating assembly 160 and connector body 151, while connector assembly 150 is not connected to a mating connector. Alternatively or additionally, when connector assembly 150 is connected to a mating connector, spring 179 can bias connector body 151 "out of" the mating connector, helping to facilitate one or more interlocking mechanisms, as described herebelow in reference to FIGS. 6A-D.

Connector body 151 includes one or more projections for alignment and engagement with a mating connector. As shown, connector body 151 comprises a first projection, alignment marker 152, configured to visually and operably align connector assembly 150 to a mating connector, as described herebelow in reference to FIGS. 4A through 6D. Alignment marker 152 can indicate the "top" of connector body 151, and be rotationally aligned with the "top" of optical connector 161, for example when optical connector 161 is rotationally locked relative to connector body 151 via rotational lock 171. Connector body 151 can further include one, two or more locking projections, projections 153a and 153c shown (projection 153b not shown but positioned behind connector body 151). Connector assembly 150 can further comprise a second body portion, cover 155. Cover 155 can comprise one or more mating elements, recess 159a shown, configured to properly align cover 155 to connector body 151 by aligning with one or more mating elements of connector body 151, projection 159b shown. Cover 155 can include instructional markings, markings 156, and one or more depressed, contoured, or otherwise ergonomic portions, grips 157. Grips 157 can be constructed and arranged such that a user can naturally grasp connector assembly 150, align connector assembly 150 with a mating connector (e.g. while using markers 152 and 156 for alignment and instruction), and insert and twist connector assembly 150 to secure the connection. Markings 156, along with marking 152 can indicate to the user the steps for engaging connector assembly 150 to a mating connector, for example, insert, push, and turn.

Connector assembly 150 can further include an element configured to reduce strain between connector 150 and one or more components of imaging probe 100, strain relief 158. As shown, imaging probe 100 comprises an outer proximal shaft, outer shaft 101, surrounding at least optical core 110 and torque shaft 105. Strain relief 158 slidingly receives outer shaft 101, which is fixedly attached to connector assembly 150. Optical core 110 and torque shaft 105 are free to rotate within outer shaft 101.

Referring now to FIGS. 4A-C, two perspective views of connectors being attached to a patient interface module and a perspective view of a portion of the patient interface module with the outer casing removed are illustrated, respectively, consistent with the present inventive concepts. Patient interface module 200 is configured to provide rotation to a rotatable optical core of an imaging probe, and to provide a motive force to translate at least a portion of the imaging probe, such as is described herebelow. Patient interface module 200 comprises rotation assembly 500, and at least a portion of retraction assembly 800. A housing 201 surrounds patient interface module 200. Patient interface module 200 can comprise one or more user interface elements, such as one or more inputs, buttons 205a,b, and one or more outputs, indicator 206 shown. Patient interface module 200 comprises a first physical connector assembly, connector assembly 510, for operably connecting to connector assembly 150, as described herein. Patient interface module 200 can further comprise a second physical connector assembly, connector assembly 820a, for operably connecting to connector 840, also as described herein. As shown in FIG. 4A, connector assembly 150 and connector 840 can each comprise bayonet type connectors, constructed and arranged to be at least partially inserted into connector assemblies 510 and 820a, respectively. Connector assembly 150 and connector 840 can be subsequently rotated (e.g. an approximately 45° rotation) to lock their connections with connector assemblies 510 and 820a, respectively, as described herein. Connector assembly 150 and/or 840 can comprise numerous forms of connectors, such as a bayonet or other locking connectors. The following describes bayonet type connectors constructed and arranged to provide the necessary forces and constraints to make and maintain a connection between imaging probe 100 and rotation assembly 500.

As shown in FIG. 4C, connector assembly 510 comprises a floating locking portion, sleeve 515. Sleeve 515 comprises one or more "cut away" portions or reliefs, openings 517a-c (517b,c not shown, but positioned about sleeve 515, such as positioned equally about sleeve 515). The distal edge of openings 517a-c comprise an engineered shape, locking profiles 518a-c (profile 518a shown). Locking profiles 518a-c can be constructed and arranged to operably engage projections 153a-c of connector body 151, as described herebelow (projection 153a shown in FIG. 4C). Sleeve 515 can comprise one or more passageways, recesses 516a-c (recess 516a shown in FIG. 4C). Recesses 516a-c ensure proper alignment of connector assembly 150 when inserted into connector assembly 510. Projections 153a-c pass thru recesses 516a-c, and into openings 517a-c, respectively. As projections 153a-c enter openings 517a-c, connector assembly 150 is free to rotate relative to connector assembly 510.

After connector body 151 is inserted into connector assembly 510, connector assembly 150 is rotated, as shown in FIG. 4B, and projections 153a-c slidingly engage locking profiles 518a-c. Locking profiles 518a-c are constructed and arranged such that projections 153a-c (as well as connector assembly 150) are initially forced inward, towards connector assembly 510 when rotated. Connector assembly 510 can comprise one or more biasing elements, retention elements 519. Retention elements 519 can comprise one or more retention elements, such as three elements spaced equally around the perimeter of sleeve 515. Retention elements 519 can comprise spring assemblies, constructed and arranged to bias sleeve 515 "inward", towards the proximal end of connector assembly 510. Retention elements 519 allow sleeve 515 to travel outward, as forced by projections 153a-c against locking profiles 158a-c. Retention elements 519 can be constructed and arranged such that sleeve 515 applies a predetermined force to connector assembly 150 when rotated to engage locking profiles 518a-c.

Patient interface module 200 comprises a structural support, frame 202, onto which the elements of rotation assembly 500 and retraction assembly 800 can be mounted (e.g. directly and/or indirectly mounted, to secure the relative position of the elements within patient interface module 200). Connector 840, described herebelow in detail in reference to FIGS. 7A-C, can similarly be attached to connector assembly 820a. An embodiment of connector assembly 820a is described in detail herebelow in reference to FIG. 9.

Figure 5:
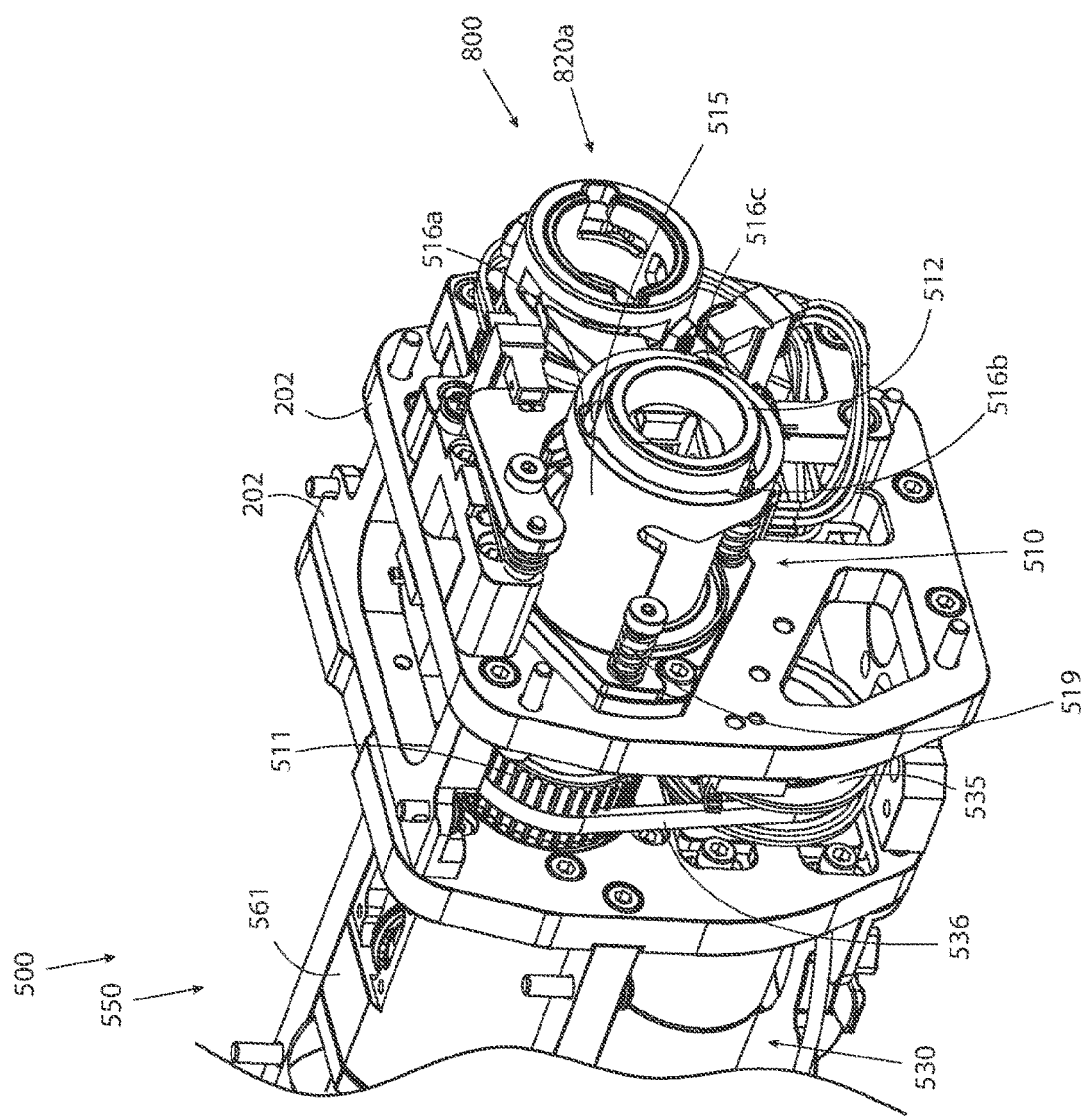
FIG. 5 illustrates a perspective, partial cut away view of components of a patient interface module, consistent with the present inventive concepts.
Figure 5A:
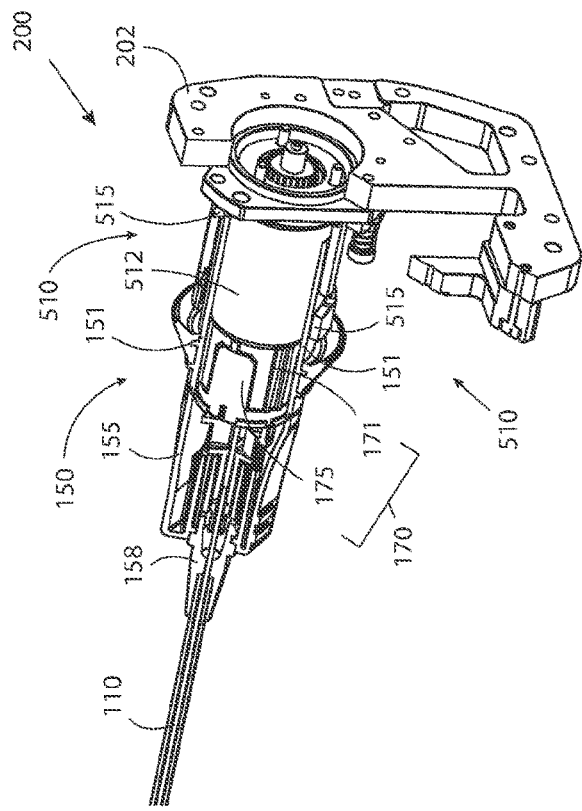
Figure 5B:
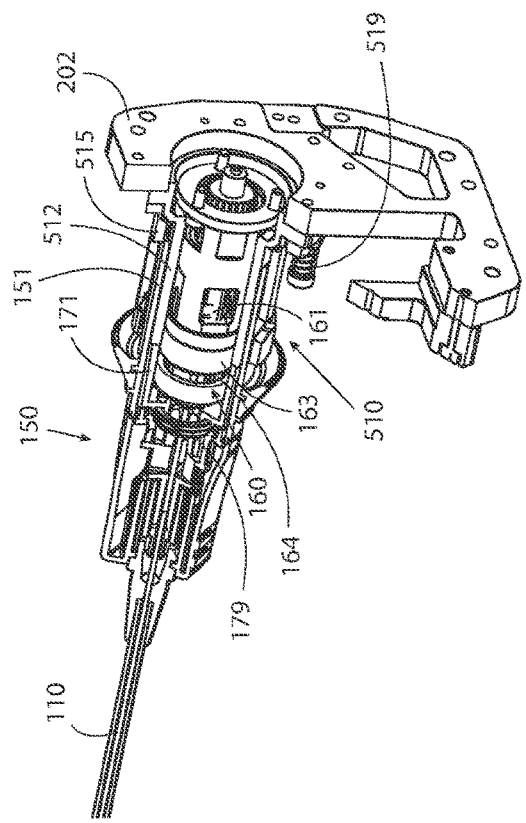

Referring now to FIGS. 5, and 5A-D, perspective, partial cut away views of components of a patient interface module are illustrated, consistent with the present inventive concepts. FIG. 5 illustrates the connector assemblies 510 and 820a, and components of rotation assembly 500 within patient interface module 200, with housing 201 removed. FIGS. 5A and 5B illustrate connector assembly 150 operably connected to connector assembly 510. In FIG. 5A, one or more components are sectioned, revealing sleeve 512, rotational lock 171, and connector retainer 175. In FIG. 5B, sleeve 512, rotational lock 171, and connector retainer 175 are also sectioned, revealing rotating assembly 160 and mating components within sleeve 512. FIGS. 5C and 5D illustrate an assembly comprising a fiber optic rotary joint 560. In FIG. 5C, multiple components are shown sectioned, and multiple components are shown transparently. In FIG. 5D, multiple components are shown sectioned.

Rotation assembly 500 comprises an optical connector, rotary joint 550, and a fiber optic rotary joint, rotary joint 560. As shown in FIGS. 5C and 5D, rotary joint 560 comprises a fixed portion, housing 561. A rotating portion, spindle 562, rotates relative to housing 561. At least a portion of spindle 562 is positioned within housing 561. Rotary joint 560 can comprise one or more rotary bearings, bearings 563a-b shown, configured to limit friction and provide a smooth interface for rotation between spindle 562 and housing 561.

Sleeve 515 surrounds a fixed connection element, sleeve 512. Connector body 151 is slidingly received between sleeves 515 and 512 (i.e. during and while connector assembly 150 is connected to connector assembly 510). As connector assembly 150 is inserted into connector assembly 510, sleeve 512 opposes rotational lock 171, preventing rotational lock 171 from traveling proximally (further "into" connector assembly 510) beyond a predetermined distance. As connector body 151 is pushed further into connector assembly 510, locking spring 179 is depressed by rotational lock 171. Connector body 151 can be configured to abut carrier 163 when spring 179 is sufficiently depressed, such as to apply a force to carrier 163 as connector body 151 is pushed further into connector assembly 510 (e.g. push further via rotation of connector body 151 within sleeve 515, as locking profiles 518a-c force connector body 151 forward). This force between connector body 151 and carrier 163 can be sufficient to ensure optical connector 161 fully engages receptacle 551.

Referring back to FIG. 5, Rotation assembly 500 comprises motive element 530 which can be configured to provide a motive force that causes translation (e.g. retraction) of at least a portion of an imaging probe of the present inventive concepts. Motive element 530 can comprise a motor, configured to provide a rotary force to spindle 562. Motive element 530 can comprise a force transfer element, pulley 535, operably attached to a force transfer element of spindle 562, gear 511. Pulley 535 and gear 511 can be operably connected via a drive mechanism, linkage 536. In some embodiments, linkage 536 comprises a chain or other drive mechanism. In some embodiments, pulley 535 and gear 511 comprise a force and/or speed multiplying relationship, such as a 1:2 ratio.

Referring to FIGS. 5C and 5D, rotary joint 550 can comprise a receptacle 551, configured to slidingly receive optical connector 161 of rotating assembly 160. Receptacle 551 can comprise a recess 552, configured to slidingly receive a projection from optical connector 161 when connector 161 is properly aligned with receptacle 551. Rotary joint 550 can comprise a "floating" portion 553, configured to compensate for motion (e.g. linear motion) during and/or after the connection of optical connector 161 to rotary joint 550. Compensation is achieved by floating portion 553 moving axially within rotary joint 550. Floating portion 553 can be biased towards the distal end of receptacle 551 (e.g. biased toward optical connector 161), such as when floating portion 553 includes a biasing spring. In some embodiments, after the connection of rotary joint 550 and connector 161, the resulting axial forces are balanced, such that there is minimal axial movement of floating portion 553 after the connection is made. In some embodiments, the balanced axial forces are adjusted (e.g. by adjusting the spring force of one or more force balancing springs) such that the force between optical transmission surfaces 555 and 161a is both sufficient for optical transmission, and below a level that may damage either optical transmission surface 555 and/or 161a. Floating portion 553 surrounds and is operably attached to an intermediate fiber optic conduit, fiber optic cable 556. Fiber optic cable 556 terminates distally at an optical transmission surface 555. Optical transmission surface 555 is configured to abut optical transmission surface 161a when connected to optical connector 161, as described hereabove. The medial portion of fiber optic cable 556 is positioned within a recess or other space within spindle 562, channel 554. Fiber optic cable 556 terminates proximally at a fiber optic rotary coupling, rotary coupler 565. To compensate for linear displacement of floating portion 553, channel 554 can be constructed and arranged to allow fiber optic cable 556 to "buckle" within channel 554 (e.g. transition into in the "S" shape shown), and it can be sized and arranged to accommodate the maximum linear displacement of floating portion 553. Channel 554 can be further constructed and arranged such that the buckling of fiber optic cable 556 is rotationally balanced (e.g. limited to a single plane, such that the axis of symmetry of the "S" is coincident with the axis of rotation of spindle 562), such as to not induce a wobble and/or other vibration in spindle 562 when rotated at high speed. In some embodiments, channel 554 comprises an "S" shape. The "S" shape can comprise a radius configured to minimize light loss through fiber optic cable 556.

Rotary coupler 565 operably attaches to fiber optic cable 556 and to an output fiber optic cable, output fiber 569. Rotary coupler 565 optically and rotatably couples fiber optic cable 556, which rotates with spindle 562, to output fiber 569, which is fixedly attached (e.g. does not rotate) to housing 561.

Sleeve 515 surrounds a fixed connection element, sleeve 512. Connector body 151 is slidingly received between sleeves 515 and 512 (i.e. during and while connector assembly 150 is connected to connector assembly 510). As connector assembly 150 is inserted into connector assembly 510, sleeve 512 opposes rotational lock 171, preventing rotational lock 171 from traveling proximally (further "into" connector assembly 510) beyond a predetermined distance. As connector body 151 is pushed further into connector assembly 510, locking spring 179 is depressed by rotational lock 171. Connector body 151 can be configured to abut carrier 163 when spring 179 is sufficiently depressed, such as to apply a force to carrier 163 as connector body 151 is pushed further into connector assembly 510 (e.g. push further via rotation of connector body 151 within sleeve 515, as locking profiles 518a-c force connector body 151 forward). This force between connector body 151 and carrier 163 can be sufficient to ensure optical connector 161 fully engages receptacle 551.

Referring now to FIGS. 6A-D, schematic views of a locking mechanism are illustrated, consistent with the present inventive concepts. A projection 153 and alignment marker 152 of connector body 151 are shown, with all other components of connector assembly 150 removed for illustrative clarity. A line connecting projection 153 and marker 152 is shown, 151', representing the relative position of a portion of connector body 151 between FIGS. 6A-D. An opening 517 and a locking profile 518 of sleeve 515 are also shown, with other components of connector assembly 510 removed for illustrative clarity. The following describes the interaction of projection 153 and alignment marker 152 (also a projection from connector body 151) with locking profile 518, as connector body 151 is slidingly received and rotated within sleeve 515, such as to lock connector assembly 150 with connector assembly 510.

Figure 6A:
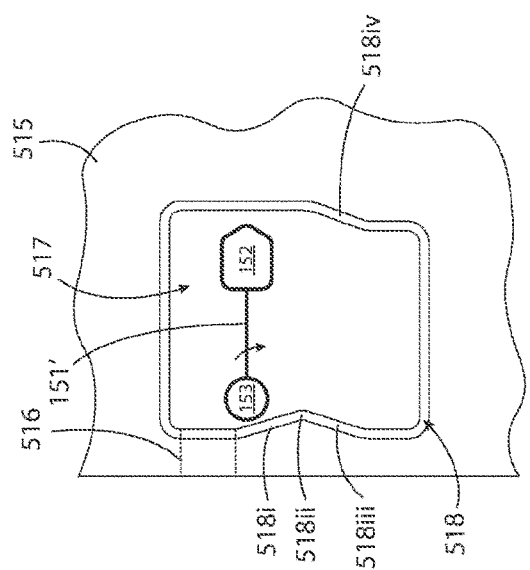
FIGS. 6A-D illustrate schematic views of a locking mechanism, consistent with the present inventive concepts.
Figure 6B:
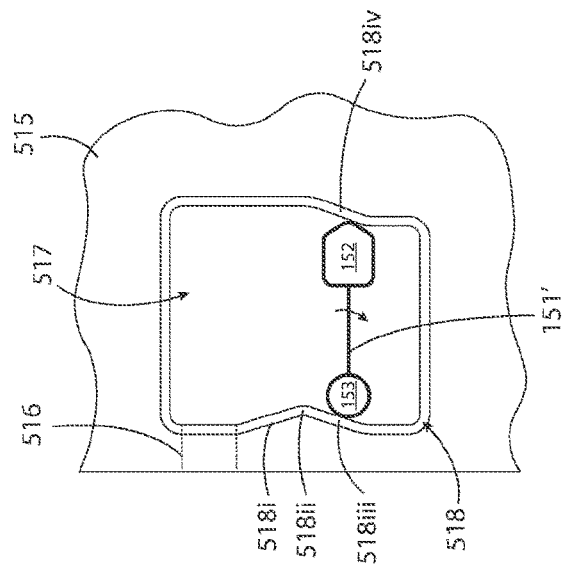
Figure 6C:
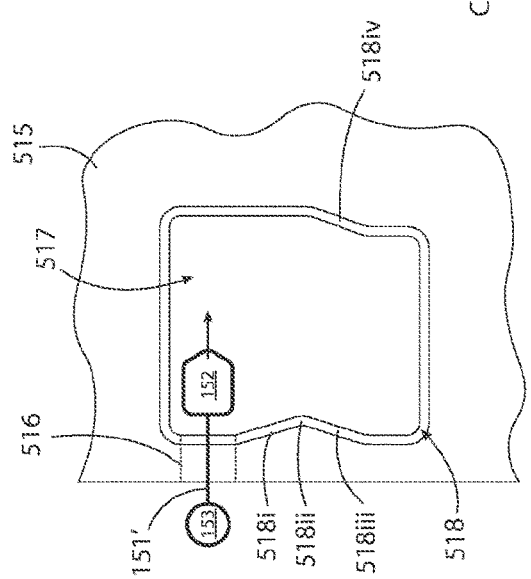

As connector body 151 is inserted (in a proximal direction) into sleeve 515, alignment marker 152 is slidingly received by recess 516, followed by projection 153. As projection 153 exits recess 516 and enters opening 517, connector body 151 is free to rotate (e.g. clockwise as indicated). Also, as projection 153 exits recess 516, optical connector 161 has been at least partially slidingly received by receptacle 551, such that the proper alignment between the two is maintained. Sleeve 512 opposes rotational lock 171, such as to release locking teeth 172a-c from holes 165a-c as rotating assembly 160 is forced forward, such that connector body 151 is free to rotate about rotating assembly 160 (as described hereabove). As connector body 151 is rotated clockwise, a first portion of locking profile 518, ramp 518i, forces projection 153 proximally, as shown in FIG. 6B. This in turn forces connector body 151, and rotating assembly 160 forward. Locking assembly 170 is maintained in its axial position by sleeve 512. Rotating assembly 160 does not rotate, as it is operably engaged to receptacle 551, and freed from locking assembly 170. In FIG. 6C, projection 153 is shown in its most proximal position (e.g. as forced by point 518ii of locking profile 518). Connector assemblies 150 and 510 can be constructed and arranged such that in the position indicated in FIG. 6C, connector body 151 forces optical connector 161 proximally such that it fully engages receptacle 551. In some embodiments, sleeve 515 is biased proximally (such as with one or more retention elements 519, as described herein), such that connector assembly 510 is constructed and arranged to provide a maximum force to projection 153 when forced proximally by point 518ii. In some embodiments, retention elements 519 allow accommodation of tolerances in and/or between connector assembly 150 and connector assembly 510 when the two are mated.

Figure 6D:
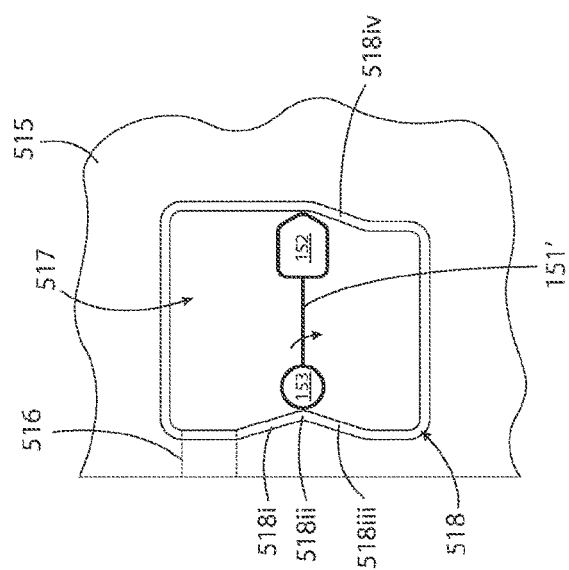

As connector body 151 is rotated further (i.e. further clockwise as indicated), ramp 518iv of locking profile 518 forces marker 152 distally, as ramp 518iii allows projection 153 to also retract distally, as shown in FIG. 6D. As projection 153 passes point 518ii, the bias of spring 179 between connector body 151 and locking assembly 170 also drives projection 153 along ramp 518iii. Connector assemblies 150 and 510 can be constructed and arranged such that in the final locked position of connector body 151 within sleeve 515, one or more of the following conditions are met: optical connector 161 is fully engaged within receptacle 551; connector body 151 is displaced laterally (e.g. distally) from the distal end of rotating assembly 160 such that there is no and/or limited frictional force between connector body 151 and rotating assembly 160; projections 176 of connector retainer 175 are positioned within slot 164 of rotating assembly 160, such that there is no and/or limited frictional force between rotating assembly 160 and locking assembly 170. During operation, such as during a clinical procedure, motive element 530 is constructed and arranged to rotate spindle 562, and in turn rotate rotating assembly 160 which is operably attached to receptacle 551. In order to maintain rotational alignment with components of connector assembly 150, motive element 530 can be constructed and arranged to only stop spindle 562 in the position aligned with the connection orientation (e.g. spindle 562 only stops at "top dead center" when motive element 130 is stopped). Motive element 530 can comprise a servo type motor to achieve this, and/or one or more sensors or biasing elements can be used to ensure this rotational orientation upon stopping. In some embodiments, motive element 530 and/or spindle 562 comprise a bias, such that top dead center is always achieved, even in the event of a power loss to rotation assembly 500.

When connector assembly 150 is disconnected from connector assembly 510, connector body 151 is rotated clockwise as indicated. Projection 153 is forced forward by ramp 518iii, beyond point 518ii, and can be retracted (e.g. by the user) along ramp 518i towards recess 516. As connector body 151 is retracted from sleeve 515, projection 153 and marker 152 align with recess 516, ensuring the alignment of rotating assembly 160 with locking assembly 170. Projections 176 can operably engage the distal edge of slot 164, pulling rotating assembly 160 from receptacle 551, as rotational lock 171 is biased against carrier 163. Connector assemblies 150 and 510 can be constructed and arranged such that locking teeth 172 operably engage holes 165, prior to optical connector 161 disengaging from receptacle 551, such that the orientation of rotating assembly 160 is continuously maintained.

Figure 7C:
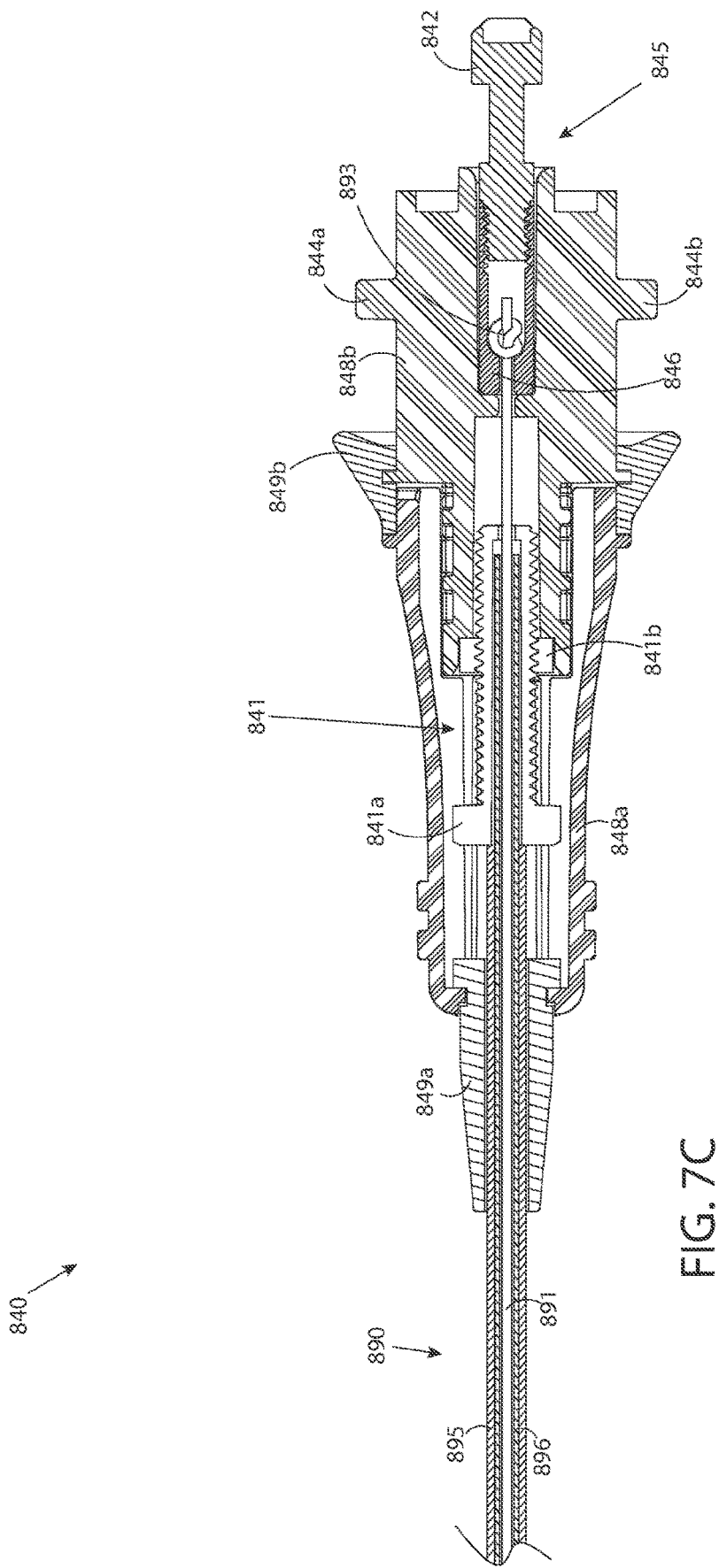

Referring now to FIGS. 7A-C, an exploded view, a perspective view, and a sectional view of a connector assembly are illustrated, respectively, consistent with the present inventive concepts. Connector assembly 840 can be operably attached to the proximal end of a mechanical linkage, linkage assembly 890. Linkage assembly 890 operably attaches to pullback module 880, as described herebelow in reference to FIGS. 8A-B. Connector assembly 840 can operably attach linkage 891 of linkage assembly 890 to motive element 830. Motive element 830 can comprise a linear actuator or other component that provides a force to linkage 891 such that linkage 891 advances and/or retracts relative to sheaths 895, 896, as described hereabove in reference to FIG. 1A. In some embodiments, patient interface module 200 is configured to only retract linkage 891, for example when linkage 891 can be manually or otherwise advanced, as described herein.

Linkage assembly 890 comprises outer sheath 895, inner sheath 896, and linkage 891. In some embodiments, sheath 895 provides a protective barrier for inner sheath 896. Inner sheath 896 can comprise a conduit configured to provide column strength to linkage assembly 890, such as a conduit comprising a torque wire. Sheaths 895, 896 slidingly receive linkage 891. Linkage 891 can comprise a wire, cable, or other filament. Linkage 891 comprises a proximal end 893. Proximal end 893 can extend beyond the proximal end of sheath 896, through connector 840, and into capture port 846 as described herebelow. Proximal end 893 can comprise a termination point such as a knot, crimp, and/or other feature to allow for the engagement of linkage 891 to capture port 846.

Connector 840 can comprise housing 848, such as a two-part housing with distal and proximal portions, housing 848a and housing 848b respectively. Housing 848a,b can comprise keyed geometries such that the two portions do not rotate relative to each other when assembled, as shown in FIG. 7B. Connector 840 can include a protective covering, skirt 849b. Skirt 849b can provide a seal between housings 848a,b, as well as around connector assembly 820a of patient interface module 200, as described herein, such as to prevent ingress of contaminates into housing 848. Connector 840 can further include a tension relieving element, strain relief 849a. In some embodiments, strain relief 849a surrounds a portion of linkage assembly 890 near the distal end of connector assembly 840, providing strain relief near the entry point of linkage assembly 890 into housing 848a. Connector 840 can comprise one, two or more locking projections, projection 844a and projection 844b shown. In some embodiments, projection 844a and projection 844b are positioned and spaced equally about housing 848b (e.g. two projections 844a,b, as shown, are positioned 180 degrees relative to each other). Connector 840 can further comprise locking elements, pins 843*a* and 843*b* shown. Pins 843*a,b* can be slidingly received through and engaged with a receiving portion (e.g. a hole, cutout, recess, or the like) of both housing 848*a* and housing 848*b*, locking the housings together. Alternatively or additionally, housing 848*a* and housing 848*b* can be glued or otherwise permanently or semi-permanently attached to each other.

Connector 840 can comprise connector assembly 845. Connector assembly 845 is slidingly received within the proximal end of connector 840, and it receives and fixedly attaches to proximal end 893 of linkage 891. Connector assembly 845 can comprise capture port 846 and connection point 842. Proximal end 893 of linkage 891 can comprise a geometry such that proximal end 893 is captured within capture port 846 (e.g. proximal end 893 is passed thru an opening in the distal end of capture port 846, and a knot is tied, preventing egress of the distal end from the port). A bulbous connecting point, connecting point 842, is operably attached to the proximal end of capture port 846. Connecting point 842 can be configured to operably engage motive element 830, of retraction assembly 800, as described herein.

Connector 840 can comprise a tensioning element, tensioning assembly 841. Tensioning assembly 841 can comprise a tensioning screw 841*a* and a tensioning nut 841*b*. Tensioning screw 841*a* can operably attach to the proximal end of sheath 895 and/or to the proximal end of sheath liner 896. As shown in FIG. 7C, sheath 895 terminates near the distal end of tensioning screw 841*a*, and sheath liner 896 is received within tensioning screw 841*a*, and is fixedly attached thereto. Sheath liner 896 can be glued or otherwise fixedly attached to tensioning screw 841*a*. Linkage 891 extends to connector assembly 845 through an opening at the proximal end of screw 841*a*. Housing 848*a* comprises a cavity configured to receive and secure tensioning screw 841*a*, preventing the rotation of screw 841*a* within housing 848*a*. Housing 848*b* can comprise a cavity configured to receive and secure tensioning nut 841*b*, preventing the rotation of nut 841*b* within housing 848*b*, and positioning nut 841*b* a set distance from the proximal end of connector 840. Tensioning assembly 841 can adjust the relative position of proximal end 893 of linkage 891 to the proximal end of sheath 895, such as an adjustment performed in an assembly process as described immediately herebelow.

Linkage assembly 890 can be singly received by strain relief 849*a* and housing 848*a*. Housing 848*a* can be temporarily positioned about linkage assembly 890 away from the proximal end of linkage assembly 890, to allow for tensioning adjustments or other assembly steps (e.g. during the manufacturing process). Linkage 891 can subsequently be slidingly received by tensioning assembly 841, skirt 849*b*, housing 848*b*, and capture port 846, with the proximal end 893 of linkage 891 extending beyond the proximal end of capture port 846. Proximal end 893 can then be knotted, or otherwise modified for securement, such that capture port 846 can be slid proximally, capturing proximal end 893, as shown in FIG. 7C. Connection point 842 can then be secured to the proximal end of capture port 846, and housing 848*b* can be slid proximally along linkage 891, such that connection assembly 845 is partially received within the proximal end of housing 848*b*, as shown. Tensioning nut 841*b* can be positioned within the distal end of housing 848*b*. Housing 848*b* comprises a geometry such that a minimum distance between connection assembly 845 and tensioning nut 841*b* is maintained. Sheath 895 and/or sheath 896 are fixedly attached to tensioning screw 841*a*, as described hereabove, and tensioning screw 841*a* is operably attached to tensioning nut 841*b*, (i.e. tensioning screw 841*a* is at least partially screwed into tensioning nut 841*b*). Tensioning assembly 841 can be adjusted, such as to adjust the minimum relative distance between proximal end 893 of linkage 891, and the proximal end of sheath 895 and/or sheath 896. This distance can be adjusted to modify the relative positions of one or more connected components of pullback housing 881, as described herebelow in reference to FIG. 8A. After the optimal relative position of components is achieved, housing 848*a* can be slid proximally, along linkage assembly 890, such that tensioning screw 841*a* is captured within housing 848*a*, preventing rotation of tensioning screw 841*a* relative to nut 841*b*, locking the relative component positions. Housing 848*a* is then fixedly or removably attached to housing 848*b*. After assembly, translation of connection assembly 845 proximally away from housing 848*b* pulls linkage 891, slidingly through sheath 895, such that the distal end of linkage 891 translates relative to the distal end of sheath 895, as described herebelow in reference to FIG. 8A. As linkage 891 is pulled distally, again as described herebelow, connector 840 prevents translation beyond the established minimum relative distance between proximal end 893 and the proximal end of sheath 895.

Referring now to FIGS. 8A-C, an exploded view, a perspective view, and an end view of a pullback assembly are illustrated, respectively, consistent with the present inventive concepts. Pullback module 880 can be operably attached to a portion of an imaging probe of the present inventive concepts, and provide a retraction force to the probe, pulling at least a portion of the probe proximally relative to a patient (e.g. relative to a patient introduction device), as described herebelow. Pullback module 880 can be operably attached to the distal end of a linkage 891. The proximal portion of linkage 891 operably attaches to connector assembly 840, as described hereabove in reference to FIGS. 7A-C.

Pullback module 880 can comprise a two-part housing 881, including a top housing 881*a* and bottom housing 881*b*, as shown in FIG. 8A. Module 880 can comprise one or more guide elements, rails 883*a,b*. Module 880 can contain a translating cart, puller 850. Puller 850 can be designed to translate within module 880 along rails 883*a,b*. Puller 850 slidingly receives rails 883*a,b* via recesses 851*a,b*. Recesses 851*a,b* are designed to partially or completely encompass rails 883*a,b*, such as to limit movement of puller 850 to translation along the axis of the rails 833*a,b*. Alternatively or additionally, housing 881 can comprise a geometry such that the motion of puller 850 is limited to axial translation within housing 881. Module 880 can comprise a biasing element, spring 852. Spring 852 can provide a biasing force to puller 850, such as to bias puller 850 distally.

Linkage assembly 890 can be slidingly received through strain relief 887. Strain relief 887 can be fixedly attached to the proximal end of module 880. Sheath 895 and/or sheath 896 can be fixedly attached to the proximal end of module 880. In some embodiments, strain relief 887 comprises a "hub" positioned between a flexible strain relieving portion and a portion of sheath 895 and/or sheath 896 and attached thereto. Strain relief 887 can aid in the attachment of sheath 895 and/or sheath 896 to module 880. Linkage 891 is slidingly received along the length of module 880 and is operably attached at its distal end to puller 850. Linkage 891 can comprise distal end 892 and can comprise a geometry that aids in the attachment of linkage 891 to puller 850. For example, distal end 892 can comprise a termination element, such as a knot or other feature arranged to allow for the secure engagement of linkage 891 to puller 850.

Top housing 880a can comprise a first cavity, retention port 884 and a second cavity, trench 889. Retention port 884 and trench 889 can be separated by a projection, retention wall 888. Physical connector assembly 820b can comprise a retention port of housing 881a, including wall 888, and a retention mechanism, clip 885. Clip 885 can be configured to releasably engage the proximal end of a delivery catheter such as sheath connector 82 of delivery catheter 80, such as when connector 82 comprises a Tuohy Borst connector. Physical connector assembly 820b can further comprise a biasing element, spring 886. Spring 886 can provide a biasing force to maintain clip 885 in an engaged position about connector 82, as shown in FIG. 8B.

Clip 885 can comprise a first projection, projection 885a, configured to partially surround connector 82 when connector 82 is inserted into retention port 884, as shown in FIG. 8C. Clip 885 can rotate about an axis, axis $A_1$, to allow sheath connector 82 to enter retention port 884 and rotate projection 885a "back" to engage connector 82. Second projection 885b extends through module 880 (e.g. through an opening in the wall of housing 881a). Clip 885 rotates about axis $A_1$ to release connector 82 when second projection 885b is engaged (e.g. engaged by a user).

Pullback module 880 can further comprise a carrier 855. Carrier 855 can operably attach to puller 850, such as through a slot 889a in housing 881a. Carrier 855 can translate within trench 889 in response to puller 850, which translates in response to linkage 891. Carrier 855 can operably attach to a portion of imaging probe 100, such as to a pullback connector 180. Pullback connector 180 can comprise a "torquer", or other device affixed to shaft 120 of imaging probe 100. Sheath 895 and/or sheath liner 896 of linkage assembly 890 provide a frame of reference between connector 840 and pullback module 880, such that when the proximal end of linkage 891 is retracted relative to connector 840 (as described hereabove in reference to FIGS. 7A-C), the distal end of linkage 891 is retracted towards sheath 895 (i.e. towards the proximal end of pullback module 880). This relative motion transfers motive force applied at connector 840 (e.g. via motive element 830, as described herein), to puller 850. Puller 850, subsequently transfers the motive force to imaging probe 100, and imaging probe 100 is retracted relative to the patient.

In operation, imaging probe 100 can be manually (e.g. by a user) advanced through the vasculature of the patient. Pullback module 880 can be attached to the patient (e.g. to delivery catheter 80 via connector 82), and connector 180 can be operably connected to imaging probe 100, and positioned proximate delivery catheter 80 (e.g. a torquer connector 180 can be tightened to imaging probe 100 proximate delivery catheter 80). Connector 180 (not shown) can be operably positioned within carrier 855, and a motive force can be applied to the distal end of linkage 891. Carrier 855 retracts within trench 889, retracting imaging probe 100 relative to the patient. After retraction, connector 180 can be removed from carrier 855 (e.g. lifted out of), and carrier 855 and imaging probe 100 can be re-advanced independently. For example, carrier 855 can re-advance via the bias of spring 852, as the proximal end of linkage 891 is allowed to advance, and imaging probe 100 can be re-advanced manually by a user. Subsequent retractions can be performed by repositioning connector 180 in carrier 855 after both have been re-advanced. Carrier 855 can comprise a capturing portion, such as the "cup-like" geometry shown, a hook, or other capture-enabling portion, such that carrier 855 can only impart a retraction force on connector 180. In this configuration, if carrier 855 were to translate distally, connector 180 would automatically disengage from carrier 855 (e.g. connector 180 would fall out of the cup portion of carrier 855).

Referring back to FIG. 7C, tensioning assembly 841 can be adjusted to assure proper operation. If tensioning assembly 841 is too "tight", distal end 892 of linkage 891 will not reach puller 850 (e.g. when puller 850 is in its distal most position). In these instances, adjustment of tensioning assembly 841 can be made to cause the distal end of linkage 891 to "reach" puller 850. If tensioning assembly 841 is too "loose", there will be slack in linkage 891 when connection assembly 845 is fully seated within housing 848b. In these instances, adjustment of tensioning assembly 841 can be made to remove the slack in linkage 891.

Figure 9:
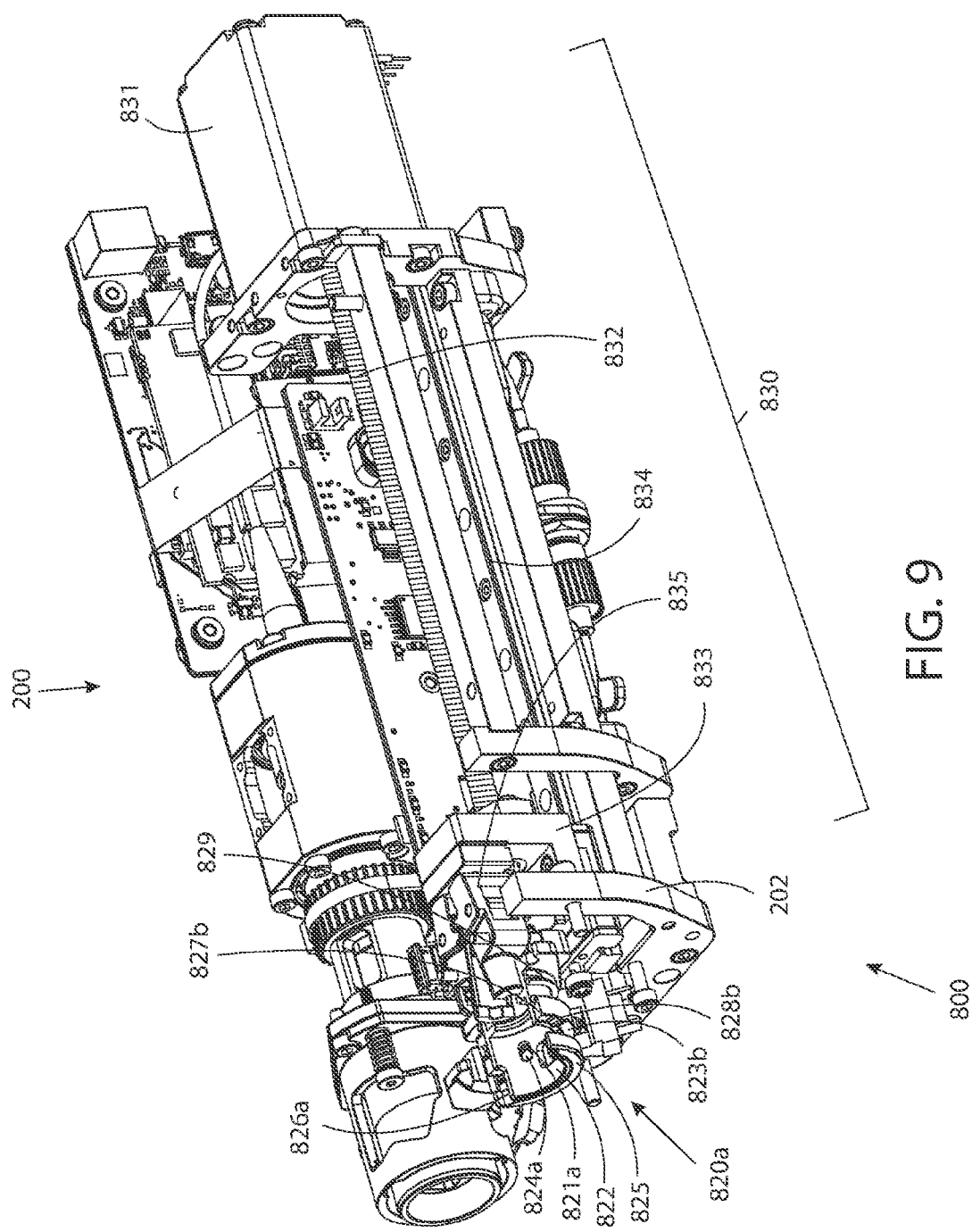
FIG. 9 illustrates a perspective view of components of a patient interface module, consistent with the present inventive concepts.

Referring now to FIG. 9, a perspective view of components of a patient interface module is illustrated, consistent with the present inventive concepts. Patient interface module 200 is configured to provide rotation to a rotatable optical core of an imaging probe, and to provide a motive force to translate at least a portion of the imaging probe, such as is described herebelow. In FIG. 9, housing 201, and other components of patient interface module 200 are removed for illustrative clarity, revealing connector assembly 820a and retraction assembly 800. In the illustrated embodiment, connector assembly 820a comprises a floating locking portion, sleeve 825. Sleeve 825 comprises one or more cut away portions, slots 827a,b (slot 827a not shown but positioned opposite slot 827b), and one or more passageways, recesses 826a,b (recess 826b not shown but positioned opposite recess 826a), providing sliding access into slots 827a,b as described herebelow. Sleeve 825 can further comprise one or more locking elements, projections 828a,b (projection 828a not shown but positioned opposite projection 828b), extending into slots 827a,b, respectively.

Sleeve 825 surrounds a fixed connection element, sleeve 822. Sleeve 822 is fixedly attached to frame 202 of patient interface module 200 (portions of frame 202 removed for illustrative clarity). Sleeve 822 can comprise one or more elongate cut away portions, slots 821a,b (slot 821b not shown but positioned opposite slot 821a), and one or more cut away portions, slots 827a,b, that slidingly receive projections 844a,b of connector 840 (connector 840 and projections 844 not shown). Sleeve 825 is slidingly received over sleeve 822. Slots 827a,b are aligned with slots 823a,b, (slot 823a not shown but positioned opposite slot 823b) and recesses 826a,b are aligned with the distal opening of slots 823a,b, such that when housing 848b (not shown) of connector 840 is slidingly received within sleeve 822, projections 844a,b are slidingly received by both slots 823a,b and slots 827a,b, respectively. Slots 823a,b and 827a,b can each comprise a geometry (e.g. an elongated, curvilinear opening) such that after projections 844a,b are received therein, connector 840 can be rotated (e.g. rotated clockwise), as projections 844a,b translate within slots 823a,b and 827a,b, locking connector 840 to connector assembly 820a.

Sleeve 825 can be slidingly attached to sleeve 822 via one or more securing elements, pins 824a,b (pin 824b not shown but positioned opposite pin 824a) through sleeve 822, extending into slots 821a,b of sleeve 822. In some embodiments, connector assembly 820a comprises a biasing element, spring 829. Spring 829 can provide a biasing force to sleeve 825, such that pins 824a,b engage the distal end of slots 821a,b, respectively. In this embodiment, as connector 840 is rotated within connector assembly 820a, projections 828a,b impede the rotation by frictionally engaging projections 844a,b within slots 827a,b, respectively. As projections 844a,b engage projections 828a,b, sleeve 825 is forced inwards against spring 829, and returns as projections 844a,b continue past projections 828a,b. Spring 829 provides a retention force, preventing (or at least limiting the likelihood of) connector 840 from rotating past projections 828a,b and unintentionally disconnecting from connector assembly 820a.

Patient interface module 200 includes motive element 830 of retraction assembly 800. Motive element 830 can be configured to provide a motive force that causes translation (e.g. retraction) of at least a portion of an imaging probe of the present inventive concepts. In the embodiment shown, motive element 830 comprises a linear actuator including a worm gear driven cart. Motive element 830 includes motor 831, operably attached to a worm gear, drive 832. A translating fixture, cart 833, is slidingly affixed to a linear bearing, slide 834. Slide 834 and motor 831 are fixedly attached to frame 202 of patient interface module 200. Drive 832 operably engages cart 833, such that as drive 832 is rotated by motor 831, cart 833 translates along slide 834. A connector that is fixedly attached to cart 833, connector 835, releasably attaches to connection point 842 (not shown) of connector 840, for example when connector 840 is operably attached to connector assembly 820a. Connector 835 can comprise a clamshell or other locking construction, configured to "grasp" or otherwise engage a connector, such as connection point 842. Connector 835 can be biased in an "open" position, as shown, when cart 833 is in its distal most position, ready to receive a connection point. As cart 833 is moved proximally, connector 835 can close around an inserted connection point, operably attaching thereto. One or more cams, springs, hinges, leavers, ramps, or other mechanisms can be included in connector 835 and/or motive element 830 to bias and/or operably open and close connector 835. In some embodiments, connector 835 comprises an electromagnetic connector, such as an electromagnet, configured to operably attach to a connection point via magnetic attraction. In these and other embodiments, connector 835 can automatically disconnect from an attached connection point in the case of an emergency (e.g. a power loss), to allow a user to disconnect a pullback device from retraction assembly 800.

Referring now to FIGS. 10A and 10B, perspective and partial sectional views of a connector assembly are illustrated, respectively, consistent with the present inventive concepts. As described hereabove in reference to FIG. 1B, in some embodiments, a patient interface module 410 operably connects an imaging probe of the present inventive concepts to a patient interface module (e.g. module 200 described herein), to provide rotation of its optical core and to provide translation to at least a portion of the probe. FIG. 10A is a perspective view of patient interface module 410, and FIG. 10B is a partial sectional view of module 410 with a portion of the housing of module 410 removed.

Module 410 can comprise a two-part housing 411, comprising top portion 411a and bottom portion 411b, surrounding an opening therein, chamber 413. Module 410 can include an extending portion surrounding a lumen, conduit 415, extending distally from housing 411. Conduit 415 can comprise a flexible conduit. Conduit 415 can comprise an additional strain relief 412 at its distal end, fixedly attached to a proximal shaft 481 of attached delivery catheter 480. Delivery catheter 480 can be of similar construction to delivery catheter 80 described herein. Delivery catheter 480 can comprise at least a portion that is optically transparent, window 485. Window 485 can be positioned at or near a distal portion of delivery catheter 480. Window 485 can comprise a material transparent to imaging modalities utilized by imaging probe 100, such that imaging probe 100 can image through window 485, for example when optical assembly 115 is retracted within window 485. Delivery catheter 480 can comprise a distal tip 483, comprising a rapid exchange type tip and or a spring tip construction. Imaging probe 100 is slidingly received through delivery catheter 480, proximally through conduit 415, into chamber 413. Within chamber 413, service loop 185 accommodates at least a partial retraction of imaging probe 100 into chamber 413. Imaging probe 100 operably attaches to an optical connector assembly, connector assembly 150'. Connector assembly 150' can be of similar construction and arrangement to connector assembly 150 described hereabove in reference to FIGS. 3 through 6D. For example, connector assembly 150' can connect to patient interface module 200 in a similar manner to connector assembly 150, as described herein. Connector body 151 of connector assembly 150' is slidingly received within connector assembly 510, and projections 153 rotatably engage openings 517, as described hereabove in reference to FIGS. 6A-D, providing a locked, floating (rotatable) optical connection of imaging probe 100 to optical rotary joint 550, also as described herein. Connector assembly 150' can comprise a projection, lever 157', which allows a user to rotate connector body 151, engaging connector assembly 510. Module 410 can comprise a biasing element, spring 414. Spring 414 can provide a biasing force to a portion of connector assembly 150', such as a portion of connector assembly 150' configured to translate to accommodate motion required to perform a locking action to operably connect connector assembly 150' to connector 510.

Module 410 can comprise a linkage, puller 850'. Puller 850' can comprise a rod, a cable, and/or other linkage configured to apply a retraction force to one or more portions of imaging probe 100. In some embodiments, puller 850 is further configured to advance imaging probe 100. Puller 850' extends from a connector, connector 840', through housing 411 and conduit 415, terminating proximate the distal end of conduit 415. Puller 850' can operably attach to imaging probe 100, for example puller 850' can be fixedly attached (e.g. glued or clamped) to imaging probe 100 proximate the distal end of puller 850'. Puller 850' can comprise a connection point 842'. Connection point 842' can be of similar construction and arrangement to connection point 842 of connector 840, as described hereabove in reference to FIGS. 7A-B. Connector 840' can also be of similar construction and arrangement to connector 840 of FIGS. 7A-B. For example, connector 840' can connect to patient interface module 200 in a similar manner to connector 840, as described herein. In some embodiments, connection point 842' connects to connector 835 of motive element 830 in a similar manner to connection point 842. In some embodiments, connector 840' provides a "snap" or other linear type connection to connector 820a, aligning connection point 842' with connector 835, without providing a rotationally locking engagement.

Delivery catheter 480 can comprise a proximal portion and a distal portion, proximal shaft 481 and distal shaft 482 shown. Delivery catheter 480 can comprise a purge assembly 490 (e.g. positioned between shafts 481 and 482 as shown), that allows a user to inject a fluid (e.g. a purge fluid) through distal shaft 482. Purge assembly 490 includes housing 493 which on its proximal end can attach to the distal end of shaft 481, and on its distal end attach to the proximal end of shaft 482. Fluid can be delivered through catheter 480, along imaging probe 100, exiting through and/or near the distal end of catheter 480. Purge fluid can be delivered through catheter 480 to perform one or more of: improve optical transmission by minimizing any refractive index mismatch between sheathes of imaging probe 100 and catheter 480; provide lubricity for the imaging probe 100 sliding within catheter 480; and/or remove air from the interstitial region between catheter 480 and imaging probe 100. Purge assembly 490 can comprise an injection inlet, port 491 (e.g. positioned on housing 493 as shown). Port 491 can comprise a lumen and a luer connector, or other components configured to allow a syringe or other fluid source to fluidly attach to purge assembly 490 and/or distal shaft 482 of delivery catheter 480. Purge assembly 490 can prevent or limit fluid injected into port 491 from exiting purge assembly 490 proximally, for example into proximal shaft 481, of delivery catheter 480. Housing 493 can comprise a projection, grip 492, to make purge assembly 490 easier to manipulate (e.g. by a user).

In some embodiments, purge assembly 490 is configured as an imaging probe 100 compression relief assembly that allows imaging probe 100 to safely buckle (e.g. to avoid imaging probe 100 experiencing compression above an undesired compression level threshold), such as to avoid undesired buckling within the patient (with or without additionally being configured as an assembly that allows a user to inject fluid, as described hereabove). In these embodiments, housing 493 can comprise an opening, safety port 495. When imaging probe 100 is inserted into delivery catheter 480 (e.g. inserted through proximal shaft 481, through safety port 495 and into distal shaft 482), imaging probe 100 is unsupported within safety port 495, such that safety port 495 provides a "buckle point" for imaging probe 100 in that location (e.g. safety port 495 is sized to accommodate the buckling). Should imaging probe 100 encounter resistance as it is advanced through distal shaft 482 of delivery catheter 480 (e.g. compression of imaging probe 100 increases as imaging probe 100 is advanced manually by a user or automatically by motive element 830 of patient interface module 200, as described herein), safety port 495 can allow imaging probe 100 to buckle, preventing or at least limiting the likelihood that imaging probe 100 punctures and/or otherwise undesirably exits delivery catheter 480.

Additionally or alternatively, safety port 495 can provide access for an emergency removal of imaging probe 100 from delivery catheter 480. For example, a user can manipulate the unsupported section of imaging probe 100 within safety port 495 (e.g. purposely buckle imaging probe 100 through safety port 495), grasp a portion of imaging probe 100, and remove (e.g. pull proximally) imaging probe 100 from delivery catheter 480. In some embodiments, a guide wire or other flexible elongate device is subsequently inserted into delivery catheter 480 via safety port 495.

Referring now to FIGS. 11A and 11B, two perspective views of connectors being attached to a patient interface module are illustrated, consistent with the present inventive concepts. Patient interface module 200 can be of similar construction and arrangement to patient interface module 200, as described hereabove in reference to FIGS. 4A-C, 5, 5A-B, and 9. Patient interface module 200 comprises a first physical connector assembly, connector assembly 510, for operably connecting to connector assembly 150', as described hereabove in reference to FIGS. 10A-B. Patient interface module 200 can further comprise a second physical connector assembly, connector assembly 820a, for operably connecting to connector 840', also as described hereabove in reference to FIGS. 10A-B. As shown in FIG. 11A, connector assembly 150' and connector 840' can each comprise bayonet type connectors, constructed and arranged to be at least partially inserted into connector assemblies 510 and 820a, respectively. As shown in FIG. 11B, connector assembly 150' can be subsequently rotated (e.g. an approximately 45° rotation) to lock its connection with connector assembly 510, as described hereabove in reference to FIG. 4A-C.

Figure 12:
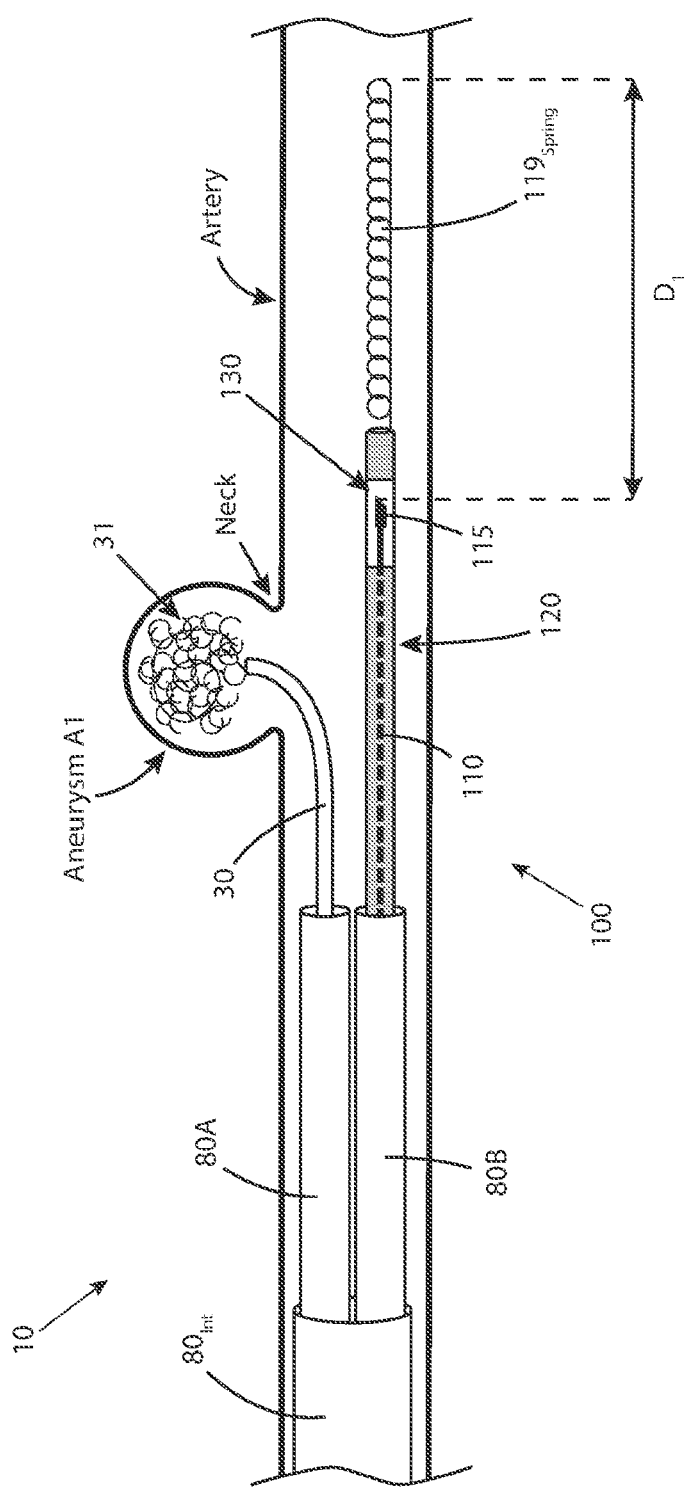
FIG. 12 illustrates a side sectional anatomical view of a system including an imaging probe in a side-by-side arrangement with an implant delivery device, consistent with the present inventive concepts.

Referring now to FIG. 12, a side sectional anatomical view of a system including an imaging probe in a side-by-side arrangement with an implant delivery device is illustrated, consistent with the present inventive concepts. System 10 includes imaging probe 100 (the distal portion of probe 100 is shown in FIG. 12), a treatment device, such as implant delivery device 30 shown, and one or more delivery catheters 80. System 10 includes at least an intermediate delivery catheter $80_{INT}$, and at least two micro delivery catheters 80a and 80b. Micro delivery catheters 80a,b are shown slidingly positioned within intermediate delivery catheter $80_{INT}$ in a side-by-side configuration. Micro delivery catheter 80a has slidingly received implant delivery device 30, and micro delivery catheter 80b has slidingly received imaging probe 100, also as shown. In some embodiments, imaging probe 100, delivery catheters 80, and implant delivery device 30 can be of similar construction and arrangement to similar components of system 10, as described herein.

Each micro delivery catheter 80a,b can comprise an inner diameter sufficient to slidingly receive implant delivery device 30 and imaging probe 100, respectively. Micro delivery catheters 80a,b can each further comprise an outer diameter such that micro delivery catheters 80a,b, collectively, can be slidingly received, in a side-by-side arrangement, within intermediate delivery catheter $80_{INT}$. Imaging probe 100 can comprise an outer diameter of not more than 0.020", for example an outer diameter of approximately 0.014". Imaging probe 100 and the various components of system 10 shown in FIG. 12 can be introduced into the patient, as described hereabove in reference to FIG. 1.

Intermediate delivery catheter $80_{INT}$ can be advanced to a first anatomic location. Subsequently, micro delivery catheters 80a,b can each be advanced to a second anatomic location distal to the first anatomic location. Imaging probe 100 can be advanced beyond the distal end of micro delivery catheter 80b, and beyond an anatomic feature, for example aneurysm $A_1$ as shown. Implant delivery device 30 can be advanced beyond the distal end of micro delivery catheter 80a, towards the anatomic feature, such as to subsequently deliver one or more implants 31 (e.g. to deliver one or more embolization coils or other aneurysm treatment components). In some embodiments, system 10 is constructed and arranged to collect image data related to implant 31, the image data collected prior to, during and/or after implantation of implants 31 (e.g. collected during a pullback procedure of probe 100). In some embodiments, implant 31 comprises multiple implants 31, for example multiple embolization coils. In these embodiments, system 10 can be constructed and arranged to collect image data during implantation (e.g. during deployment from delivery device 30) of one or more of the implants 31, and/or after implantation of one or more of each of the implants 31. In some embodiments, system 10 is configured to perform real time or near-real time ("real time" herein) imaging of implant 31 implantation (e.g. real time imaging of deployment of one or more coils or other implants). For example, system 10 can be used to perform one or more (e.g. repeating) relatively short pullbacks, each pullback including a small injection of a clearing flush. These pullbacks could be automated, and could include, approximately: a repeated set of 25 mm pullbacks, each over a time period of 1 second. For example, system 10 could be configured to (in an automated manner) deliver a 5-10 ml flush media, such as flushes delivered during every 30 seconds of deployment of one or more portions (e.g. coils) of implant 31.

In some embodiments, imaging probe 100 comprises a spring tip, tip $119_{SPRING}$. Tip $119_{SPRING}$ can comprise a length (e.g. a sufficient length) such that the distal end of tip $119_{SPRING}$ remains distal to the aneurysm during a pullback procedure of imaging probe 100 (e.g. a pullback procedure in which imaging data is collected at an imaging location while optical assembly 115 is retracted through a segment of the vessel to be imaged). After a pullback procedure is completed, and at least the distal end of tip $119_{SPRING}$ extends beyond the aneurysm, imaging probe 100 can be re-advanced beyond the aneurysm, such that optical assembly 115 is positioned distal to aneurysm $A_1$ (as shown). The distance between the distal end of tip $119_{SPRING}$ and optical assembly 115, distance $D_1$ shown, can be chosen such that after a pullback procedure is performed to image any anatomical location (e.g. an aneurysm) and/or to image any implanted device (e.g. an implanted coil and/or stent), the distal end of tip $119_{SPRING}$ is positioned to allow safe advancement of imaging probe 100 (e.g. the distal end of tip $199_{SPRING}$ is positioned within or beyond the anatomical location and/or within or beyond the implanted device). For example, distance $D_1$ can comprise a length of at least 40 mm, such as when tip $199_{SPRING}$ comprises a length of at least 35 mm, at least 50 mm, or at least 75 mm (e.g. to support a pullback of up to 25 mm, 40 mm, or 65 mm).

Figures 13A, 13B:
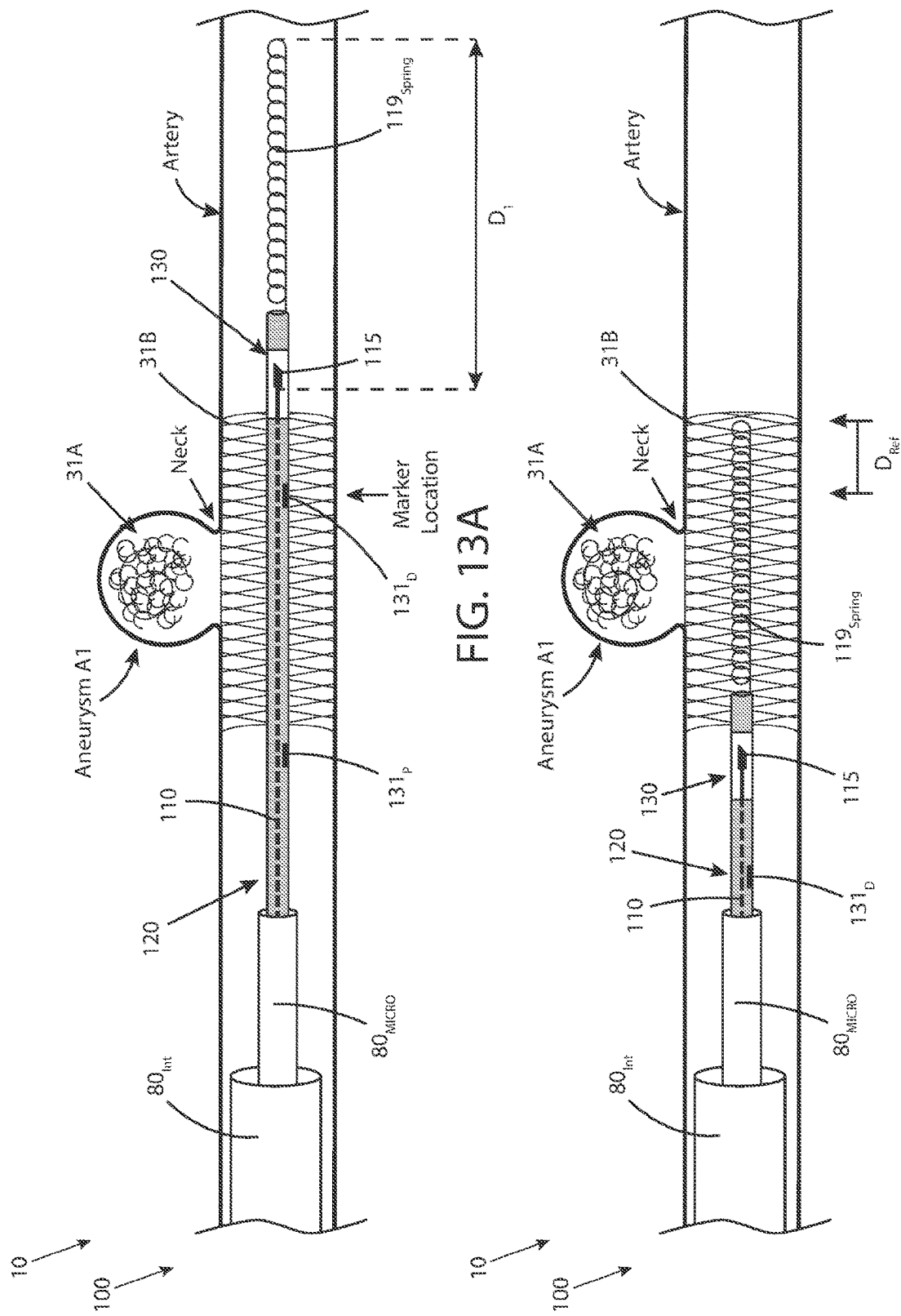
FIGS. 13A and 13B illustrate side sectional anatomic views of a system including an imaging probe including a position marker, consistent with the present inventive concepts.

Referring now to FIGS. 13A and 13B, side sectional anatomic views of a system including an imaging probe including a position marker are illustrated, consistent with the present inventive concepts. FIG. 13A illustrates system 10 that includes imaging probe 100, such as is described herein, shown advanced into a patient and extending beyond an anatomic feature (e.g. aneurysm A1 shown). System 10 further includes one or more delivery catheters used to deliver imaging probe 100, such as intermediate delivery catheter $80_{INT}$ and micro delivery catheter $80_{MICRO}$ shown. FIG. 13B illustrates imaging probe 100 after a pullback procedure has been performed (e.g. to create image data in a segment of the vessel including aneurysm A1).

Aneurysm A1 of FIGS. 13A-B has been treated with one or more embolization coils, implant 31a, and with a flow diverter, second implant 31b, implanted across the neck of the aneurysm, each as shown. Imaging probe 100 can include a first marker, marker $131_D$, positioned relative to optical assembly 115 along shaft 120 (e.g. proximal to optical assembly 115). Imaging probe 100 can further include a second marker, marker $131_P$, positioned proximal to marker $131_D$ along shaft 120. Markers $131_D$ and/or $131_P$ (singly or collectively marker 131) can comprise a marker selected from the group consisting of: radiopaque marker; ultrasonically visible marker; magnetic marker; visible marker; and combinations of these. Imaging probe 100 can include a spring tip $119_{SPRING}$, such that the distance between the distal end of tip $119_{SPRING}$ and optical assembly 115 comprises distance $D_1$ shown. Tip $119_{SPRING}$ and distance $D_1$ can comprise lengths (e.g. minimum lengths), as described hereabove in reference to FIGS. 13A-B (e.g. minimum lengths configured to allow safe advancement of imaging probe 100 after a pullback procedure has been performed, also as described hereabove). Imaging probe 100 can comprise marker $131_D$ or marker $131_P$, or it can comprise both marker $131_D$ and marker $131_P$.

Marker $131_D$ can be positioned along shaft 120 at a particular location relative to the distal end of tip $119_{SPRING}$. The position of marker $131_D$ can provide a reference (e.g. under fluoroscopy or other imaging modality) to the user of the estimated position that the distal end of tip $119_{SPRING}$ will reach after a pullback procedure (e.g. a pullback procedure of a predetermined distance, such as a maximum distance that system 10 can retract imaging probe 100). For example, as shown in FIG. 13B, after a pullback procedure, the distal end of tip $119_{SPRING}$ is a distance $D_{REF}$ from the initial position of marker $131_D$. Distance $D_1$ (e.g. as determined by the length of tip $119_{SPRING}$) and the position of marker $131_D$ can be chosen such that the estimated position of the distal end of tip $119_{SPRING}$ after a pullback procedure is performed is the same as or distal to the initial position of marker $131_D$ prior to the pullback procedure (e.g. for the maximum pullback distance enabled by system 10). For example, system 10 can be configured to retract imaging probe 100 a distance relatively equal to distance $D_1$. Alternatively or additionally, system 10 can be configured to retract imaging probe 100 a distance of no more than distance $D_1$ (e.g. after the retraction, the distal end of tip $119_{SPRING}$ is at or distal to the previous position of marker $131_D$).

In some embodiments, marker $131_P$ is positioned along shaft 120 relative to optical assembly 115. The position of marker $131_P$ can provide a reference to the user of the estimated position of optical assembly 115 after a pullback procedure of a predetermined distance.

Referring now to FIG. 14, a flow chart of a method of creating an image is illustrated, consistent with the present inventive concepts. Method 1400 of FIG. 14 will be described using the devices and components of system 10 described hereabove in reference to FIGS. 13A and 13B. In Step 1410, an imaging probe (e.g. imaging probe 100 described herein) is inserted into the vasculature of the patient. In Step 1420, a marker of the imaging probe (e.g. marker 131) is positioned relative to an imaging location, for example a location to be imaged by system 10 such as a location proximate an aneurysm, such as an aneurysm about to be treated and/or already treated (e.g. treated via implantation of a flow diverter).

System 10 can be constructed and arranged such that after a pullback procedure is performed, the distal end of imaging probe 100 (e.g. the distal end of tip 119 or tip $119_{SPRING}$) is positioned (e.g. "lands") relative to the initial position of the marker 131. For example, the relative distance between the distal end of imaging probe 100 and the marker 131 can be configured such that the distal end of tip 119 lands approximately at the initial position of the marker 131. In these embodiments, a user can position the marker 131 at or distal to a point where distal access is desired to be maintained by imaging probe 100 after the pullback procedure is performed, ensuring the distal tip of imaging probe 100 will not retract to a location proximal to that point. In Step 1430, the catheter is retracted in a pullback procedure, as described herein. In Step 1440, imaging probe 100 can be safely advanced (e.g. an advancement in which optical assembly 115 is positioned distal to the imaging location) to perform another imaging procedure (e.g. another pullback in which imaging data is collected). Alternatively, in Step 1440 a microcatheter is safely advanced over imaging probe 100, then imaging probe 100 is removed from the microcatheter, and a separate device (e.g. a treatment device) is advanced through the distally-positioned microcatheter. The separate device can then be used in a treatment or other procedure (e.g. a coil deployment procedure).

Referring now to FIGS. 15A and 15B, schematic views of a system including an imaging probe are illustrated, consistent with the present inventive concepts. System 10 can include imaging probe 100, positioned within a delivery catheter 80 (e.g. pre-loaded into a delivery catheter 80 in a manufacturing or packaging process). Imaging probe 100 and delivery catheter 80 can be of similar construction and arrangement to similar components, as described herein. Delivery catheter 80 can comprise a transparent portion, window 85. Window 85 can be constructed and arranged such that imaging probe 100 can collect image data by transmitting and receiving light that passes through window 85. In these embodiments, the optical assembly 115 can be retracted (e.g. probe 100 is retracted) and image data collected while optical assembly 115 is positioned within window 85 of delivery catheter 80. In these embodiments, access distal to the imaging location is maintained by delivery catheter 80, as imaging probe 100 can subsequently be re-advanced through delivery catheter 80 for additional pullback procedures. In some embodiments, catheter 80 is filled with saline or another optically transparent fluid, such as to limit optical distortion that can be caused by imaging through multiple layers of catheter walls (e.g. through the walls of optical probe 100 and delivery catheter 80). In some embodiments, delivery catheter 80 comprises a reinforced portion, portion 87, proximal to window 85. Portion 87 can comprise a braided construction, and/or the wall of portion 87 can comprise a greater thickness than the non-reinforced wall of delivery catheter 80. Portion 87 can be constructed and arranged to prevent or at least limit collapsing of portion 87 of delivery catheter 80 under a compressive load, for example when a connector of system 10 is attached to catheter 80 at a location within portion 87. Shaft 81 of delivery catheter 80 can comprise an outer diameter near its distal end of approximately 2.8 F. Shaft 81 can comprise an outer diameter proximate its proximal end (e.g. the outer diameter of portion 87) of approximately 3.2 F. Delivery catheter 80 can comprise a length of approximately 150 cm. The distal portion of shaft 81 can comprise a greater flexibility than the more proximal portion of shaft 81. This distal portion can comprise a length of approximately 300 mm. Delivery catheter 80 can comprise a hydrophilic coating. Delivery catheter 80 can comprise one or more markers, such as one or more radiopaque markers. Shaft 81 can comprise a braided construction. In some embodiments, one or more braids of shaft 81 terminates proximal to window 85. Shaft 81 can comprise one or more segments along its length that comprise varying durometers. The durometers of shaft 81 can vary between 45 D (e.g. segments near the distal end of shaft 81) and 74 D (e.g. segments near the proximal end of shaft 81).

In some embodiments, imaging probe 100 comprises a spring tip, tip $119_{SPRING}$, as described herein. Imaging probe 100 and delivery catheter 80 can be constructed and arranged to be inserted into a patient's vasculature, coaxially, using an "inch worm" type method. In these embodiments, imaging probe 100 can be advanced beyond the distal end of delivery catheter 80, tip $119_{SPRING}$ acting as a guidewire to navigate the vasculature. Subsequently, delivery catheter 80 can be advanced along imaging probe 100. This process can be repeated (e.g. in an "inch worm" method) until a target location has been reached (e.g. optical assembly 115 is positioned distal to the imaging location).

In some cases, a user (e.g. a clinician) may decide to use imaging probe 100 without a microcatheter, or with a different microcatheter than the one in which imaging probe 100 is provided. In these cases, the user can remove imaging probe 100 from delivery catheter 80 prior to performing a procedure (e.g. remove by retracting proximally from delivery catheter 80, via connector 82), and use imaging probe 100 with any number of delivery devices similar to those as described herein.

Figure 16B:
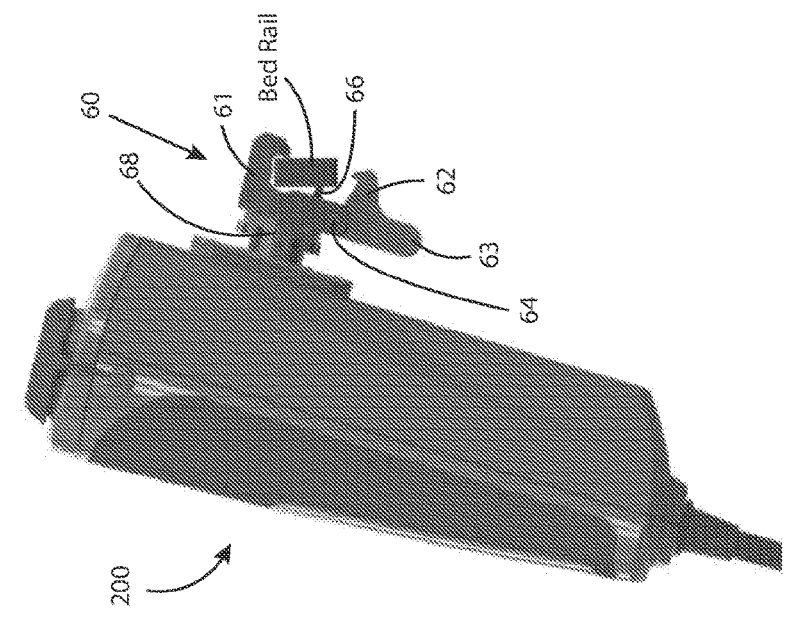
FIGS. 16A-C illustrate perspective, side, and front views, respectively, of a patient interface module attached to a bed rail mount, consistent with the present inventive concepts.
Figure 16C:
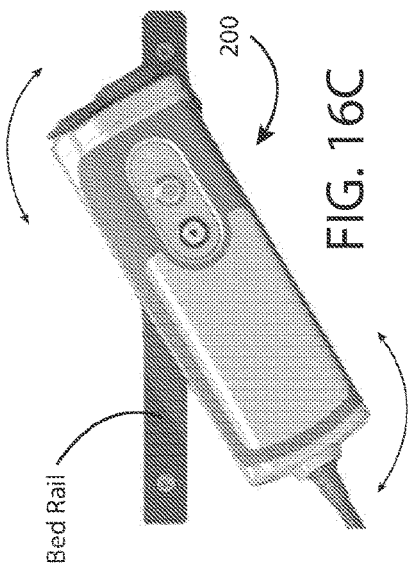
Figure 16A:
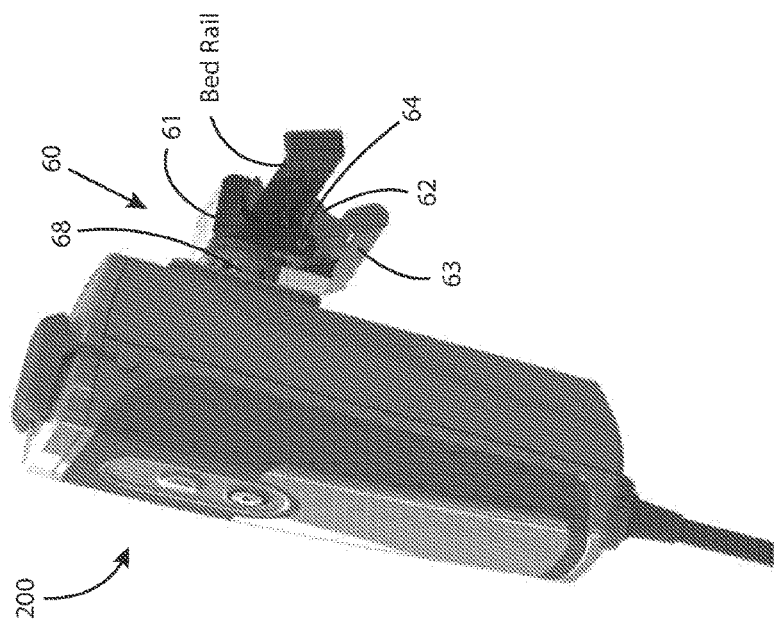

Referring now to FIGS. 16A-C, perspective, side, and front views, respectively, of a patient interface module attached to a bed rail mount are illustrated, consistent with the present inventive concepts. Bed rail mount 60 comprises an upper portion, hook 61, and a lower portion, jaw 62. Jaw 62 is configured to rotate relative to hook 61 about a pivot, axle 64. Jaw 62 can be biased in a closed position, such as via a spring or other biasing element. Jaw 62 can be locked (e.g. temporarily locked) in an open position, as shown in FIGS. 16A-B. In some embodiments, mount 60 comprises a release mechanism, button 66, positioned within hook 61. Button 66 can be configured to release jaw 62 from the (locked) open position when depressed (e.g. depressed by a bed rail as hook 61 engages the bed rail as shown in FIG. 16B), such that jaw 62 subsequently closes around the bed rail, securing mount 60 to the rail. Jaw 62 can comprise a projection, lever 63, such that a user can manipulate jaw 62 relative to hook 61. In some embodiments, jaw 62 and hook 61 are sized and oriented to capture bed rails of varying size, collectively securing to the rail (e.g. via a biasing force applied to jaw 62). Patient interface module 200 can attach to mount 60 via a connector 68. In some embodiments, connector 68 comprises a rotatable connector, such that patient interface module 200 can rotatably attach to mount 60 (e.g. module 200 can "swivel" in either direction). In these embodiments, a user can rotatably orient module 200 relative to the bed rail, as shown in FIG. 16C. In some embodiments, connector 68 is lockable in a rotated position, and/or connector 68 comprises persistent frictional rotation resistance, such that a user can reposition module 200 by overcoming the frictional force. Mount 60 can be attached to and/or rotated relative to module 200 before and/or after mount 60 is attached to a bedrail.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. An imaging system for a patient comprising:
an imaging probe, comprising:
an elongate shaft comprising a proximal end, a distal portion, and a lumen extending between the proximal end and the distal portion;
a rotatable optical core positioned within the lumen of the elongate shaft and comprising a proximal end and a distal end; and
an optical assembly positioned in the elongate shaft distal portion and proximate the rotatable optical core distal end, the optical assembly configured to direct light to tissue and collect reflected light from the tissue;
wherein the imaging probe is constructed and arranged to collect image data from a patient site;

an interface module comprising a retraction motive element constructed and arranged to provide a pullback force to a linkage assembly;
a rotation assembly constructed and arranged to optically and mechanically connect to the imaging probe, and to rotate the optical assembly; and
a retraction assembly constructed and arranged to mechanically connect to the imaging probe, and to retract the optical assembly and the elongate shaft in unison, wherein the retraction assembly comprises:
a pullback module constructed and arranged to apply a pullback force from the retraction motive element and the linkage assembly to the imaging probe,
wherein the interface module and the pullback module comprise separate housings in communication with each other by the linkage assembly.

2. The imaging system according to claim 1, wherein the pullback module housing is positioned at a first location and the interface module housing is positioned at a second location that is remote from the first location, and wherein the linkage assembly extends between the first location and the second location.

3. The imaging system according to claim 2, wherein the second location is at least 15 cm remote from the first location.

4. The imaging system according to claim 2, wherein the first second location is on or near a surgical bed rail and the first location is near a vascular access site of the patient.

5. the imaging system of claim 4, wherein the vascular access site of the patient is a first reference location and the retraction assembly and the pullback module operate relative to the first reference location, and wherein the rotation assembly operates relative to a second reference location different than the first reference location.

6. The imaging system according to claim 4, wherein the first location is within 30 cm of the vascular access site.

7. The imaging system according to claim 1, wherein the retraction motive element comprises a mechanism selected from the group consisting of: linear actuator; a worm drive operably attached to a motor; a pulley system; a linear force transfer mechanism; and combinations thereof.

8. The imaging system according to claim 1, wherein the imaging probe is configured to be manually advanced into the patient.

9. The imaging system according to claim 1, wherein the retraction assembly is configured to retract the optical assembly a distance of at least 25 mm.

10. The imaging system according to claim 1, wherein the rotation assembly is configured to rotate the optical assembly at a speed of between 20 rotations per second and 1000 rotations per second.

11. The imaging system according to claim 1, wherein the imaging probe further comprises a service loop configured to allow retraction of the imaging probe relative to the patient by the retraction motive element that applies the pullback force to the linkage assembly to retract while the rotation assembly when rotating the optical assembly remains stationary with respect to a linear movement.

12. The imaging system according to claim 1, wherein the imaging probe further comprises a connector assembly positioned on the elongate shaft proximal end, and wherein the connector assembly is configured to operably attach the imaging probe to the rotation assembly.

13. The imaging system according to claim 1, wherein the imaging probe further comprises a pullback connector positioned along the length of the elongate shaft, and wherein the pullback connector is configured to operably attach the imaging probe to the retraction assembly.

14. The imaging system according to claim 1, wherein the interface module further comprises a rotation motive element constructed and arranged to provide a rotation force for the rotation assembly.

15. The imaging system according to claim 1, wherein the pullback module comprises a puller and wherein the retraction motive element applies the pullback force to the puller via the linkage assembly.

16. The imaging system according to claim 1, further comprising a delivery catheter and wherein the pullback module comprises a connector assembly configured to attach to a connector of the delivery catheter.

17. The imaging system according to claim 16, wherein the imaging probe further comprises a pullback connector coupled to a carrier of the pullback module.

18. The imaging system according to claim 1, further comprising a service loop between a first connector and a second connector, the first connector coupled to the housing of the interface module at a first end of the service loop and the second connector coupled to the imaging probe and a carrier of the retraction assembly.

* * * * *

UNITED STATES PATENT AND TRADEMARK OFFICE
CERTIFICATE OF CORRECTION

PATENT NO. : 11,684,242 B2
APPLICATION NO. : 16/764087
DATED : June 27, 2023
INVENTOR(S) : Christopher Petroff et al.

Page 1 of 1

It is certified that error appears in the above-identified patent and that said Letters Patent is hereby corrected as shown below:

In the Claims

Column 47, Line 28, Claim 4, remove "first" before "second location".

Column 47, Line 30, Claim 5, "the" should be "The" (first occurrence).

Column 47, Line 40, Claim 7, after "of:" insert --a-- before "linear actuator".

Signed and Sealed this
Twenty-ninth Day of August, 2023

Katherine Kelly Vidal
*Director of the United States Patent and Trademark Office*